(12) United States Patent
Takeda et al.

(10) Patent No.: US 8,773,838 B2
(45) Date of Patent: Jul. 8, 2014

(54) STERILIZATION METHOD, ION GENERATING DEVICE, ION GENERATING APPARATUS, AND AIR CONDITIONING APPARATUS

(75) Inventors: Yasukata Takeda, Osaka (JP);
Yoshinori Sekoguchi, Osaka (JP);
Takeshi Furukawa, Osaka (JP);
Mamoru Morikawa, Osaka (JP);
Toshiaki Takano, Osaka (JP);
Katsutoshi Noguchi, Osaka (JP); Hideo Nojima, Osaka (JP); Kazuo Nishikawa, Osaka (JP); Akio Miyata, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 13/590,534

(22) Filed: Aug. 21, 2012

(65) Prior Publication Data
US 2012/0314333 A1 Dec. 13, 2012

Related U.S. Application Data

(62) Division of application No. 12/562,005, filed on Sep. 17, 2009, which is a division of application No. 10/110,167, filed as application No. PCT/JP01/04140 on May 17, 2001, now Pat. No. 7,854,900.

(30) Foreign Application Priority Data

| May 18, 2000 | (JP) | 2000-146009 |
|---|---|---|
| Jul. 21, 2000 | (JP) | 2000-220752 |
| Aug. 23, 2000 | (JP) | 2000-251835 |
| Aug. 24, 2000 | (JP) | 2000-253270 |
| Aug. 30, 2000 | (JP) | 2000-261135 |
| Sep. 4, 2000 | (JP) | 2000-267149 |
| Sep. 13, 2000 | (JP) | 2000-277947 |
| Sep. 25, 2000 | (JP) | 2000-290222 |
| Oct. 4, 2000 | (JP) | 2000-304942 |
| Oct. 4, 2000 | (JP) | 2000-305291 |
| Oct. 17, 2000 | (JP) | 2000-316123 |
| Feb. 23, 2001 | (JP) | 2001-47715 |

(51) Int. Cl.
*H01T 23/00* (2006.01)

(52) U.S. Cl.
CPC ................. *H01T 23/00* (2013.01)
USPC ....... 361/230; 361/231; 422/120; 422/186.04

(58) Field of Classification Search
CPC ................. A61L 9/22; H01T 23/00
USPC ........ 422/22, 120, 121, 186.04; 361/230, 231
See application file for complete search history.

(56) References Cited

U.S. PATENT DOCUMENTS 3,133,193 A * 5/1964 Guillotte et al. ............. 250/324
4,541,847 A 9/1985 Oie et al.
(Continued)

FOREIGN PATENT DOCUMENTS

| CA | 1155799 A | 10/1983 |
| DE | 19902022 A1 | 10/1999 |

(Continued)

OTHER PUBLICATIONS

Advisory Action dated Dec. 29, 2011 for U.S. Appl. No. 12/562,005.
(Continued)

*Primary Examiner* — Sean E Conley
(74) *Attorney, Agent, or Firm* — Birch, Stewart, Kolasch & Birch, LLP

(57) ABSTRACT

An ion generating device generates $O_2^-(H_2O)_n$ (where n is a natural number) as negative ions and $H^+(H_2O)_m$ (where m is a natural number) as positive ions, and discharges those ions into the air so that airborne germs are killed through an oxidation reaction by hydrogen peroxide $H_2O_2$ or radical hydroxyl OH generated through as an active species a chemical reaction between the negative and positive ions. Satisfactory sterilization is achieved when the negative and positive ions are generated in such a way that the concentrations of the negative and positive ions are both 10,000 ion/cc at a distance of 10 cm from the point at which they are generated.

10 Claims, 81 Drawing Sheets

(56) References Cited

U.S. PATENT DOCUMENTS

| | | | |
|---|---|---|---|
| 4,643,876 | A | 2/1987 | Jacobs |
| 4,883,045 | A | 11/1989 | Theisz |
| 5,087,428 | A * | 2/1992 | Fletcher et al. .......... 422/186.07 |
| 5,095,400 | A | 3/1992 | Saito |
| 5,268,151 | A * | 12/1993 | Reed et al. ............... 422/186.16 |
| 5,603,895 | A | 2/1997 | Martens et al. |
| 5,698,164 | A | 12/1997 | Kishioka et al. |
| 5,883,934 | A | 3/1999 | Umeda |
| 6,245,126 | B1 | 6/2001 | Feldman et al. |
| 6,508,982 | B1 | 1/2003 | Shoji |

FOREIGN PATENT DOCUMENTS

| | | |
|---|---|---|
| DE | 19903022 | 10/1999 |
| GB | 2304576 A | 3/1997 |
| JP | 49-129493 | 12/1974 |
| JP | 55-54957 A | 4/1980 |
| JP | 64-84264 A | 3/1989 |
| JP | 3-89123 A | 9/1991 |
| JP | 04-090428 | 3/1992 |
| JP | 4-135615 | 5/1992 |
| JP | 5-330805 A | 12/1993 |
| JP | 7-23777 | 1/1995 |
| JP | 7-89702 A | 4/1995 |
| JP | 7-187611 A | 7/1995 |
| JP | 8-217412 A | 8/1996 |
| JP | 8-255669 A | 10/1996 |
| JP | 9-192209 A | 7/1997 |
| JP | 11-60207 A | 3/1999 |
| JP | 3061585 U | 6/1999 |
| JP | 11-221270 A | 8/1999 |
| KR | 0178907 A2 | 4/1986 |
| KR | 1991-0002600 | 4/1991 |
| KR | 1995-0016885 | 7/1995 |
| KR | 97-011446 | 7/1997 |
| KR | 0120734 | 4/1998 |
| KR | 1998-17949 A | 6/1998 |
| RU | 2061501 C1 | 6/1996 |
| RU | 2090057 C1 | 9/1997 |

OTHER PUBLICATIONS

Advisory Action dated Dec. 30, 2010 for U.S. Appl. No. 12/562,005.

Chemistry A World of Choices, McGraw-Hill, 2001, p. 268 with Partial Translation.

Cotton, F et al., "Modern Inorganic Chemistry," Moscow, Mir. 1969, pp. 11-13 (in Russian).

E. Gazda, J. Phys. B: At. Mol. Phys. 19 (1986), 2973-2978 "The mobility of H+(H2O)n ions in water vapour".

Examiners Answer dated May 25, 2012 for U.S. Appl. No. 12/562,005.

General Chemistry, McGraw-Hill, 1993, p. 435, with Partial Translation.

Mass Spectrometry Resource, Atmospheric Pressure Chemical Ionisation (APCI), University of Bristol (Internet Resource), Nov. 8, 2008.

Office Action dated Apr. 29, 2011 for U.S. Appl. No. 12/562,005.

Office Action dated May 26, 2010 for U.S. Appl. No. 12/562,005.

Office Action dated Oct. 12, 2011 for U.S. Appl. No. 12/562,005.

Office Action dated Oct. 15, 2010 for U.S. Appl. No. 12/562,005.

Rapid Communications in Mass Spectrometry, vol. 11, Issue 16, Dec. 4, 1998, pp. 1757-1766.

Senior High School Textbook Chemistry, 1977, p. 39, with Partial Translation.

Superoxide involvement in the bactericidal effects of negative air ions on *Staphylococcus albus*, Nature, 281, Oct. 4, 1979, pp. 400-401.

Rapid Communications in Mass Spectrometry vol. 11, Issue 15, pp. 1257-1258.

Superoxide involvement in the bacterioidal effects of negative air ions on *Staphylococcus albus*, Nature, 281, pp. 400-401.

Cotton, F et al., "Modern Inorganic Chemistry," Moscow, MI, 1989, pp. 11-13 (in Russian).

E. Gazda, J. Phys. B. At. Mol. Phys. 18 (1930), 2973-2978, "The mobility of H+$(H_2O)_n$ ions in water vapor".

* cited by examiner $H^+(H_2O)m^+ O_2^-(H_2O)n \longrightarrow \cdot OH, H_2O_2$

STERILIZATION METHOD, ION GENERATING DEVICE, ION GENERATING APPARATUS, AND AIR CONDITIONING APPARATUS

This application is a divisional of, and claims 35 U.S.C. §120 priority to, application Ser. No. 12/562,005, filed Sep. 17, 2009. Application Ser. No. 12/562,005 is a divisional of and claims 35 U.S.C. §120 priority to, application Ser. No. 10/110,167 (U.S. Pat. No. 7,854,900 issued Dec. 21, 2010) filed Apr. 9, 2002. Application Ser. No. 10/110,167 is the national phase under 35 U.S.C. §371 of International Application No. PCT/JP01/04140, which has an International filing date of May 17, 2001, which designated the United States of America. Priority is claimed under 35 U.S.C. §119 to the following Japanese patent applications: 2000-146009, filed May 18, 2000; 2000-220752, filed Jul. 21, 2000; 2000-251835, filed Aug. 23, 2000; 2000-253270, filed Aug. 24, 2000; 2000-261135, filed Aug. 30, 2000; 2000-267149, filed Sep. 4, 2000; 2000-277947, filed Sep. 13, 2000; 2000-290222, filed Sep. 25, 2000; 2000-304942, filed Oct. 4, 2000; 2000-305291, filed Oct. 4, 2000; 2000-316123, filed Oct. 17, 2000; and 2001-047715, filed Feb. 23, 2001. The foregoing applications are incorporated herein by reference.

TECHNICAL FIELD

The present invention relates to a sterilization method whereby sterilization is achieved by generating negative and positive ions, to an ion generating device for generating negative and positive ions, to an ion generating apparatus, and to an air conditioning apparatus (any apparatus that produces the desired environmental conditions by altering the properties of air, such as an air purifier, air conditioner, dehumidifier, humidifier, fan heater (using, for example, kerosene or electricity as a heat source), or refrigerator.

BACKGROUND ART

In recent years, as homes and buildings are increasingly built air-tight, more and more people have been seeking healthy and comfortable life by removing airborne germs that are hazardous to human health from the air. In response to this trend, there have been developed many air purifiers fitted with various types of filter.

However, these air purifiers work by sucking the air in and then filtering it so that contaminants are absorbed or decomposed. Thus, as such air purifiers are used for an extended period, they imperatively requires maintenance, such as the exchanging of filters. Moreover, such air purifiers do not offer satisfactory performance because of their insufficient filtering characteristics.

On the other hand, there have also been developed air purifiers and air conditioners that work by increasing the ion concentration in the air by the use of an ion generating apparatus. However, the models that have been put on the market to date is of a type that generates negative ions alone. Although negative ions are expected to have some effect of relaxing humans, they have been found to have almost no effect of actively removing airborne germs from the air.

Moreover, conventional ion generating apparatus rely on a direct-current high-voltage system or pulse high-voltage system to generate and discharge negative ions from a sparkling needle. Thus, these ion generating apparatus require a high voltage of 5 kV or higher. This causes dust to collect in large amounts on a product incorporating such an ion generating apparatus and on an appliance or other object placed nearby.

Moreover, to secure satisfactory safety against the use of a high voltage, such a product needs to be provided with some safety measure, as by being equipped with a safety circuit.

DISCLOSURE OF THE INVENTION

An object of the present invention is to provide a sterilization method that permits efficient sterilization of airborne germs by the action of negative and positive ions discharged into the air. Another object of the present invention is to provide an ion generating device used to carry out such a sterilization method. Another object of the present invention is to provide an ion generating apparatus and an air conditioning apparatus that employ such an ion generating device to realize a comfortable and clean living environment.

To achieve the above objects, according to the present invention, a sterilization method involves discharging negative and positive ions into the air so that airborne germs are killed by the action of those ions.

Here, as the negative and positive ions, $O_2^-(H_2O)_n$ (where n is a natural number) and $H^+(H_2O)_m$ (where m is a natural number), respectively, are generated, and these ions are discharged into the air so that airborne germs are killed through an oxidization reaction by hydrogen peroxide $H_2O_2$ or radical hydroxyl OH generated as an active species through a chemical reaction between the negative and positive ions.

Moreover, according to the present invention, the concentrations of the negative and positive ions are both 10,000 ions/cc (cubic centimeter) or higher at a distance of 10 cm from the point at which the ions are generated. Experiments have proved that ion concentrations of 10,000 ions/cc or higher are essential to achieve satisfactory sterilization.

According to the present invention, an ion generating device generates negative and positive ions and kills airborne germs by the action of those ions.

Here, as the negative and positive ions, $O_2^-(H_2O)_n$ (where n is a natural number) and $H^+(H_2O)_m$ (where m is a natural number), respectively, are generated, and these ions are discharged into the air so that airborne germs are killed through an oxidization reaction by hydrogen peroxide $H_2O_2$ or radical hydroxyl OH generated as an active species through a chemical reaction between the negative and positive ions that takes place after the generation of those ions.

Specifically, the ion generating device is provided with a dielectric, a first electrode, and a second electrode, and the first and second electrodes are arranged so as to face each other with the dielectric disposed in between. The ion generating device generates negative and positive ions by applying an alternating-current voltage between the first and second electrodes.

Here, sufficient concentrations of the negative and positive ions to achieve satisfactory sterilization are secured by the application of a comparatively low alternating-current voltage of 2.0 kV rms or lower. The concentrations of the negative and positive ions thus secured are both 10,000 ions/cc or higher at a distance of 10 cm from the point at which the ions are generated.

More specifically, in one arrangement, the ion generating device is provided with a dielectric that is cylindrical in shape, an inner electrode that is formed as a mesh, and an outer electrode that is formed as a mesh, and the inner and outer electrodes are arranged so as to face each other with the dielectric disposed in between. The ion generating device generates negative and positive ions by applying an alternating-current voltage between the inner and outer electrodes.

Here, the inner electrode may be formed into a cylindrical shape by rolling a material thereof in such a way that, when the inner electrode is fitted along the inner surface of the cylindrical dielectric, opposite side edges of the rolled material overlap. This makes it possible to put the inner electrode into contact with the inner surface of the cylindrical dielectric easily and reliably.

Here, if it is assumed that the external diameter of the dielectric is 20 mm or less, that the thickness thereof is 1.6 mm or less, that the inner electrode has 40 meshes/inch, and that the outer electrode has 16 meshes/inch, then sufficient concentrations of the negative and positive ions to achieve satisfactory sterilization with minimum generation of ozone are secured by the application of a comparatively low alternating-current voltage of 2.0 kV rms or lower. The concentrations of the negative and positive ions thus secured are both 10,000 ions/cc or higher at a distance of 10 cm from the point at which the ions are generated.

The dielectric may be stopped at both ends with elastic rubber members so that the inner and outer electrodes do not move relative to each other along the axis of the dielectric. This helps stabilize the performance of the ion generating device so that it generates negative and positive ions with better reproducibility.

In this case, the elastic rubber members are preferably made of ethylene-propylene rubber, which is resistant to ozone.

Moreover, as the leads that are connected to the inner and outer electrodes are preferably used stainless steel wires coated with a polyethylene fluoride resin, which also is resistant to ozone.

In this case, the inner electrode needs to be at least thick enough to permit one of the leads to be bonded thereto.

The inner or outer electrode may be provided with a means for improving the contact thereof with the dielectric. This helps further stabilize the performance of the ion generating device.

The surface of the dielectric may be impregnated with a catalyst for promoting decomposition of ozone. This helps reduce the concentration of ozone generated as a byproduct when the ion generating device generates the ions.

Instead, the inner or outer electrode may be impregnated with a catalyst for promoting decomposition of ozone.

Instead, an ozone decomposition catalyst impregnated member impregnated with a catalyst for promoting decomposition of ozone may be provided at a distance from the dielectric. This makes it possible to use as the alternating-current voltage a voltage of 2.5 kV rms or lower.

In another arrangement, the ion generating device according to the present invention is provided with a dielectric that is cylindrical in shape, an inner electrode that is formed as a sheet, and an outer electrode that is formed as a mesh, and the inner and outer electrodes are arranged so as to face each other with the dielectric disposed in between. The ion generating device generates negative and positive ions by applying an alternating-current voltage between the inner and outer electrodes.

In this arrangement, electric discharge takes place between electrodes of which one acts as an aggregate of lines and the other a surface. This ensures stable generation of negative and positive ions. Moreover, by modifying this arrangement in similar manners as with the first arrangement described above, it is possible to gain similar advantages.

In this case, the inner electrode may be formed out of a polygonal sheet having a number of corners so that, when the inner electrode is formed into a cylindrical shape by rolling the polygonal sheet, at least one of the corners protrudes from an end of the cylinder. Such a corner protruding from the inner electrode makes the electric field more likely to concentrate on it, and thereby helps electric discharge occur with more stability than with a cylinder with trimmed ends.

The inner electrode may have a plurality of holes formed therein, with projections formed around the holes so as to protrude toward the dielectric. This makes the electric field more likely to concentrate on the side surface of the cylinder as well, and thus helps electric discharge occur stably and uniformly over the entire side surface of the inner electrode.

According to the present invention, an ion generating apparatus is provided with, in addition to an ion generating device as described above, a high alternating-current voltage source for feeding the ion generating device with the alternating-current voltage with which the ion generating device generates the negative and positive ions, and a blower for producing a forced flow of the negative and positive ions generated by the ion generating device.

With this ion generating apparatus, the negative and positive ions generated by the ion generating device fed with the alternating-current voltage from the high alternating-current voltage source can be discharged into a large expanse of air by the action of the blower so that airborne germs are killed by the action of those ions.

According to the present invention, an air conditioning apparatus is provided with, in addition to an ion generating device as described above, a high alternating-current voltage source for feeding the ion generating device with the alternating-current voltage with which the ion generating device generates the negative and positive ions, a blower for producing a forced flow of the negative and positive ions generated by the ion generating device, an inlet through which air is sucked in, an outlet through which, by the action of the blower, the negative and positive ions generated by the ion generating device is blown out together with the air sucked in through the inlet, and a filter, disposed in the air flow passage leading from the inlet to the outlet, for removing foreign particles from the air.

With this air conditioning apparatus, the negative and positive ions generated by the ion generating device fed with the alternating-current voltage from the high alternating-current voltage source can be discharged into a large expanse of air by the action of the blower so that airborne germs are killed by the action of those ions. Moreover, while the air is circulated, the filter removes dust and other foreign particles as well as odors from the air. This helps realize a comfortable and clean living environment.

Alternatively, according to the present invention, an air conditioning apparatus is provided with, in addition to an ion generating device as described above, a high alternating-current voltage source for feeding the ion generating device with the alternating-current voltage with which the ion generating device generates the negative and positive ions, a blower for producing a forced flow of the negative and positive ions generated by the ion generating device, an inlet through which air is sucked in, an outlet through which, by the action of the blower, the negative and positive ions generated by the ion generating device is blown out together with the air sucked in through the inlet, a filter, disposed in the air flow passage leading from the inlet to the outlet, for removing foreign particles from the air, and a heat exchanger disposed in the air flow passage.

With this air conditioning apparatus, the negative and positive ions generated by the ion generating device fed with the alternating-current voltage from the high alternating-current voltage source can be discharged into a large expanse of air by the action of the blower so that airborne germs are killed by the action of those ions. Moreover, while the air is circulated, the temperature or humidity of the air is adjusted by the heat exchanger, and the filter removes dust and other foreign particles as well as odors from the air. This helps realize a comfortable and clean living environment.

BEST MODE FOR CARRYING OUT THE INVENTION

Figure 1:
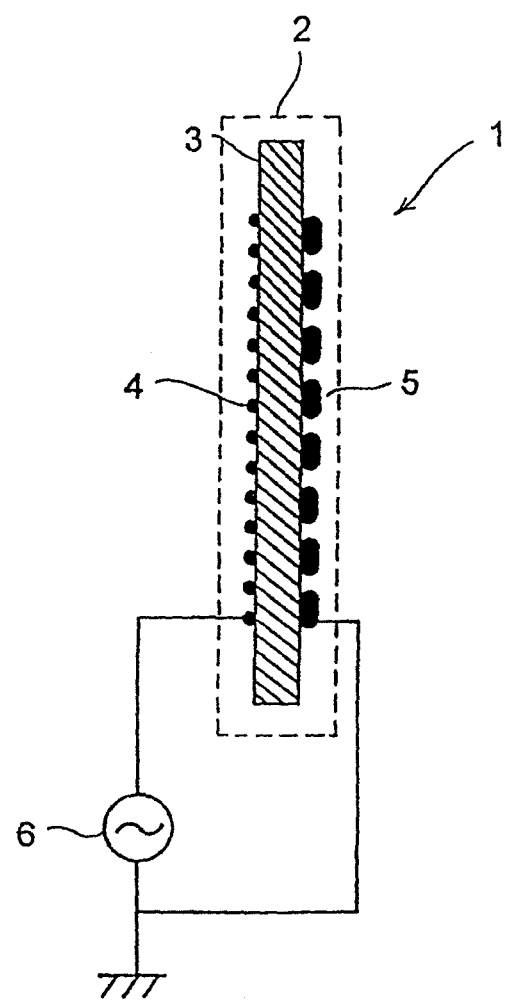
FIG. 1 is a diagram showing an outline of the structure of the ion generating device of a first embodiment of the invention.
Figure 2:
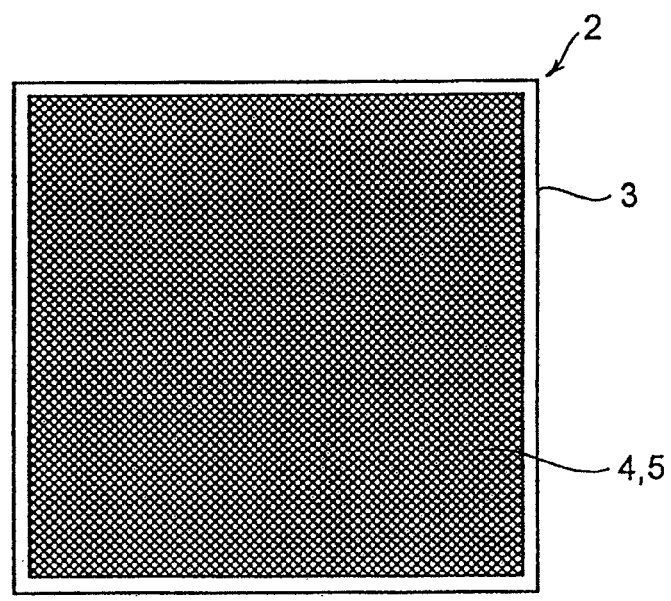
FIG. 2 is a plan view showing the ion generating electrode member used in the ion generating device.

Hereinafter, embodiments of the present invention will be described with reference to the drawings. FIG. 1 is a diagram showing an outline of the structure of the ion generating device of a first embodiment of the invention. FIG. 2 is a plan view showing the ion generating electrode member used in this ion generating device 1.

As shown in FIG. 1, the ion generating device 1 of this embodiment is composed of an ion generating electrode member 2 having a first electrode 4 and a second electrode 5 arranged so as to face each other with a glass plate 3, acting as a dielectric, disposed in between, and a high alternating-current voltage source 6 connected to the first and second electrodes 4 and 5 in such a way that the first electrode 4 serves as a voltage application electrode and the second electrode 5 serves as a grounding electrode.

As shown in FIGS. 1 and 2, the ion generating electrode member 2 has the first electrode 4 kept in intimate contact with one side of the glass plate 3, which is shaped like a flat plate, and has the second electrode 5 kept in intimate contact with the other side of the glass plate 3.

In the ion generating electrode member 2 shown in FIG. 2, a glass plate 3 is used as a dielectric; however, any other insulating material formed into any other shape may be used instead according to the shape and structure of the apparatus in which the ion generating device 1 is incorporated.

As the glass plate 3, for example, a flat plate made of Pyrex glass is used. As the first and second electrodes 4 and 5, for example, wire meshes produced by plain-weaving wire of stainless steel 316 or 304 are used.

For enhanced ion generation efficiency, the first and second electrodes 4 and 5 are kept in intimate contact with the glass plate 3. The first and second electrodes 4 and 5 can easily be put into intimate contact with the glass plate 3 by bonding, by press-fitting with pieces of wire wound around, by screen printing, or by any other known process.

Now, how the ion generating device 1 structured as described above operates will be described in terms of practical examples. It is to be understood, however, that the ion generating device 1 of this embodiment is not limited to any of the examples specifically described below, but may be implemented with modifications made in operating conditions and other factors as required.

Example 1

As the glass plate 3, a flat plate of Pyrex glass, 55 mm×55 mm and 1.0 mm thick, was used. As the first and second electrodes 4 and 5, wire meshes, each 33 mm×33 mm and having 48 meshes/inch, produced by plain-weaving wire of stainless steel 304, 0.23 mm across, were used. It is to be noted that "meshes/inch" used here as a unit describing how fine the meshes of a mesh are denotes the number of holes (meshes) found along a length of one inch; that is, the greater the meshes/inch number of a mesh, the finer its meshes.

By activating the high alternating-current voltage source 6, an alternating-current voltage of 3.0 kV rms having a frequency of 20 kHz was applied to the first electrode 4, with the second electrode 5 at the ground potential. Then, using an airborne ion counter, model 83-1001B manufactured by Dan Kagaku Co., Ltd., Japan, the concentrations of negative and positive ions with mobility of 1 $cm^2/V \cdot sec$ or higher were measured at a measurement point located 10 cm away from the side of the glass plate 3 on which the first electrode 4 is arranged. The measurement showed the presence of about 60,000 to 70,000 ions/cc of negative and positive ions. The concentration of ozone was 0.01 to 0.06 ppm.

In this way, by operating the ion generating device 1 with a comparatively low alternating-current voltage of 3.0 kV rms applied, it is possible to generate a sufficient amount of negative and positive ions in the air.

Example 2

As the glass plate 3, a flat plate of Pyrex glass, 55 mm×55 mm and 0.23 mm thick, was used. As the first and second electrodes 4 and 5, wire meshes, each 33 mm×33 mm and having 48 meshes/inch, produced by plain-weaving wire of stainless steel 304, 0.23 mm across, were used.

By activating the high alternating-current voltage source 6, an alternating-current voltage of 1.5 kV rms having a frequency of 30 kHz was applied to the second electrode 5, with the first electrode 4 at the ground potential. Then, using an airborne ion counter, model 83-1001B manufactured by Dan Kagaku Co., Ltd., Japan, the concentrations of negative and positive ions with mobility of 1 $cm^2/V \cdot sec$ or higher were measured at a measurement point located 10 cm away from the side of the glass plate 3 on which the first electrode 4 is arranged. The measurement showed that the concentration of negative ions was 14,998 ions/cc, and that the concentration of positive ions was 19,686 ions/cc. The concentration of ozone was 0.05 ppm.

In this way, by operating the ion generating device 1 with a comparatively low alternating-current voltage of 1.5 kV rms applied, it is possible to generate a sufficient amount of negative and positive ions in the air. Moreover, the frequency of the voltage applied is 30 kHz, i.e. beyond the range of human hearing, and therefore the ion generating device 1 operates quietly, with no noise produced by the electric discharge that takes place between the first and second electrodes 4 and 5.

Figure 3:
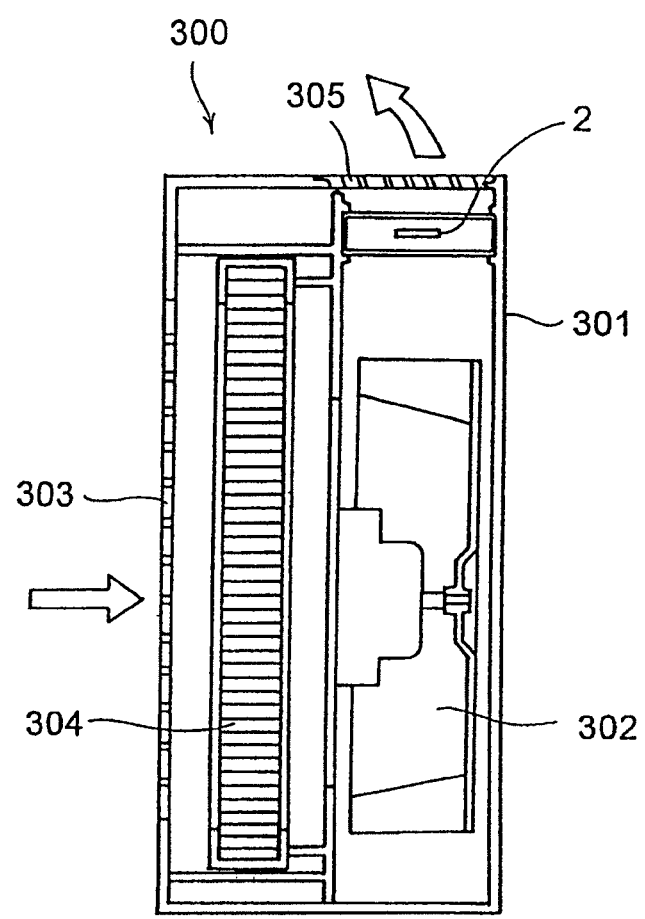
FIG. 3 is a sectional view showing an outline of the structure of the air purifier, incorporating an ion generating device, of a second embodiment of the invention.

Next, a second embodiment of the invention will be described with reference to the drawings. FIG. 3 is a sectional view showing an outline of the structure of the air purifier 300, incorporating an ion generating device 1, of a second embodiment of the invention.

In a rear portion inside the body 301 of the air purifier 300, a blowing fan 302 is provided. In the front face of the body 301, an air inlet 303 is formed that consists of a number of holes or slits. On the downstream side of the inlet 303, various filters 304 for dust removal and deodorization are provided. In the top face of the body 301, an air outlet 305 is formed that consists of a number of holes or slits. In this way, an air flow passage that leads from the inlet 303 to the filters 304 and then to the outlet 305 is formed inside the body 301.

Moreover, the ion generating device 1 (see FIG. 1) of the first embodiment described earlier is arranged with its ion generating electrode member 2 placed in the air flow passage, in the vicinity of the outlet 305. Here, the high alternating-current voltage source 6 (see FIG. 1) may be provided separately from a power source for driving the blowing fan 302, or may be shared for this purpose also. In the latter case, a controller (not shown) is additionally provided so that the driving of the blowing fan 302 and the operation of the ion generating device 1 can be controlled independently. This permits the ion generating device 1 to be turned on and off as required while the air purifier 300 is operating, and thus enhances the usability of the air purifier 300.

When this air purifier 300, structured as described above, starts operating, the blowing fan 302 starts rotating. As a result, the air sucked through the inlet 303 into the air flow passage is passed through the filters 304, which remove dust and odors from the air, and is then blown out through the outlet 305. Meanwhile, if the ion generating device 1 is kept on, the negative and positive ions generated in the space around the ion generating electrode member 2 are blown out together with the clean air. In this way, it is possible to kill airborne germs by the action of negative and positive ions.

Now, how airborne germs are killed and removed by the action of negative and positive ions will be described briefly. As the ion generating device 1 operates, plasma discharge occurs between the first and second electrodes 4 and 5 that are arranged so as to face each other with the glass plate 3 disposed in between. This plasma discharge ionizes the molecules of water vapor contained in the air into negative and positive ions.

Figure 82:
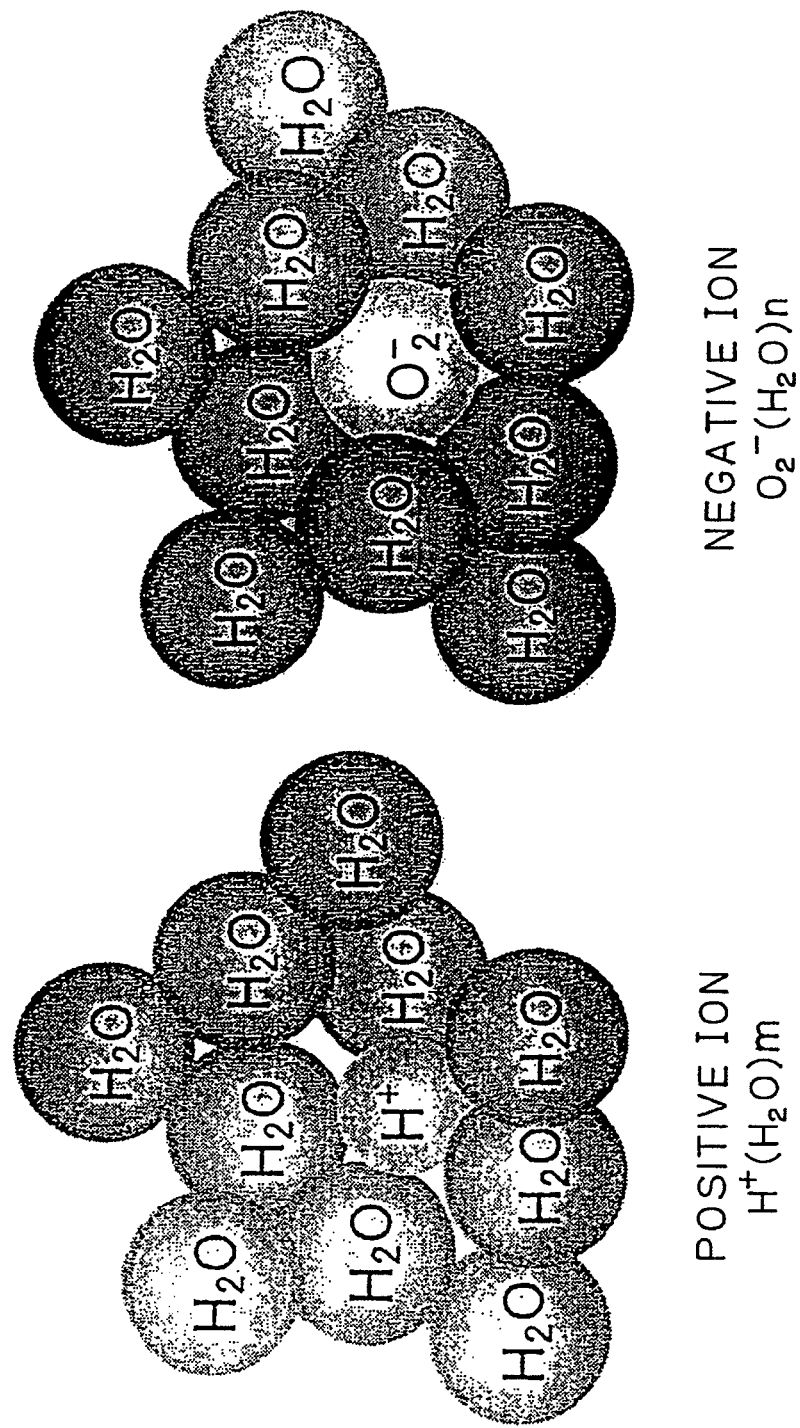
FIG. 82 is a diagram illustrating the structure of the negative and positive ions generated by the operation of an ion generating device embodying the invention.
Figure 83:
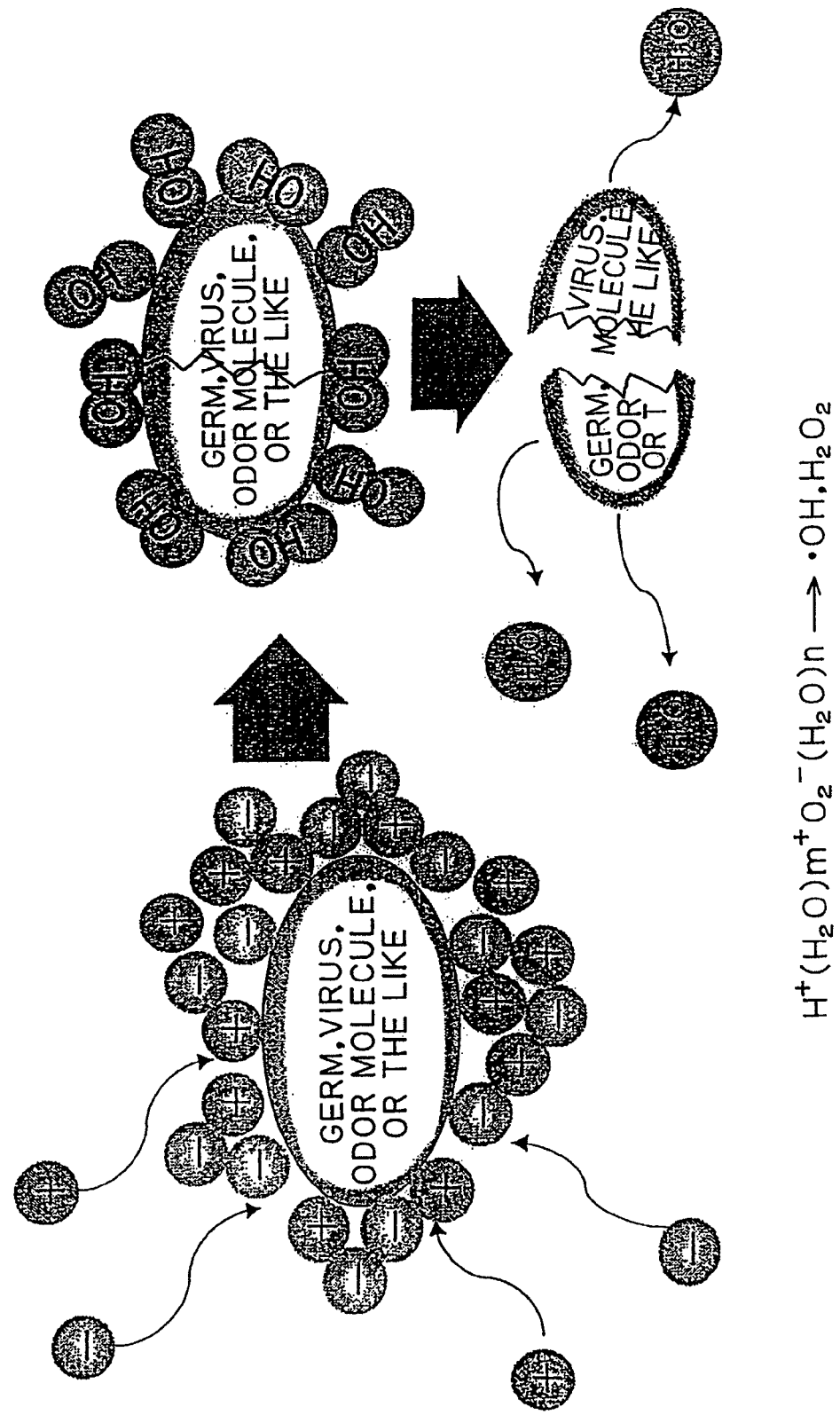
FIG. 83 is a diagram illustrating how airborne germs, viruses, odor molecules, and other foreign particles are decomposed by the action of negative and positive ions.

Here, as shown in FIG. 82, as the positive ions, hydrated hydrogen ions $H^+(H_2O)_m$ are generated, and, as the negative ions, hydrated oxygen ions $O_2^-(H_2O)_n$ are generated. Here, m and n represent natural numbers.

When these ions attach to the surface of airborne germs, they immediately produce radical hydroxyl (OH.) as an active species, which robs the germ cells of hydrogen and thereby kills them. This chemical reaction is an oxidation reaction, and the radial hydroxyl (OH.) achieves not only sterilization but also deodorization by oxidizing various airborne molecules that produce odors.

Now, how efficiently the air purifier 300 of this embodiment kills airborne germs will be described in terms of a practical example. It is to be understood, however, that the air purifier 300 of this embodiment is not limited to the example specifically described below, but may be implemented with modifications made in operating conditions and other factors as required.

Example 3

The air purifier 300 incorporating the ion generating device 1 used in Example 1 described earlier was installed in a test space 2.0 m long, 2.5 m wide, and 2.7 m high. Then, common bacteria and fungi that had been cultured on a culture medium beforehand were sprayed in the test space. Simultaneously, the ion generating device 1 was put into operation under the same conditions as in Example 1 described earlier, and the blowing fan 302 was started, so that the air purifier 300 started operating.

Then, at predetermined time intervals, using an air sampler, model RCS manufactured by Biotest AG, Germany, the air inside the test space was extracted at a rate of 40 L/min and sampled for four minutes to measure the number of germs contained in the air. The results are shown in Table 1.

In three hours after the air purifier 300 started operating, of the common bacteria and fungi that had originally been present in the test space, 72% and 75%, respectively, were removed. This proves that the air purifier 300 of this embodiment, incorporating the ion generating device 1, is capable of satisfactorily killing most airborne germs by the action of the negative and positive ions that it blows out.

Figure 4:
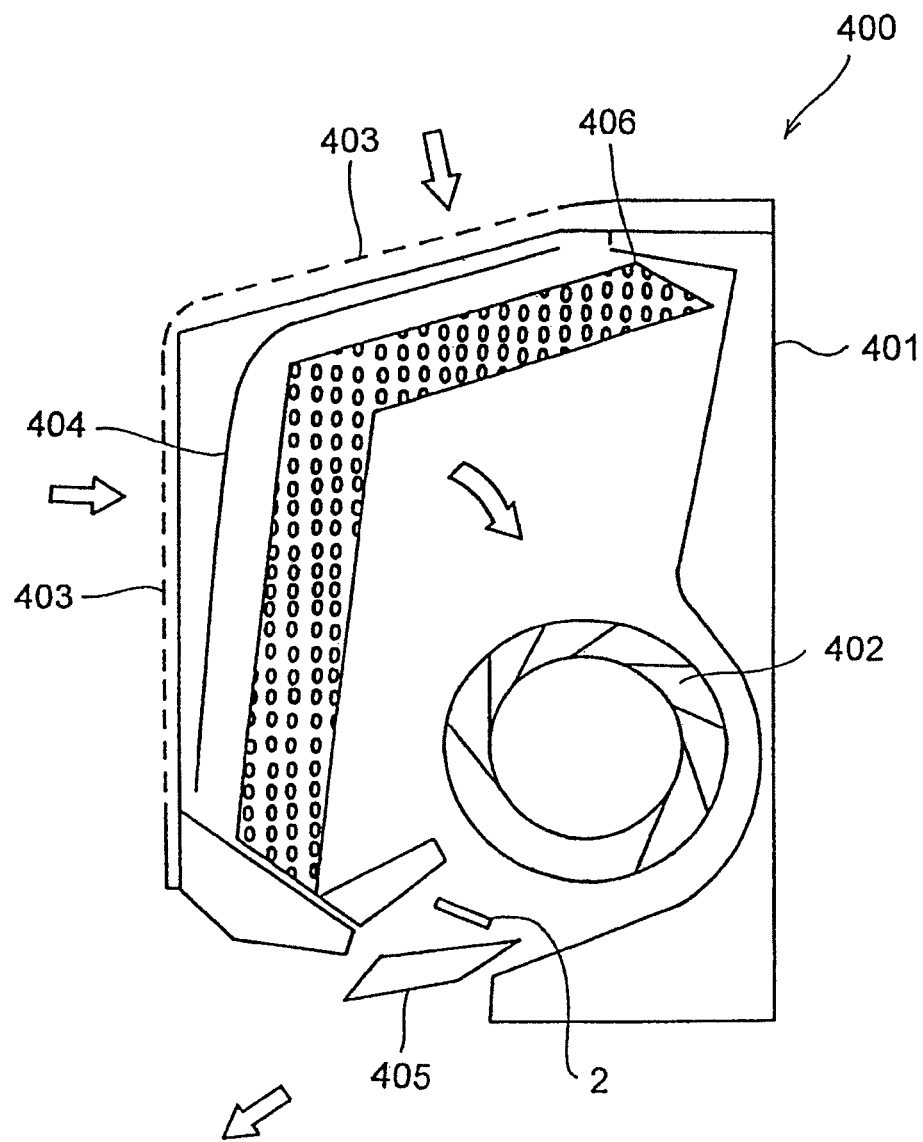
FIG. 4 is a sectional view showing an outline of the structure of the air conditioner, incorporating an ion generating device, of a third embodiment of the invention.

Next, a third embodiment of the invention will be described with reference to the drawings. FIG. 4 is a sectional view showing an outline of the structure of the air conditioner 400, incorporating an ion generating device 1, of a third embodiment of the invention.

In a rear portion inside the body 401 of the air conditioner 400, a blowing fan 402 is provided. In the front and top faces of the body 401, an air inlet 403 is formed that consists of a number of holes or slits. On the downstream side of the inlet 403, various filters 404 for dust removal and deodorization are provided. On the downstream side of the filters 404, a heat exchanger 406 is provided. Below the inlet 403 of the body 401, an air outlet 405 is formed that is provided with a louver for adjusting the direction of the air blown out. In this way, an air flow passage leading from the inlet 403 to the filters 404, then to the heat exchanger 406, and then to the outlet 405 is formed inside the body 401.

Moreover, the ion generating device 1 (see FIG. 1) of the first embodiment described earlier is arranged with its ion generating electrode member 2 placed in the air flow passage, in the vicinity of the outlet 405. Here, the high alternating-current voltage source 6 (see FIG. 1) may be provided separately from a power source for driving the blowing fan 402, or may be shared for this purpose also. In the latter case, a controller (not shown) is additionally provided so that the driving of the blowing fan 402 and of a compressor (not shown) and the operation of the ion generating device 1 can be controlled independently. This permits the ion generating device 1 to be turned on and off as required while the air conditioner 400 is operating, and thus enhances the usability of the air conditioner 400.

When this air conditioner 400, structured as described above, starts operating, the blowing fan 402 starts rotating. As a result, the air sucked through the inlet 403 into the air flow passage is passed through the filters 404, which remove dust and odors from the air, is then passed through the heat exchanger 406, which exchanges heat between the air and a cooling medium, and is then blown out through the outlet 405. Meanwhile, if the ion generating device 1 is kept on, the negative and positive ions generated in the space around the ion generating electrode member 2 are blown out together with the clean air. In this way, it is possible to kill airborne germs by the action of negative and positive ions.

Now, how efficiently the air conditioner 400 of this embodiment kills airborne germs will be described in terms of a practical example. It is to be understood, however, that the air conditioner 400 of this embodiment is not limited to the example specifically described below, but may be implemented with modifications made in operating conditions and other factors as required.

Example 4

The air conditioner 400 incorporating the ion generating device 1 used in Example 1 described earlier was installed in a test space 2.0 m long, 2.5 m wide, and 2.7 m high. Then, common bacteria and fungi that had been cultured on a culture medium beforehand were sprayed in the test space. Simultaneously, the ion generating device 1 was put into operation under the same conditions as in Example 1 described earlier, and the blowing fan 402 was started, so that the air conditioner 400 started operating.

Then, at predetermined time intervals, using an air sampler, model RCS manufactured by Biotest AG, Germany, the air inside the test space was extracted at a rate of 40 L/min and sampled for four minutes to measure the number of germs contained in the air. The results are shown in Table 2.

In three hours after the air conditioner 400 started operating, of the common bacteria and fungi that had originally been present in the test space, 75% and 78%, respectively, were removed. This proves that the air conditioner 400 of this embodiment, incorporating the ion generating device 1, is capable of satisfactorily killing most airborne germs by the action of the negative and positive ions that it blows out.

Figure 5:
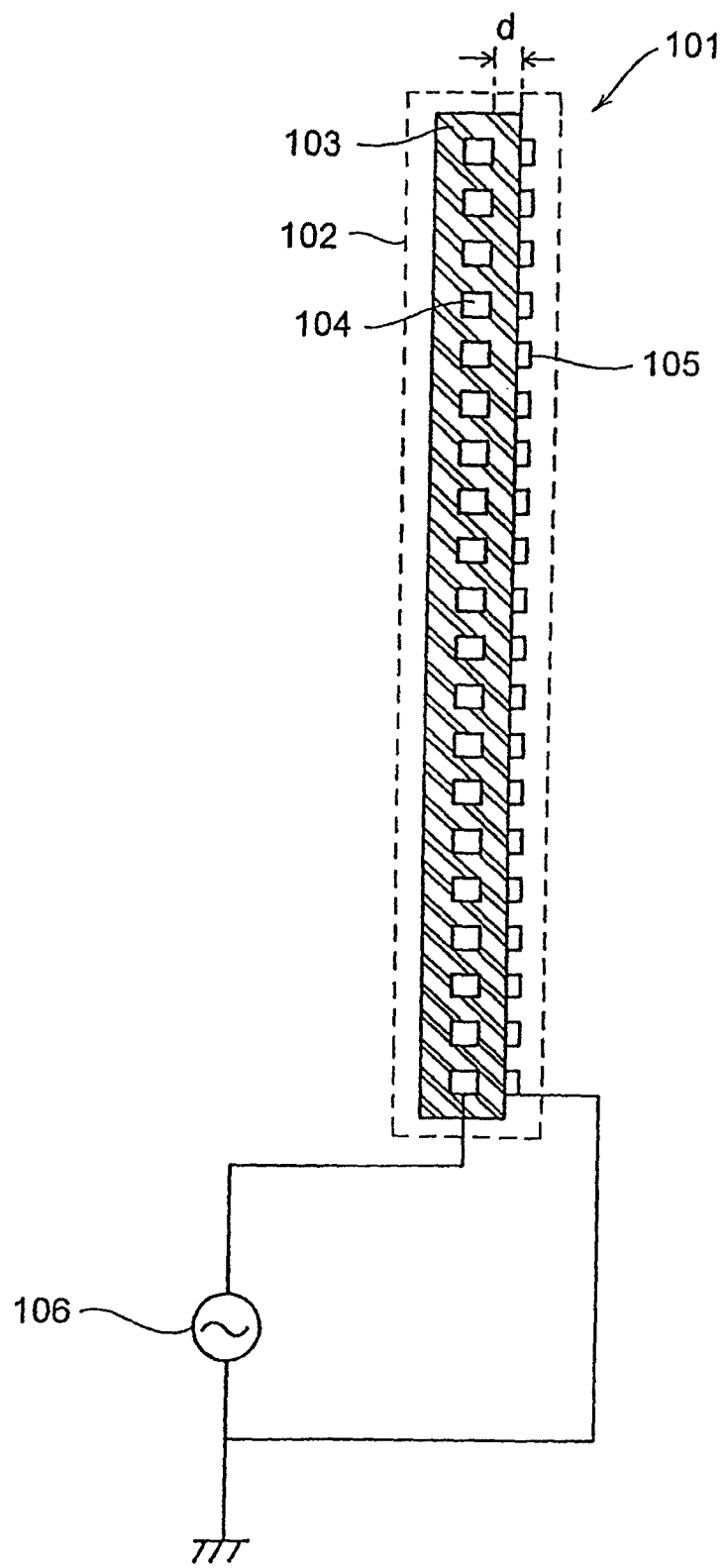
FIG. 5 is a sectional view showing an outline of the structure of the ion generating device 101 of a fourth embodiment of the invention.

Next, a fourth embodiment of the invention will be described with reference to the drawings. FIG. 5 is a sectional view showing an outline of the structure of the ion generating device 101 of a fourth embodiment of the invention.

As shown in FIG. 5, the ion generating device 101 of this embodiment is composed of an ion generating electrode member 102 having a first electrode 104 and a second electrode 105 arranged so as to face each other, and a high alternating-current voltage source 106 connected to the first and second electrodes 104 and 105 in such a way that the first electrode 104 serves as a voltage application electrode and the second electrode 105 serves as a grounding electrode.

As shown in FIG. 5, the ion generating electrode member 102 has the first electrode 104 embedded in a flat-plate-shaped glass plate 103, which acts as a dielectric, and has the second electrode 105 kept in intimate contact with one side of the glass plate 103.

In the ion generating electrode member 102 shown in FIG. 5, a glass plate 103 is used as a dielectric; however, any other insulating material formed into any other shape may be used instead according to the shape and structure of the apparatus in which the ion generating device 101 is incorporated.

As the glass plate 103, for example, a flat plate made of Pyrex glass is used. As the first and second electrodes 104 and 105, for example, wire meshes produced by plain-weaving wire of stainless steel 316 or 304 are used.

The first electrode 104 can be embedded in the glass plate 103 by a known process. For example, this can easily be achieved by dipping and positioning the first electrode 104 in molten glass poured into a casting mold for molding the glass into a flat plate of predetermined size, and then cooling and thereby solidifying the glass.

For enhanced ion generation efficiency, the second electrode 105 is kept in intimate contact with the glass plate 103. The second electrode 105 can easily be put into intimate contact with the glass plate 103 by bonding, by press-fitting with pieces of wire wound around, by screen printing, or by any other known process.

Now, how the ion generating device 101 structured as described above operates will be described in terms of a practical example. It is to be understood, however, that the ion generating device 101 of this embodiment is not limited to the example specifically described below, but may be implemented with modifications made in operating conditions and other factors as required.

Example 5

As the glass plate 103, a flat plate of Pyrex glass, 35 mm×35 mm and 3.0 mm thick, was used. As the first and second electrodes 104 and 105, wire meshes, each 33 mm×33 mm and having 48 meshes/inch, produced by plain-weaving wire of stainless steel 304, 0.23 mm across, were used. Between the first and second electrodes 104 and 105 arranged so as to face each other, a gap (indicated by "d" in FIG. 5) of 1.0 mm was secured.

By activating the high alternating-current voltage source 106, an alternating-current voltage of 3.0 kV rms having a frequency of 20 kHz was applied to the first electrode 104, with the second electrode 105 at the ground potential. Then, using an airborne ion counter, model 83-1001B manufactured by Dan Kagaku Co., Ltd., Japan, the concentrations of negative and positive ions with mobility of 1 $cm^2/V \cdot sec$ or higher were measured at a measurement point located 10 cm away from the side of the glass plate 103 on which the first electrode 104 is arranged. The measurement showed the presence of about 50,000 ions/cc of negative and positive ions. The concentration of ozone was 0.05 ppm.

In this way, by operating the ion generating device 101 with a comparatively low alternating-current voltage of 3.0 kV rms applied, it is possible to generate a sufficient amount of negative and positive ions in the air. In the ion generating device 101 of this embodiment, the first electrode 104 is embedded in the glass plate 103, that is, the first electrode 104 is not exposed to the air. This prevents dust and other foreign particles from settling on and thereby contaminating the first electrode 104, and thus greatly saves trouble related to maintenance such as cleaning.

Figure 6:
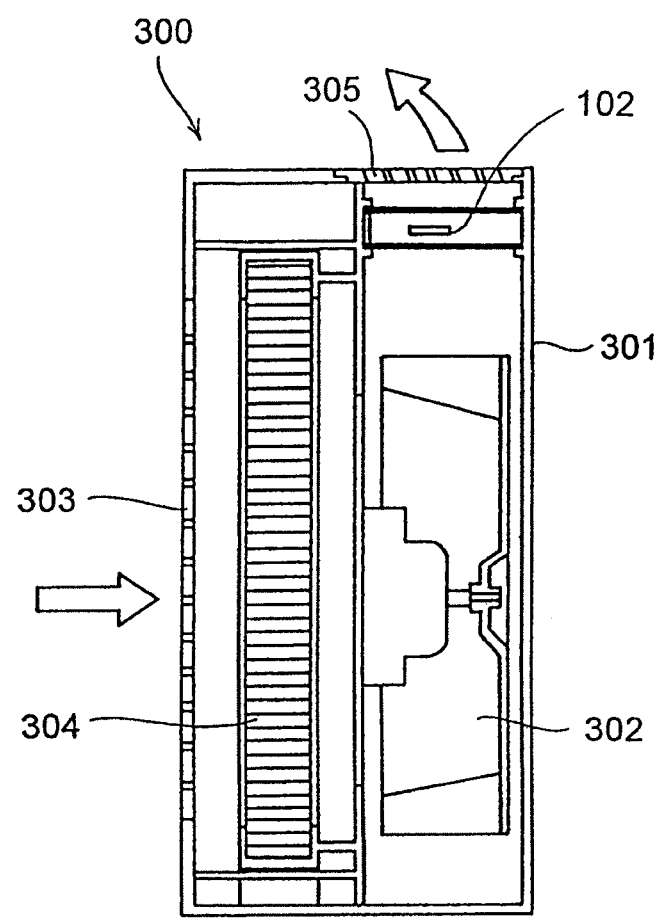
FIG. 6 is a sectional view showing an outline of the structure of the air purifier, incorporating an ion generating device, of a fifth embodiment of the invention.

Next, a fifth embodiment of the invention will be described with reference to the drawings. FIG. 6 is a sectional view showing an outline of the structure of the air purifier 300, incorporating an ion generating device 101, of a fifth embodiment of the invention. In a rear portion inside the body 301 of the air purifier 300, a blowing fan 302 is provided.

In the front face of the body 301, an air inlet 303 is formed that consists of a number of holes or slits. On the downstream side of the inlet 303, various filters 304 for dust removal and deodorization are provided. In the top face of the body 301, an air outlet 305 is formed that consists of a number of holes or slits. In this way, an air flow passage that leads from the inlet 303 to the filters 304 and then to the outlet 305 is formed inside the body 301.

Moreover, the ion generating device 101 (see FIG. 5) of the fourth embodiment described earlier is arranged with its ion generating electrode member 102 placed in the air flow passage, in the vicinity of the outlet 305. Here, the high alternating-current voltage source 106 (see FIG. 5) may be provided separately from a power source for driving the blowing fan 302, or may be shared for this purpose also. In the latter case, a controller (not shown) is additionally provided so that the driving of the blowing fan 302 and the operation of the ion generating device 101 can be controlled independently. This permits the ion generating device 101 to be turned on and off as required while the air purifier 300 is operating, and thus enhances the usability of the air purifier 300.

When this air purifier 300, structured as described above, starts operating, the blowing fan 302 starts rotating. As a result, the air sucked through the inlet 303 into the air flow passage is passed through the filters 304, which remove dust and odors from the air, and is then blown out through the outlet 305. Meanwhile, if the ion generating device 101 is kept on, the negative and positive ions generated in the space around the ion generating electrode member 102 are blown out together with the clean air. In this way, it is possible to kill airborne germs by the action of negative and positive ions.

Now, how efficiently the air purifier 300 of this embodiment kills airborne germs will be described in terms of a practical example. It is to be understood, however, that the air purifier 300 of this embodiment is not limited to the example specifically described below, but may be implemented with modifications made in operating conditions and other factors as required.

Example 6

The air purifier 300 incorporating the ion generating device 101 used in Example 5 described earlier was installed in a test space 2.0 m long, 2.5 m wide, and 2.7 m high. Then, common bacteria and fungi that had been cultured on a culture medium beforehand were sprayed in the test space. Simultaneously, the ion generating device 101 was put into operation under the same conditions as in Example 5 described earlier, and the blowing fan 302 was started, so that the air purifier 300 started operating.

Then, at predetermined time intervals, using an air sampler, model RCS manufactured by Biotest AG, Germany, the air inside the test space was extracted at a rate of 40 L/min and sampled for four minutes to measure the number of germs contained in the air. The results are shown in Table 3.

In three hours after the air purifier 300 started operating, of the common bacteria and fungi that had originally been present in the test space, 71% and 76%, respectively, were removed. This proves that the air purifier 300 of this embodiment, incorporating the ion generating device 101, is capable of satisfactorily killing most airborne germs by the action of the negative and positive ions that it blows out.

Figure 7:
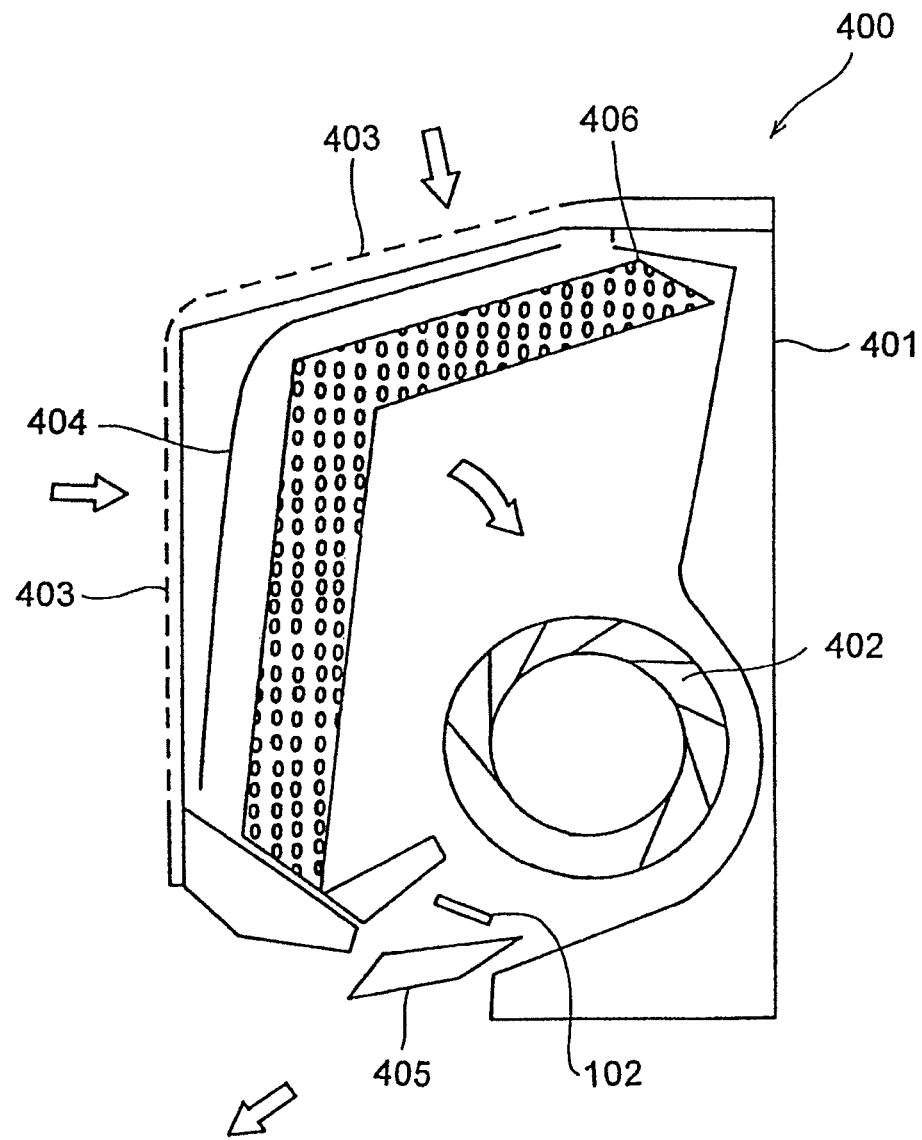
FIG. 7 is a sectional view showing an outline of the structure of the air conditioner, incorporating an ion generating device, of a sixth embodiment of the invention.

Next, a sixth embodiment of the invention will be described with reference to the drawings. FIG. 7 is a sectional view showing an outline of the structure of the air conditioner 400, incorporating an ion generating device 101, of a sixth embodiment of the invention.

In a rear portion inside the body 401 of the air conditioner 400, a blowing fan 402 is provided. In the front and top faces of the body 401, an air inlet 403 is formed that consists of a number of holes or slits. On the downstream side of the inlet 403, various filters 404 for dust removal and deodorization are provided. On the downstream side of the filters 404, a heat exchanger 406 is provided. Below the inlet 403 of the body 401, an air outlet 405 is formed that is provided with a louver for adjusting the direction of the air blown out. In this way, an air flow passage leading from the inlet 403 to the filters 404, then to the heat exchanger 406, and then to the outlet 405 is formed inside the body 401.

Moreover, the ion generating device 101 (see FIG. 5) of the fourth embodiment described earlier is arranged with its ion generating electrode member 102 placed in the air flow passage, in the vicinity of the outlet 405. Here, the high alternating-current voltage source 106 (see FIG. 5) may be provided separately from a power source for driving the blowing fan 402, or may be shared for this purpose also. In the latter case, a controller (not shown) is additionally provided so that the driving of the blowing fan 402 and of a compressor (not shown) and the operation of the ion generating device 101 can be controlled independently. This permits the ion generating device 101 to be turned on and off as required while the air conditioner 400 is operating, and thus enhances the usability of the air conditioner 400.

When this air conditioner 400, structured as described above, starts operating, the blowing fan 402 starts rotating. As a result, the air sucked through the inlet 403 into the air flow passage is passed through the filters 404, which remove dust and odors from the air, is then passed through the heat exchanger 406, which exchanges heat between the air and a cooling medium, and is then blown out through the outlet 405. Meanwhile, if the ion generating device 101 is kept on, the negative and positive ions generated in the space around the ion generating electrode member 102 are blown out together with the clean air. In this way, it is possible to kill airborne germs by the action of negative and positive ions.

Now, how efficiently the air conditioner 400 of this embodiment kills airborne germs will be described in terms of a practical example. It is to be understood, however, that the air conditioner 400 of this embodiment is not limited to the example specifically described below, but may be implemented with modifications made in operating conditions and other factors as required.

Example 7

The air conditioner 400 incorporating the ion generating device 101 used in Example 5 described earlier was installed in a test space 2.0 m long, 2.5 m wide, and 2.7 m high. Then, common bacteria and fungi that had been cultured on a culture medium beforehand were sprayed in the test space. Simultaneously, the ion generating device 101 was put into operation under the same conditions as in Example 5 described earlier, and the blowing fan 402 was started, so that the air conditioner 400 started operating.

Then, at predetermined time intervals, using an air sampler, model RCS manufactured by Biotest AG, Germany, the air inside the test space was extracted at a rate of 40 L/min and sampled for four minutes to measure the number of germs contained in the air. The results are shown in Table 4.

In three hours after the air conditioner 400 started operating, of the common bacteria and fungi that had originally been present in the test space, 74% and 78%, respectively, were removed. This proves that the air conditioner 400 of this embodiment, incorporating the ion generating device 101, is capable of satisfactorily killing most airborne germs by the action of the negative and positive ions that it blows out.

In all the embodiments described thus far, the dielectric used in the ion generating electrode member of the ion generating device is shaped like a flat plate. However, when the ion generating device is mounted in an air conditioning apparatus, as is usually the case, it is essential that the dialectic have a sufficient surface area and simultaneously that the ion generating electrode member occupy as less space as possible. In the process of finding a way to achieve an optimum balance between these conflicting requirements, the inventors of the present invention conceived the idea of making the dielectric cylindrical, which is reflected in the following embodiments.

Figure 8:
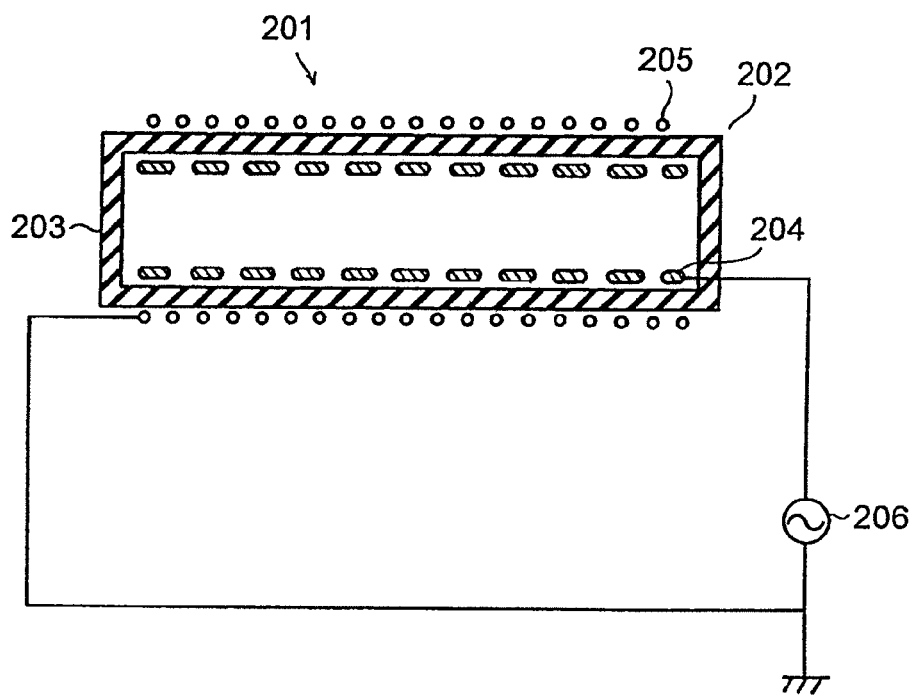
FIG. 8 is a diagram showing an outline of the structure of the ion generating device of a seventh embodiment of the invention.
Figure 9:
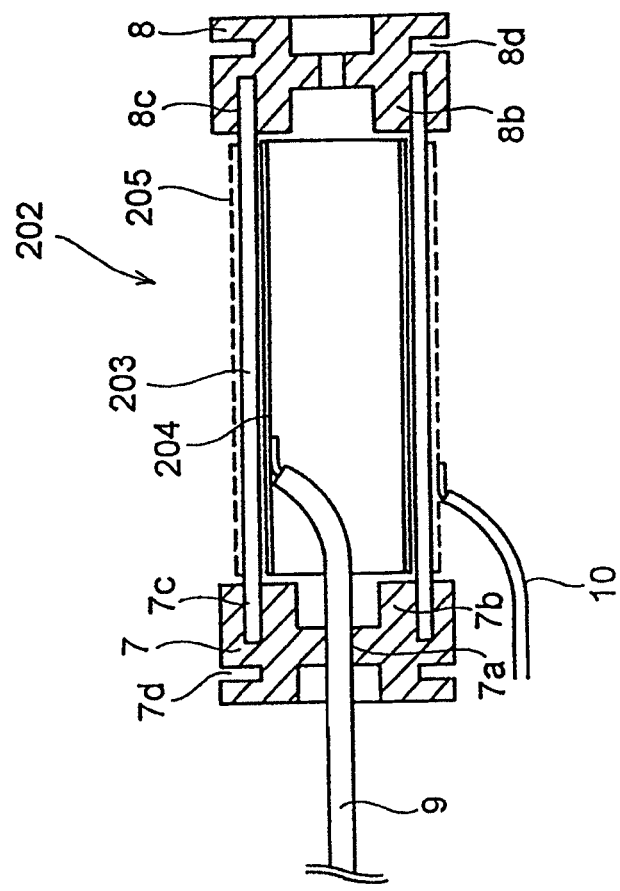
FIG. 9 is a sectional view of the ion generating electrode member used in the ion generating device.

Now, a seventh embodiment of the invention will be described with reference to the drawings. FIG. 8 is a diagram showing an outline of the structure of the ion generating device 201 of a seventh embodiment of the invention. FIG. 9 is a sectional view of the ion generating electrode member 202 used in this ion generating device 201.

As shown in FIG. 8, the ion generating device 201 of this embodiment is composed of an ion generating electrode member 202 having an inner electrode 204 and an outer electrode 205 arranged so as to face each other with a cylindrical glass tube 203, acting as a dielectric, disposed in between, and a high alternating-current voltage source 206 connected to the inner and outer electrodes 204 and 205 in such a way that the inner electrode 204 serves as a voltage application electrode and the outer electrode 205 serves as a grounding electrode. Here, the outer electrode 205 is used as a grounding electrode to prevent the user from receiving an electric shock when he or she accidentally touches the ion generating electrode member 202.

As shown in FIG. 9, the ion generating electrode member 202 has the inner electrode 204 kept in intimate contact with the inner surface of the cylindrical glass tube 203, has the outer electrode 205 kept in intimate contact with the outer surface of the glass tube 203, and has a pair of stopping members 7 and 8 fitted at both ends of the glass tube 203.

In the ion generating electrode member 202 shown in FIG. 9, a glass plate 203 is used as a dielectric; however, any other insulating material formed into any other shape may be used instead according to the shape and structure of the apparatus in which the ion generating device 201 is incorporated.

As the glass tube 203, for example, a cylindrical tube made of Pyrex glass is used. As the inner and outer electrodes 204 and 205, for example, wire meshes produced by plain-weaving wire of stainless steel 316 or 304 are used.

For enhanced ion generation efficiency, the inner and outer electrodes 204 and 205 are kept in intimate contact with the glass tube 203. The inner and outer electrodes 204 and 205 can easily be put into intimate contact with the glass tube 203 by a known process.

Figure 10:
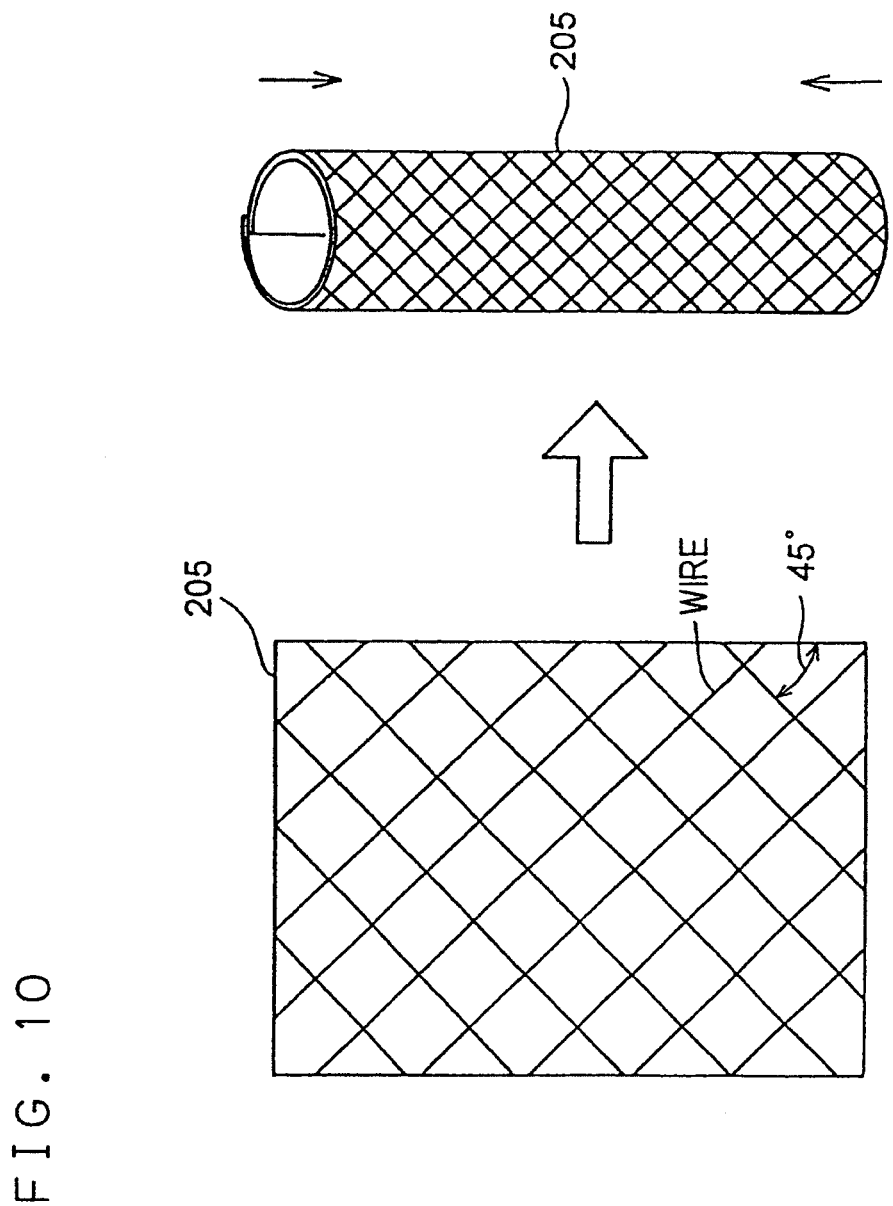
FIG. 10 is a perspective view illustrating an example of how the wire-mesh outer electrode is formed so as to be put in intimate contact with the outer surface of the glass tube of the ion generating electrode member.

The outer electrode 205 is put into intimate contact with the glass tube 203, for example, in the following manner. As shown in FIG. 10, a plain-woven wire mesh is rolled into a cylindrical shape in such a way that, when the cylinder is formed, the pieces of wire forming it form an angle of 45° to the axis of the cylinder. Then, opposite side edges of the wire mesh are welded together with an overlap. In this way, the outer electrode 205 is produced. Here, the outer electrode 205 is so formed as to have an internal diameter smaller than the external diameter of the glass tube 203.

Then, force is applied to both ends of the outer electrode 205 along its axis (i.e., in the figure, from above and from below) so that it is compressed axially. This causes the outer electrode 205 to expand radially, and, with the outer electrode 205 in this state, the glass tube 203 is inserted in it. When the force ceases to be applied, the outer electrode 205, tending to restore its original state, expands axially, and thus contracts radially. As a result, the outer electrode 205 is put into intimate contact with the glass tube 203.

Figure 11:
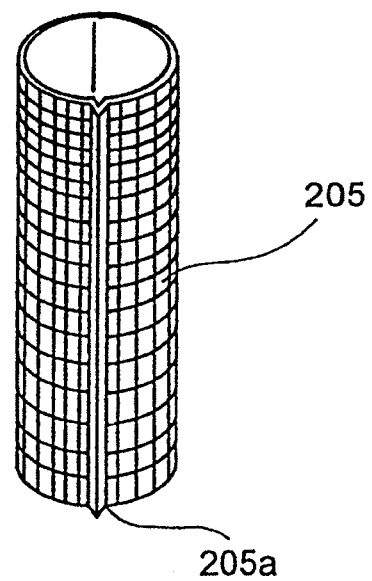
FIG. 11 is a perspective view illustrating another example of how the outer electrode is formed.

Another way to put the outer electrode 205 into intimate contact with the glass tube 203 is as follows. As shown in FIG. 11, part of the cylindrical outer electrode 205 is formed into a rib 205a that has an inverted-V-shaped cross section, extends along the axis of the outer electrode 205, and protrudes radially outward. Moreover, the outer electrode 205 is so formed as to have an internal diameter smaller than the external diameter of the glass tube 203. As the glass tube 203 is press-fitted into this outer electrode 205, the angle formed by the two faces of the inverted-V-shaped rib 205a becomes greater, and thereby makes the internal diameter of the outer electrode 205 greater. This permits the glass tube 203 to be inserted in the outer electrode 205. After the glass tube 203 is inserted in the outer electrode 205, the inverted-V-shaped rib 205a tends to restore its original state, and thereby puts the outer electrode 205 into intimate contact with the glass tube 203.

Figure 12:
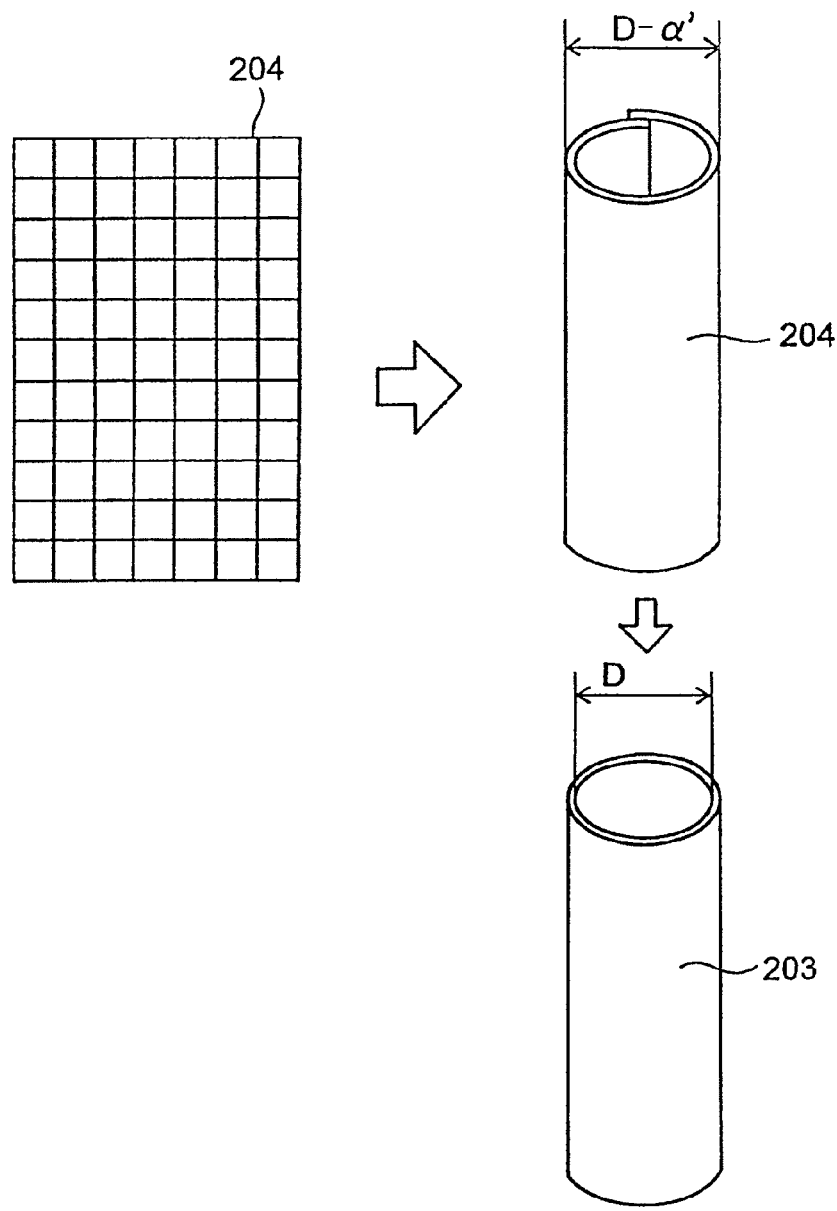
FIG. 12 is a perspective view illustrating an example of how the wire-mesh inner electrode is formed so as to be put in intimate contact with the inner surface of the glass tube of the ion generating electrode member.

On the other hand, the inner electrode 204 is put into intimate contact with the glass tube 203, for example, in the following manner. As shown in FIG. 12, a plain-woven wire mesh is rolled into a cylindrical shape to produce the inner electrode 204. Here, the inner electrode 204 is so formed as to have an external diameter larger than the internal diameter of the glass tube 203 and have opposite side edges left free, i.e. unwelded together. Then, force is applied at one side edge of the inner electrode 204 in an axial direction, as if to roll up the cylinder further, so that the internal diameter of the inner electrode 204, which is otherwise greater than the internal diameter (D) of the glass tube 203, becomes temporarily smaller (D−α') than it. With the inner electrode 204 in this state, it is inserted in the glass tube 203. After insertion, when the force ceases to be applied, the inner electrode 204 tends to restore its original state, and is thereby put into intimate contact with the inner surface of the glass tube 203.

Figure 13:
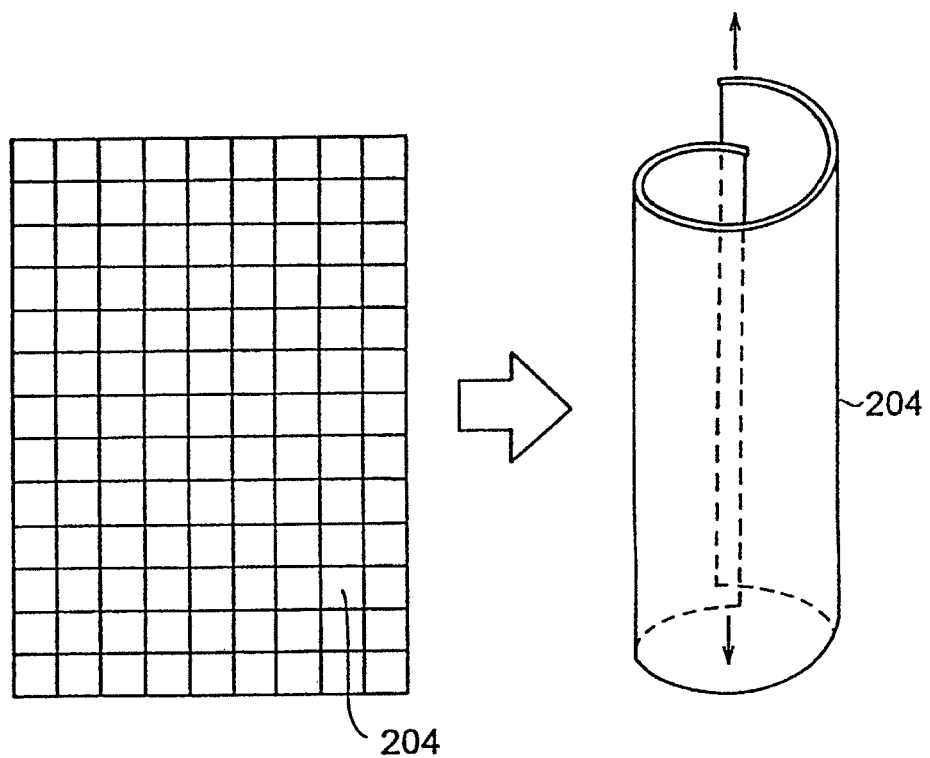
FIG. 13 is a perspective view illustrating another example of how the inner electrode is formed.

Another way to put the inner electrode 204 into intimate contact with the glass tube 203 is as follows. As shown in FIG. 13, a plain-woven wire mesh is rolled into a cylindrical shape to produce the inner electrode 204. Here, the inner electrode 204 is so formed as to have an external diameter greater than the internal diameter of the glass tube 203 and have opposite side edges left free, i.e. unwelded together. Then, one side edge of the inner electrode 204 is pulled along the axis thereof in such a way that the inner electrode 204 is expanded axially as it is twisted. This makes the external diameter of the inner electrode 204 smaller, and thereby permits it to be inserted in the glass tube 203. After insertion, when the pulling force ceases to be applied, the inner electrode 204 tends to restore its original state, and is thereby, with its external diameter increased, put into intimate contact with the glass tube 203.

In FIG. 9, each of the stopping members 7 and 8 is disk-shaped, and has a peripheral projection 7b or 8b formed in a peripheral portion of one end surface thereof, with a peripheral groove 7c or 8c formed along the peripheral projection 7b or 8b, in a middle portion thereof, so as to permit an end of the glass tube 203 to be fitted into it. Moreover, each of the stopping members 7 and 8 has a side groove 7d or 8d formed in the side surface thereof so as to permit the ion generating electrode member 202 as a whole to be held in position. In the center of the stopping member 7 is formed a hole 7a having a thin film formed therein. This thin film is so processed as to be easily broken when a lead 9 connected to the inner electrode 204 is laid therethrough.

Figure 14:
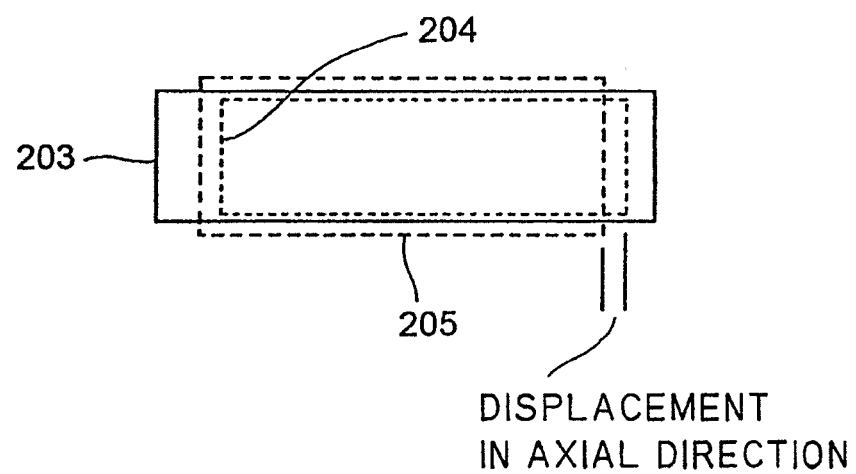
FIG. 14 is a plan view illustrating a displacement between the inner and outer electrodes that are arranged so as to face each other with the glass tube disposed in between in the ion generating electrode member.

The preferred depth of the peripheral grooves 7c and 8c formed in the stopping members 7 and 8 is such that, as long as the ends of the glass tube 203 are kept in contact with the bottoms of the peripheral grooves 7c and 8c, the inner and outer electrodes 204 and 205 do not move relative to each other. If the inner and outer electrodes 204 and 205 move relative to each other, there occurs a loss in the capacitance that appears when a voltage is applied between them. Table 5 shows the relationship, as actually observed, between the change in the positions of the electrodes relative to each other and the loss in capacitance. Here, as shown in FIG. 14, only movement, or displacement, of the electrodes relative to each other along the axis of the glass tube 203 is considered.

As Table 5 shows, as long as the inner and outer electrodes 204 and 205 remained in position, the capacitance was 38.8 pF; when the electrodes 204 and 205 were displaced 5 mm relative to each other, the capacitance was 36.2 pF, marking a 6.7% loss relative to the capacitance with no displacement. In the ion generating electrode member 202 of this embodiment, fitting the stopping members 7 and 8 at both ends of the glass tube 203 helps reduce the maximum displacement between the electrodes 204 and 205 to about 2 mm. This helps minimize the loss in capacitance.

The preferred width of the peripheral grooves 7c and 8c formed in the stopping members 7 and 8 is slightly smaller than the thickness of the glass tube 203. This permits the stopping members 7 and 8 to be fitted tightly to the glass tube 203.

The stopping members 7 and 8 may be made of any material, preferably an elastic material such as rubber so that the stopping members 7 and 8 can easily be fitted to the ends of the glass tube 203 and that the glass tube 203 can easily be stopped hermetically. Particularly preferred example of such an elastic material is ethylene-propylene rubber (EPDM), because it is resistant to ozone generated by the ion generating electrode member 202.

As the leads 9 and 10 connected to the inner and outer electrodes 204 and 205, leads of any known type may be used. A preferable example of such leads is stainless steel leads coated with a polyethylene fluoride resin, because they excel in resistance to ozone.

The ion generating electrode member 202 shown in FIG. 9 is assembled, for example, in the following manner. First, the inner electrode 204 having the lead 9 welded thereto beforehand is inserted in the glass tube 203. Then, while the lead 9 is being inserted, from the free end thereof, in the hole 7a of the stopping member 7, the stopping member 7 is fitted at one end of the glass tube 203. Next, the outer electrode 205 having the lead 10 welded thereto beforehand is fitted around the glass tube 203, and then the stopping member 8 is fitted at the other end of the glass tube 203.

Then, the high alternating-current voltage source 206 is connected by way of the lead 9 to the inner electrode 204, serving as a voltage application electrode, and by way of the lead 10 to the outer electrode 205, serving as a grounding electrode. In this way, the ion generating device 201 shown in FIG. 8 is assembled. Now, by activating the high alternating-current voltage source 206, it is possible to apply an alternating-current voltage to the inner electrode 204, with the outer electrode 205 at the ground potential.

Now, how the ion generating device 201 structured as described above operates will be described in terms of practical examples. It is to be understood, however, that the ion generating device 201 of this embodiment is not limited to any of the examples specifically described below, but may be implemented with modifications made in operating conditions and other factors as required.

First, to study the relationship between the voltage applied, as expressed in an rms value, and the amount of ions generated, the following experiment was conducted.

Example 8

As the glass tube 203, a cylindrical tube of Pyrex glass, having an external diameter of 10 mm, 1.3 mm thick, and 150 mm long, was used. As the inner electrode 204, a sheet of stainless steel 304, 0.08 mm thick and 80 mm long, was used, and, as the outer electrode 205, a wire mesh, 100 mm long and having 16 meshes/inch, produced by plain-weaving wire of stainless steel 304, 0.23 mm across, was used.

Figure 15:
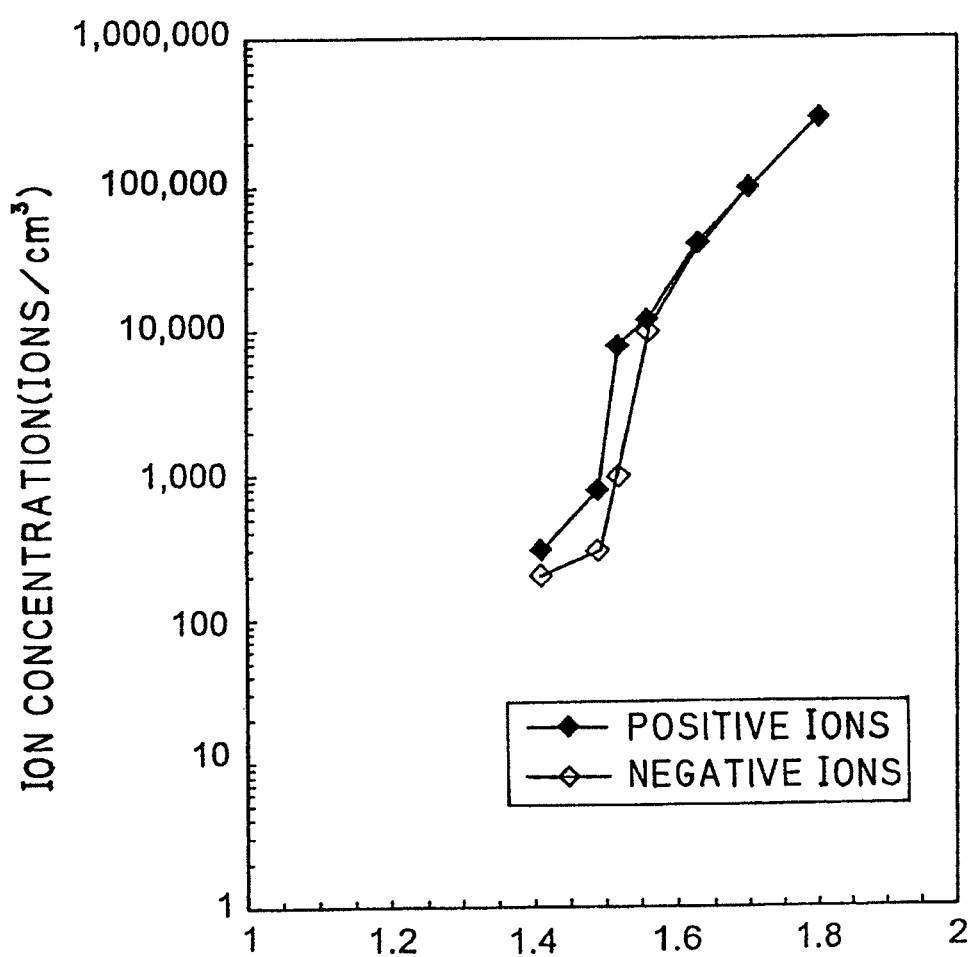
FIG. 15 is a graph showing the concentrations of negative and positive ions, as measured at a measurement point located 10 cm away from the side surface of the glass tube when an alternating-current voltage of 1.3 to 1.8 kV rms having a frequency of 22 kHz was applied to the inner electrode, with the outer electrode kept at the ground potential, in the ion generating device.

By activating the high alternating-current voltage source 206, an alternating-current voltage of 1.3 to 1.8 kV rms having a frequency of 22 kHz was applied to the inner electrode 204, with the outer electrode 205 at the ground potential. Then, using an airborne ion counter, model 83-1001B manufactured by Dan Kagaku Co., Ltd., Japan, the concentrations of negative and positive ions with mobility of 1 $cm^2$/V·sec or higher were measured at a measurement point located 10 cm away from the side surface of the glass tube 203. The results are shown in FIG. 15.

When the ion generating device 201 was kept inactive, i.e. when the voltage applied was 0 V, the concentrations of the negative and positive ions were both about 300 ions/cc. It was confirmed that, with a voltage of 1.52 kV or higher applied, the ion generating device 201 generated 10,000 or more ions and that, as the voltage, as expressed in an rms value, became higher, the ion concentration increased.

Next, to evaluate the survival rate of airborne germs against the concentration of ions, the following experiment was conducted.

Example 9

The ion generating device 201 of Example 8 described above was installed in a test space 2.0 m long, 2.5 m wide, and 2.7 m high. The atmosphere inside the test space was kept at a temperature of 25° C. and at a relative humidity of 42%. Then, colon bacilli that had been cultured on a culture medium beforehand were sprayed in the test space so that their concentration was 500 to 1,500 germs/cc. Simultaneously, the ion generating device 201 was put into operation, and the blowing fan 302 was started so that the air inside the test space was agitated at an air-flow rate of 4 $m^3$/min.

Figure 16:
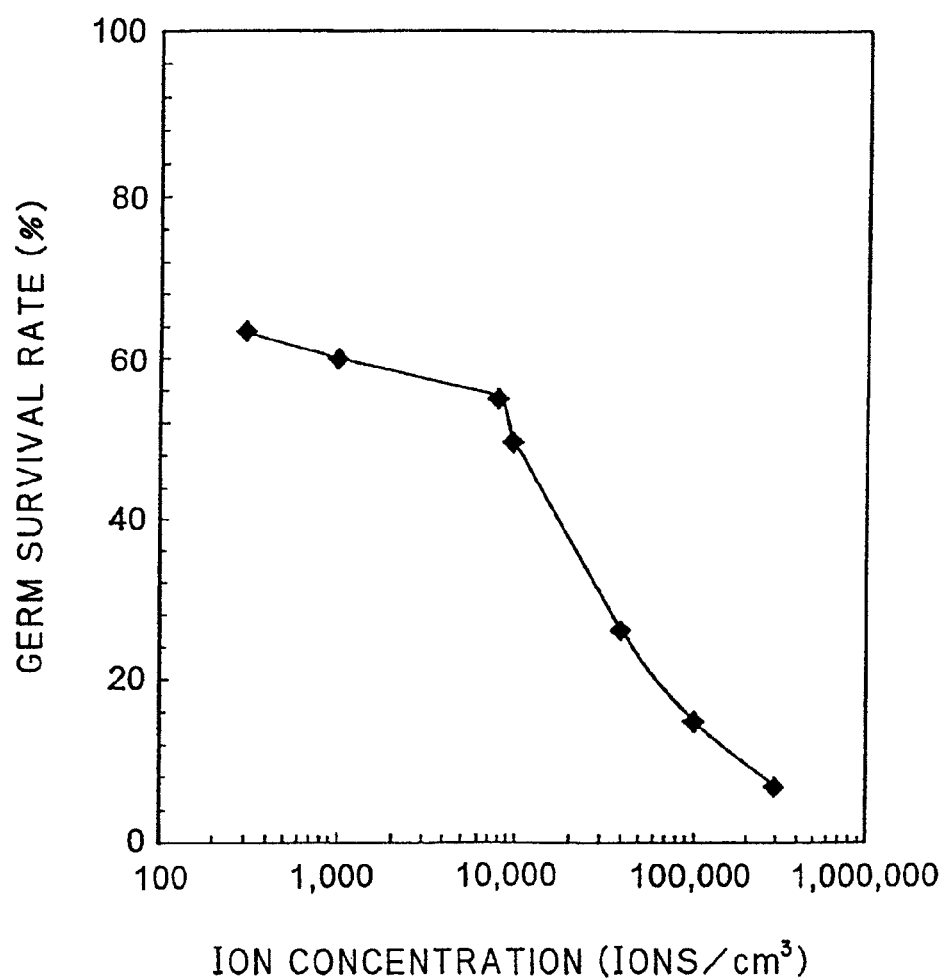
FIG. 16 is a graph showing the relationship between the concentrations of negative and positive ions, as measured at a measurement point located 10 cm away from the side surface of the glass tube, and the survival rate of colon bacilli after one hour when the ion generating device was installed in a test space 2.0 m long, 2.5 m wide, and 2.7 m high, then colon bacilli that had been cultured on a culture medium beforehand were sprayed in the test space so that their concentration was about 500 to 1,500 germs/cc, then the ion generating device was put into operation, and then the blowing fan was started so that the air inside the test space was agitated.

Then, using an airborne ion counter, model 83-1001B manufactured by Dan Kagaku Co., Ltd., Japan, the concentrations of negative and positive ions with mobility of 1 $cm^2$/V·sec or higher were measured at a measurement point located 10 cm away from the side surface of the glass tube 203. One hour after the ion generating device 201 started operating, using an air sampler, model RCS manufactured by Biotest AG, Germany, the air inside the test space was extracted at a rate of 40 L/min and sampled for four minutes to measure the number of colon bacilli contained in the air. The results are shown in FIG. 16.

With no ions generated, the survival rate of colon bacilli was 63.5% after one hour of natural decay. This means that, if an error of about 10% is taken into consideration, achieving a survival rate of 53.5% or lower in one hour would be regarded as achieving significant sterilization. As shown in FIG. 16, satisfactory sterilization was confirmed when the concentrations of the negative and positive ions were both 10,000 ions/cc or higher.

Figure 17:
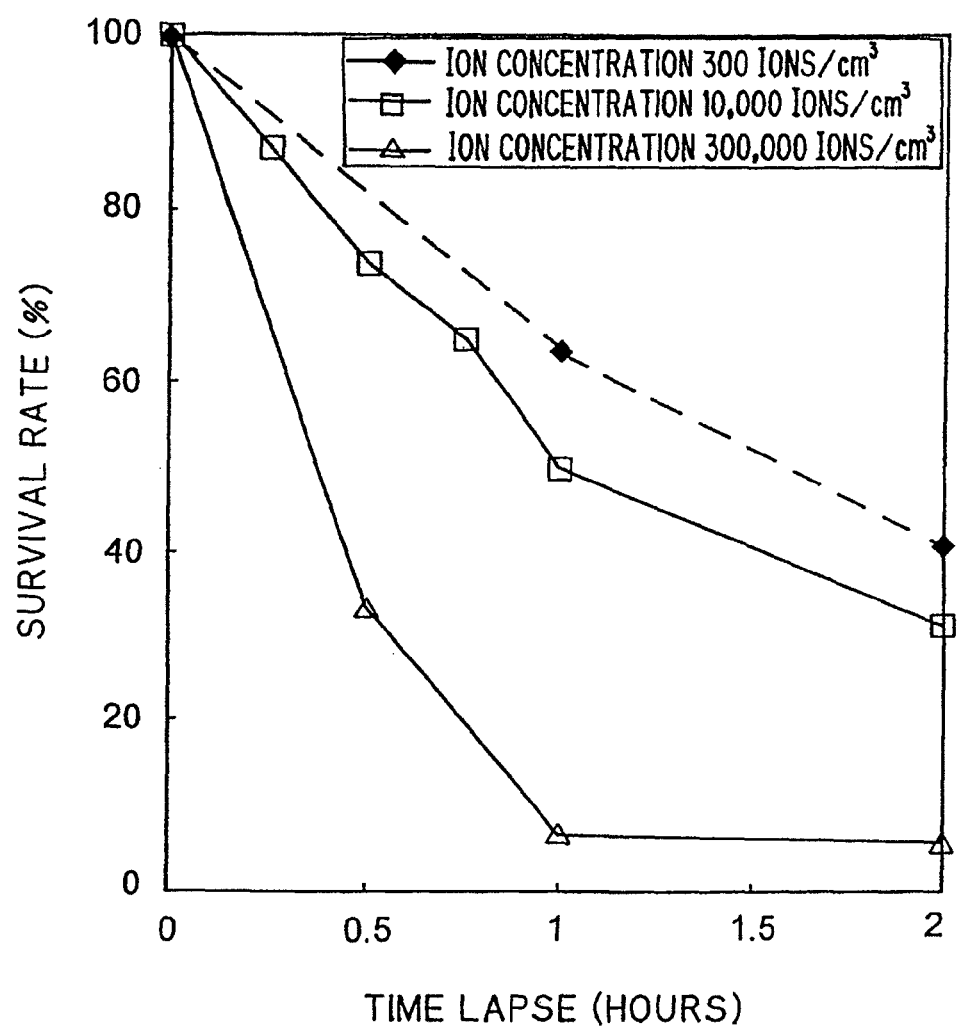
FIG. 17 is a graph showing the variation with time of the survival rate of colon bacilli at different ion concentrations.

FIG. 17 is a graph showing the variation with time of the survival rate of colon bacilli at different ion concentrations. This figure shows that, the higher the ion concentration, the more effectively airborne germs were killed and that, at an ion concentration of 300,000 ions/cc, most of the colon bacilli inside the test space were killed in one hour.

Next, to study the relationship between the voltage applied, as expressed in an rms value, its frequency, and the amounts of ions and ozone generated, the following experiment was conducted.

Example 10

As the glass tube 203, a cylindrical tube of Pyrex glass, having an internal diameter of 10 mm, 1.0 mm thick, and 100 mm long, was used. As the inner electrode 204, a wire mesh, 80 mm long and having 60 meshes/inch, produced by plain-weaving wire of stainless steel 304, 0.15 mm across, was used, and, as the outer electrode 205, a wire mesh, 80 mm long and having 30 meshes/inch, produced by plain-weaving wire of stainless steel 304, 0.22 mm across, was used.

By activating the high alternating-current voltage source 206, different alternating-current voltages having different frequencies were applied to the inner electrode 205, with the outer electrode 204 at the ground potential. Then, using an airborne ion counter, model 83-1001B manufactured by Dan Kagaku Co., Ltd., Japan, the concentrations of negative and positive ions with mobility of 1 $cm^2$/V·sec or higher were measured at a measurement point located 10 cm away from the side surface of the glass tube 203. Moreover, using a UV absorption type ozone monitor, model EG-2001 manufactured by Ebara Jitsugyo Co., Ltd., Japan, the concentration of ozone, which is generated as a byproduct when ions are generated, was measured as well. The results are shown in Table 6.

As shown in Table 6, when a voltage of 44V rms having a frequency of 25 kHz was applied, ions were detected only in trace amounts. By contrast, when the voltage was raised tenfold, i.e. to 440 V rms, the concentrations of negative and positive ions sharply rose to 4,966 ions/cc and 13,910 ions/cc, respectively. When the voltage was raised further to above 1.1 kV rms, at any frequency in the range from 60 Hz to 30 kHz, the presence of 10,000 ions/cc or more of negative and positive ions was confirmed. In particular, at frequencies of 20 kHz or higher, almost no annoying noise was heard while the ion generating device 201 was operating. In addition, the concentration of ozone generated was as low as below about 0.01 ppm.

This proves that, with the ion generating device 201 of this embodiment, by the application of a comparatively low alternating-current voltage of 1.1 to 2.0 kV rms having a frequency of 20 kHz or higher, i.e. beyond the range of human hearing, it is possible to generate 10,000 ions/cc or more of negative and positive ions, i.e. a sufficient amount of ions to achieve satisfactory sterilization, with minimum noise and with minimum generation, below a generally admitted level, of hazardous ozone.

Next, to study the relationship between the concentrations of the negative and positive ions generated by the ion generating device 201 and the distance from the point at which those ions are generated, the following experiment was conducted.

Example 11

As the glass tube 203, a cylindrical tube of Pyrex glass, having an internal diameter of 10 mm, 1.0 mm thick, and 100 mm long, was used. As the inner electrode 204, a wire mesh, 80 mm long and having 60 meshes/inch, produced by plain-weaving wire of stainless steel 304, 0.15 mm across, was used, and, as the outer electrode 205, a wire mesh, 80 mm long and having 30 meshes/inch, produced by plain-weaving wire of stainless steel 304, 0.22 mm across, was used.

Figure 18A:
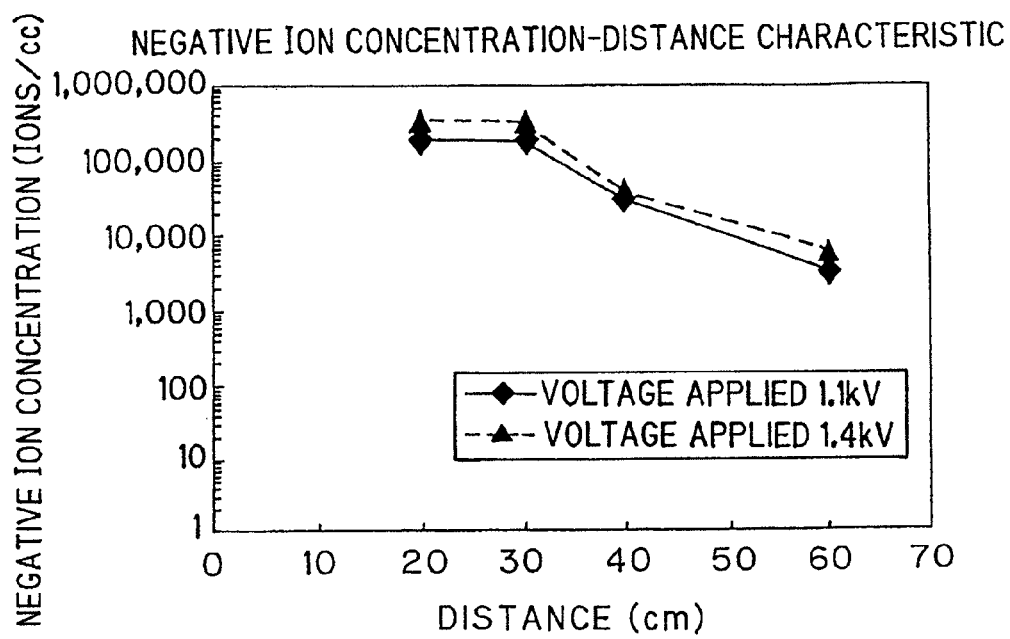
FIG. 18A is a graph showing the relationship between the concentration of negative ions generated and the distance from the side surface of the glass tube when an alternating-current voltage of 1.1 kV or 1.4 kV having a frequency of 15 kHz was applied to the inner electrode, with the outer electrode 205 kept at the ground potential, in the ion generating device, in which the glass tube was a cylindrical tube of Pyrex glass having an internal diameter of 10 mm, 1.0 mm thick, and 100 mm long, the inner electrode was a wire mesh, 80 mm long and having 60 meshes/inch, produced by plain-weaving wire of stainless steel 304, 0.15 mm across, and the outer electrode was a wire mesh, 80 mm long and having 30 meshes/inch, produced by plain-weaving wire of stainless steel 304, 0.22 across.
Figure 18B:
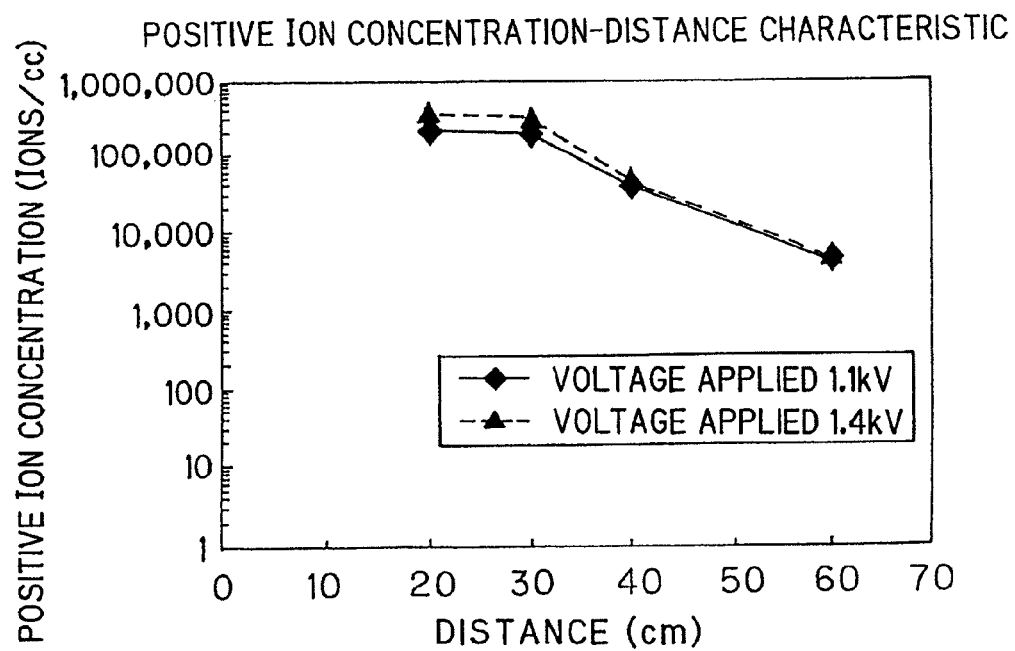
FIG. 18B is a graph showing the relationship between the concentration of positive ions generated and the distance from the side surface of the glass tube when the ion generating device was put into operation under the same conditions.

By activating the high alternating-current voltage source 206, an alternating-current voltage of 1.1 kV rms or 1.4 kV rms having a frequency of 15 kHz was applied to the inner electrode 204, with the outer electrode 205 at the ground potential. Then, using an airborne ion counter, model 83-1001B manufactured by Dan Kagaku Co., Ltd., Japan, the concentrations of negative and positive ions with mobility of 1 $cm^2$/V·sec or higher were measured at four measurement points located 20 cm, 30 cm, 40 cm, and 60 cm away from the side surface of the glass tube 203. The results in different cases are shown in FIGS. 18A and 18B.

As shown in these figures, with either of the alternating-current voltages of 1.1 kV rms and 1.4 kV rms, the farther from the side surface of the glass tube 203, the lower the concentration of negative and positive ions tend to become. At 20 cm from the side surface of the glass tube 203, the concentrations of negative and positive ions were both very high, specifically about 200,000 to 400,000 ions/cc. Thus, a sufficient amount of ions to kill and remove airborne germs satisfactorily was obtained. At any of the aforementioned measurement points, the concentration of ozone was as low as 0.01 to 0.25 ppm.

In this way, the higher the alternating-current voltage, as expressed in an rms value, that is applied to the ion generating electrode member 202, the larger the amount of negative and positive ions generated, and simultaneously the larger the amount of ozone generated. Since ozone is anything but essential to human health, it is necessary to minimize the amount of ozone generated.

First, the relationship between the meshes/inch number of the inner electrode 204 and the amounts of ions and of ozone generated was studied.

Example 12

Figure 19:
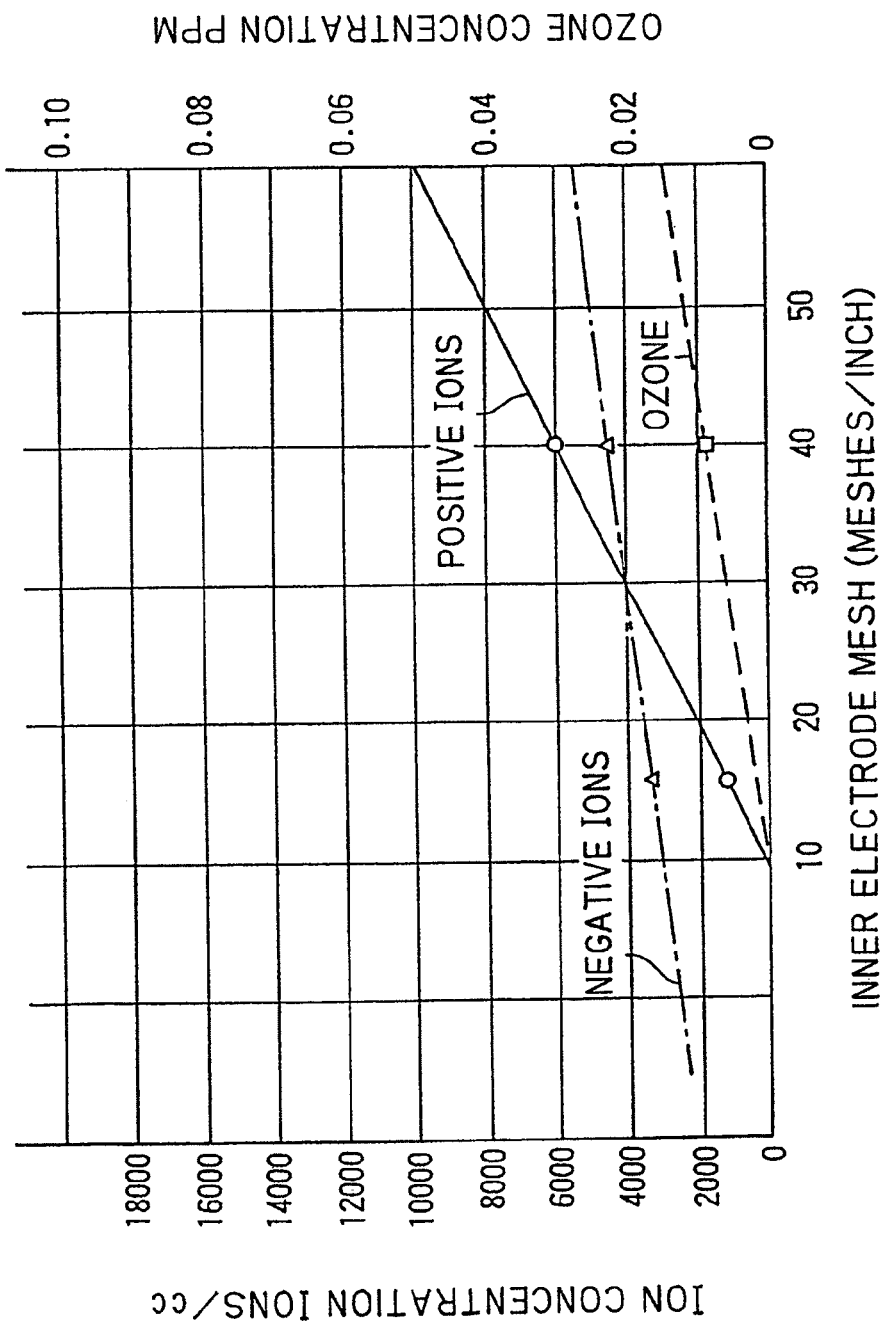
FIG. 19 is a graph showing the relationship between the meshes/inch number of the inner electrode and the amounts of negative and positive ions and of ozone generated, as measured at a measurement point located 10 cm away from the side surface of the glass tube when an alternating-current voltage of about 1.8 kV rms was applied to the ion generating electrode member in the ion generating device, in which the glass tube had an external diameter of 20 mm, was 63 mm long, and was 1.6 mm thick, the inner electrode was 60 mm long, and had a varying number of meshes/inch, and the outer electrode was woven from wire 0.4 mm across, was 60 mm long, and had 16 meshes/inch.

FIG. 19 is a graph showing the relationship between the meshes/inch number of the inner electrode 204 and the amounts of negative and positive ions and of ozone generated, as measured at a measurement point located 10 cm away from the side surface of the glass tube 203 when an alternating-current voltage of about 1.8 kV rms was applied to the ion generating electrode member 202, in which the glass tube 203 had an external diameter of 20 mm, was 63 mm long, and was 1.6 mm thick, the inner electrode 204 was 60 mm long, and had a varying number of meshes/inch, and the outer electrode 205 was woven from wire 0.4 mm across, was 60 mm long, and had 16 meshes/inch. Here, the wire diameter of the inner electrode 204 varied according to its meshes/inch number. The concentrations of ions and ozone were measured using, respectively, an airborne ion counter, model 83-1001B manufactured by Dan Kagaku Co., Ltd., Japan, and a UV absorption type ozone monitor, model EG-2001 manufactured by Ebara Jitsugyo Co., Ltd., Japan.

FIG. 19 shows that, the greater the meshes/inch number of the inner electrode 204 (i.e. the finer its meshes), the larger both the amounts of negative and positive ions and of ozone generated.

Next, the relationship between the meshes/inch number of the outer electrode 205 and the amounts of ions and of ozone generated was studied.

Example 13

Figure 20:
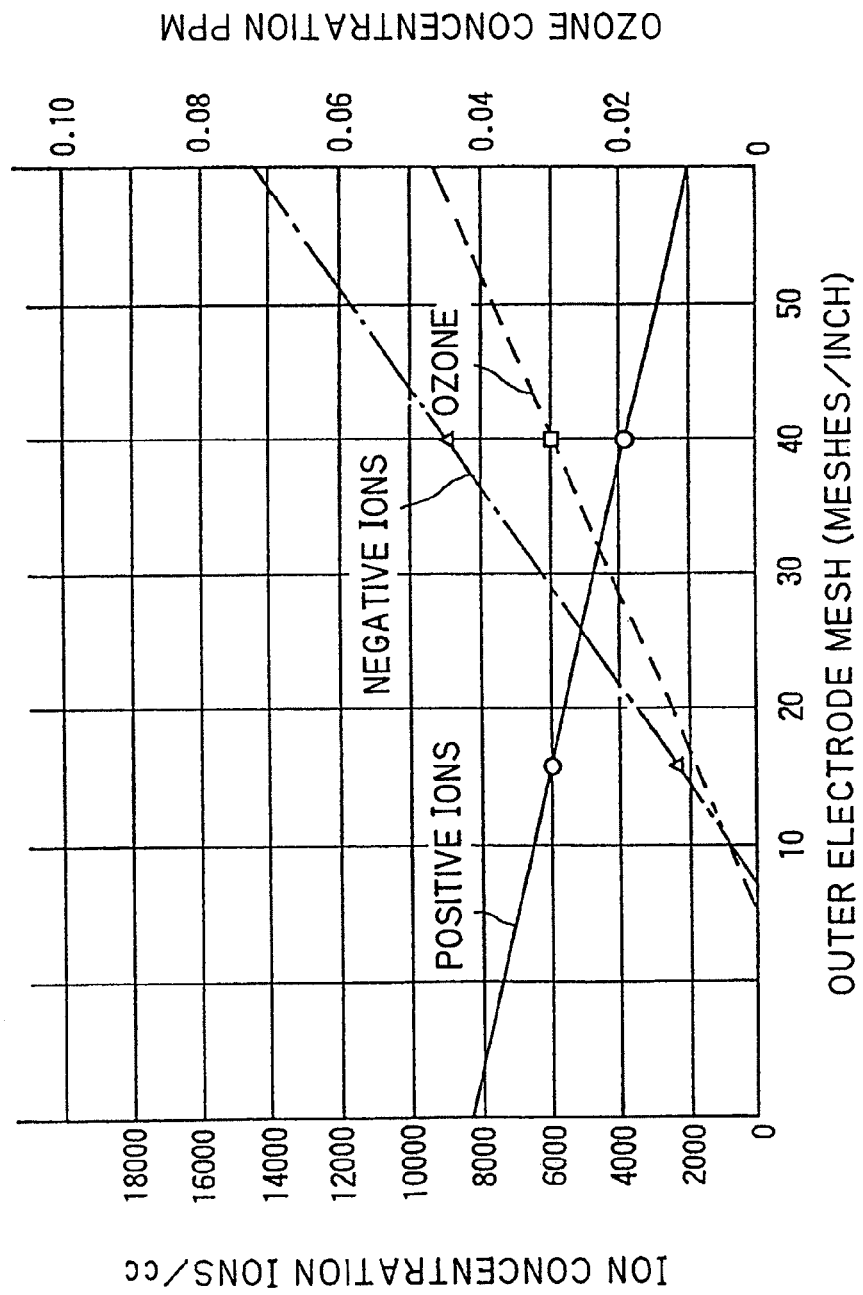
FIG. 20 is a graph showing the relationship between the meshes/inch number of the outer electrode and the amounts of negative and positive ions and of ozone generated, as measured at a measurement point located 10 cm away from the side surface of the glass tube when an alternating-current voltage of about 1.8 kV rms was applied to the ion generating electrode member in the ion generating device, in which the glass tube had an external diameter of 20 mm, was 63 mm long, and was 1.6 mm thick, the inner electrode was woven from wire 0.18 mm across, was 60 mm long, and had 40 meshes/inch, and the outer electrode was 60 mm long, and had a varying number of meshes/inch.

FIG. 20 is a graph showing the relationship between the meshes/inch number of the outer electrode 205 and the amounts of negative and positive ions and of ozone generated, as measured at a measurement point located 10 cm away from the side surface of the glass tube 203 when an alternating-current voltage of about 1.8 kV rms was applied to the ion generating electrode member 202, in which the glass tube 203 had an external diameter of 20 mm, was 63 mm long, and was 1.6 mm thick, the inner electrode 204 was woven from wire 0.18 mm across, was 60 mm long, and had 40 meshes/inch, and the outer electrode 205 was 60 mm long, and had a varying number of meshes/inch. Here, the wire diameter of the outer electrode 205 varied according to its meshes/inch number. The concentrations of ions and ozone were measured using, respectively, an airborne ion counter, model 83-1001B manufactured by Dan Kagaku Co., Ltd., Japan, and a UV absorption type ozone monitor, model EG-2001 manufactured by Ebara Jitsugyo Co., Ltd., Japan.

FIG. 20 shows that, the greater the meshes/inch number of the outer electrode 205, the larger the amounts of negative ions and of ozone generated, but the smaller the amount of positive ions.

Accordingly, by making the meshes of the inner electrode 204 finer and making the meshes of the outer electrode 205 coarser, it is possible to generate negative and positive ions efficiently while minimizing the generation of ozone.

In arrangements where the glass tube 203 is cylindrical in shape, the greater its external diameter, and the smaller its thickness, the larger its capacitance. The larger the capacitance of the glass tube 203, the easier it is to generate ions. Therefore, if only efficient generation of ions is considered, the glass tube 203 should be made as large in external diameter and as thin as possible. However, as the glass tube 203 is made larger in external diameter, not only the amount of ions generated, but also the amount of ozone generated increases. Thus, next, how to increase the amount of ions while minimizing the amount of ozone was examined.

Example 14

Figure 21:
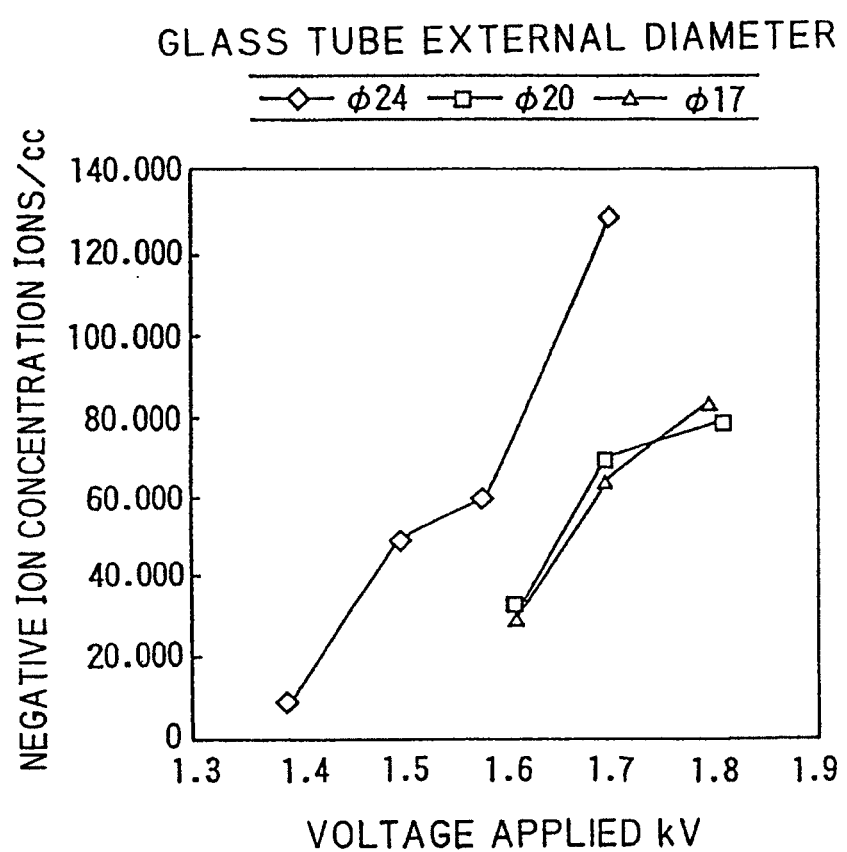
FIG. 21 is a graph showing the relationship between the voltage applied, as expressed in an rms value, and the concentration of negative ions, as measured at a measurement point located 10 cm away from the side surface of the glass tube when the inner electrode was woven from wire 0.18 mm across, was 60 mm long, and had 40 meshes/inch, the outer electrode was woven from wire 0.4 mm across, was 60 mm long, and had 16 meshes/inch, and the glass tube was 63 mm long, was 1.2 mm thick, and had a varying external diameter, specifically 17 mm, 20 mm, or 24 mm in the ion generating device.
Figure 22:
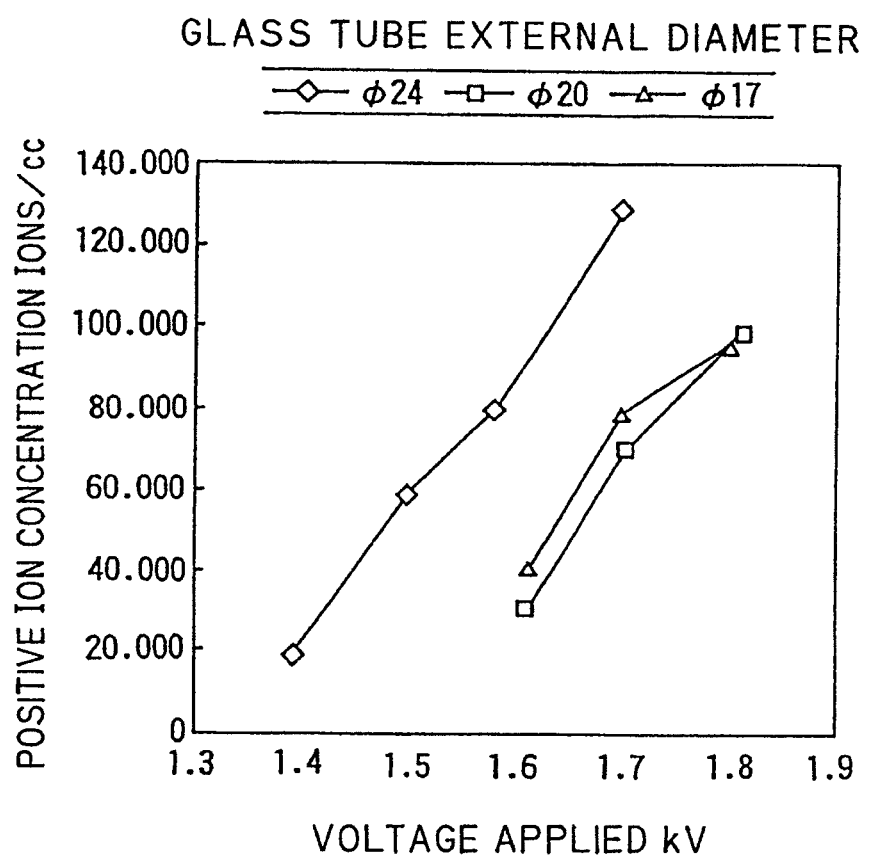
FIG. 22 is a graph showing the relationship between the voltage applied, as expressed in an rms value, and the concentration of positive ions, as measured at a measurement point located 10 cm away from the side surface of the glass tube when the ion generating device was put into operation under the same conditions.
Figure 23:
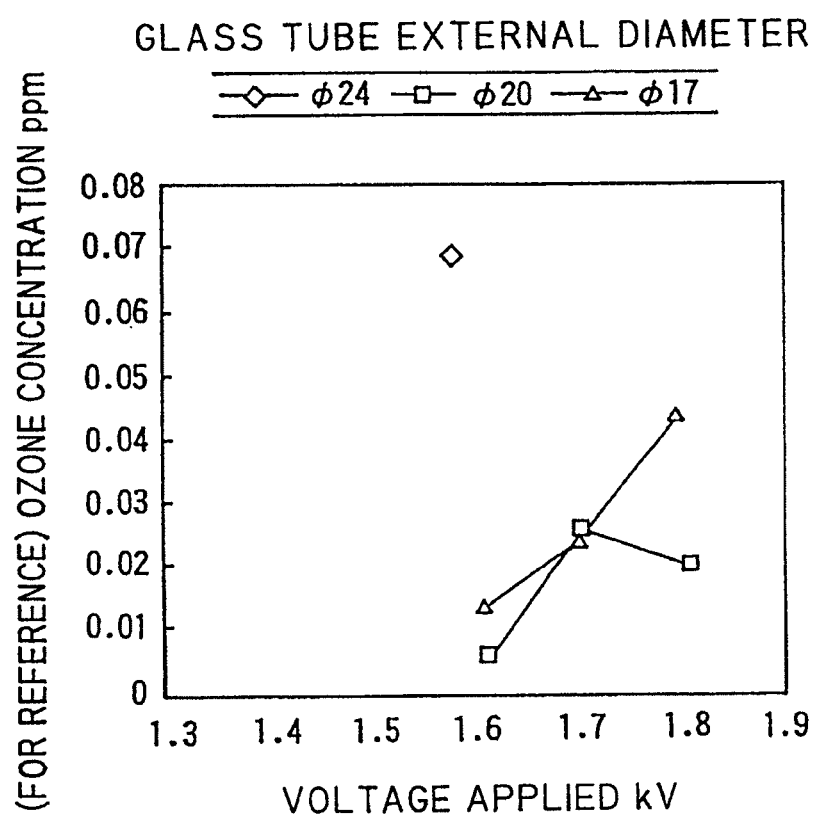
FIG. 23 is a graph showing the relationship between the voltage applied, as expressed in an rms value, and the concentration of ozone, as measured at a measurement point located 10 cm away from the side surface of the glass tube when the ion generating device was put into operation under the same conditions.

FIGS. 21 to 23 show the relationship between the voltage applied, as expressed in an rms value, and the concentrations of negative and positive ions and of ozone, as measured at a measurement point located 10 cm away from the side surface of the glass tube 203 when the inner electrode 204 was woven from wire 0.18 mm across, was 60 mm long, and had 40 meshes/inch, the outer electrode 205 was woven from wire 0.4 mm across, was 60 mm long, and had 16 meshes/inch, and the glass tube 203 was 63 mm long, 1.2 mm thick, and had a varying external diameter, specifically 17 mm, 20 mm, or 24 mm. The concentrations of ions and ozone were measured using, respectively, an airborne ion counter, model 83-1001B manufactured by Dan Kagaku Co., Ltd., Japan, and a UV absorption type ozone monitor, model EG-2001 manufactured by Ebara Jitsugyo Co., Ltd., Japan.

FIGS. 21 and 22 show that, the higher the voltage applied, the higher the concentrations of negative and positive ions and that, with the same voltage applied, the concentrations are higher when the glass tube 203 has an external diameter of 24 mm than when it has an external diameter of 17 mm or 20 mm.

On the other hand, FIG. 23 shows that the concentration of ozone is far higher when the glass tube 203 has an external diameter of 24 mm than when it has an external diameter of 17 mm or 20 mm. Comparing how the ion concentrations and the ozone concentration increase when the external diameter of the glass tube 203 is increased from 20 mm to 24 mm will make it clear that the increase in the amount of ozone is far larger than the increase in the amount of ions.

Accordingly, to increase the amount of ions while minimizing the amount of ozone, it is recommended, at least in the case under discussion, that the cylindrical dielectric be given an external diameter of 20 mm or less.

Example 15

Figure 24:
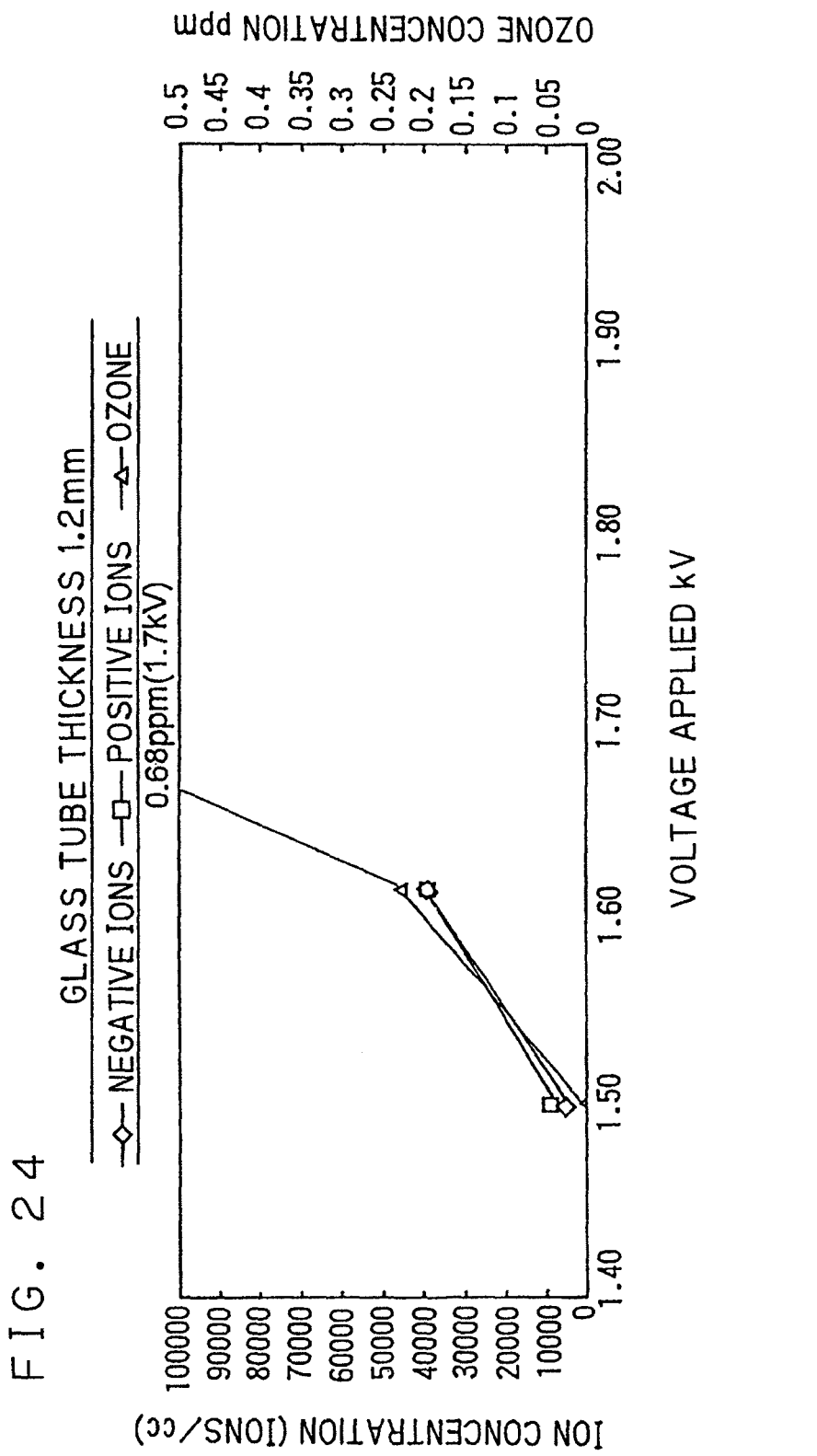
FIG. 24 is a graph showing the relationship between the voltage applied, as expressed in an rms value, and the concentrations of negative and positive ions and of ozone, as measured at a measurement point located 10 cm away from the side surface of the glass tube when the inner electrode was woven from wire 0.18 mm across, was 60 mm long, and had 40 meshes/inch, the outer electrode was woven from wire 0.4 mm across, was 60 mm long, and had 16 meshes/inch, and the glass tube was 63 mm long, had an external diameter of 20 mm, and was 1.2 mm thick in the ion generating device.
Figure 25:
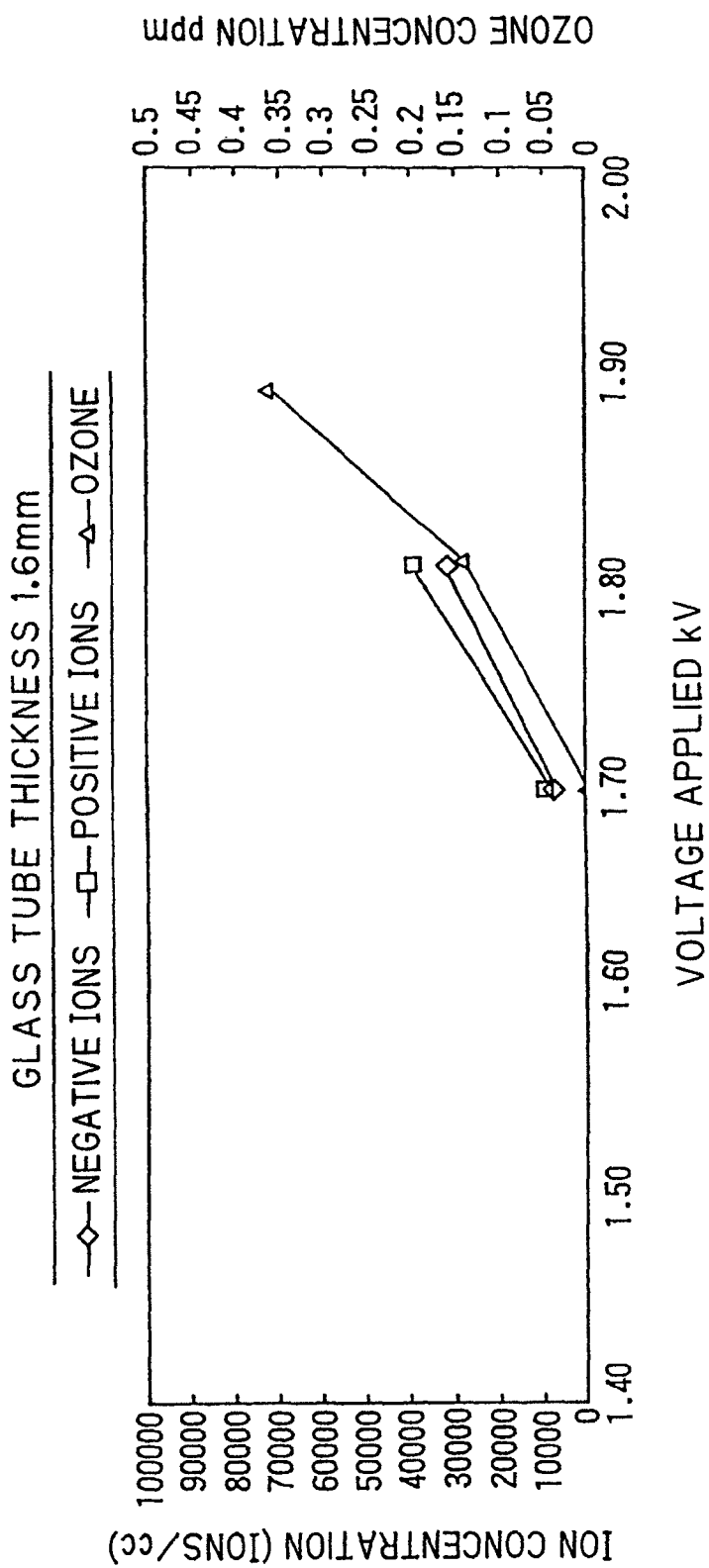
FIG. 25 is a graph showing the relationship between the voltage applied, as expressed in an rms value, and the concentrations of negative and positive ions and of ozone, as measured at a measurement point located 10 cm away from the side surface of the glass tube when the inner electrode was woven from wire 0.18 mm across, was 60 mm long, and had 40 meshes/inch, the outer electrode was woven from wire 0.4 mm across, was 60 mm long, and had 16 meshes/inch, and the glass tube was 63 mm long, had an external diameter of 20 mm, and was 1.6 mm thick in the ion generating device.

FIGS. 24 and 25 show the relationship between the voltage applied, as expressed in an rms value, and the concentrations of negative and positive ions and of ozone, as measured at a measurement point located 10 cm away from the side surface of the glass tube 203 when the inner electrode 204 was woven from wire 0.18 mm across, was 60 mm long, and had 40 meshes/inch, the outer electrode 205 was woven from wire 0.4 mm across, was 60 mm long, and had 16 meshes/inch, and the glass tube 203 was 63 mm long, had an external diameter of 20 mm, and was either 1.2 mm or 1.6 mm thick. The concentrations of ions and ozone were measured using, respectively, an airborne ion counter, model 83-1001B manufactured by Dan Kagaku Co., Ltd., Japan, and a UV absorption type ozone monitor, model EG-2001 manufactured by Ebara Jitsugyo Co., Ltd., Japan.

Comparing these figures will make it clear that, as the glass tube 203 is made thinner, the ion concentrations become far higher, and they also come to exhibit greater variations according to the voltage applied. Thus, it is recommended, at least in the case under discussion, that the glass tube 203 be made 1.6 mm thick or thinner.

Table 7 shows the results of an experiment conducted to study the relationship between the external diameter of the glass tube 203, the thickness thereof, and the capacitance obtained. As described earlier, to increase the amount of ions while minimizing the amount of ozone, the glass tube 203 is preferably given an external diameter of 20 mm or less and a thickness of 1.6 mm or less. Accordingly, the preferred capacitance of the glass tube 203 is 40 pF or lower, if variations inevitable in its measurement are taken into consideration.

In addition to minimizing the generation of ozone in this way, impregnating at least one of the glass tube 203, the inner electrode 204, and the outer electrode 205 with an ozone decomposition catalyst helps efficiently remove the ozone that is inevitably generated in the ion generating electrode member. The generated ozone gradually decomposes into oxygen naturally, and the presence of an ozone decomposition catalyst promotes this decomposition of ozone into oxygen. As the ozone decomposition catalyst, any known substance can be used, for example, manganese dioxide, platinum powder, lead dioxide, copper(II) oxide, nickel.

The impregnation of the ozone decomposition catalyst is achieved, for example, by dispersing the ozone decomposition catalyst in a binder and then applying it to the surface of the target member by a coating process such as dipping, spinning, or spraying. The ozone decomposition catalyst may be impregnated in any amount as determined according to the amount of ozone generated and other factors.

Figure 26A:
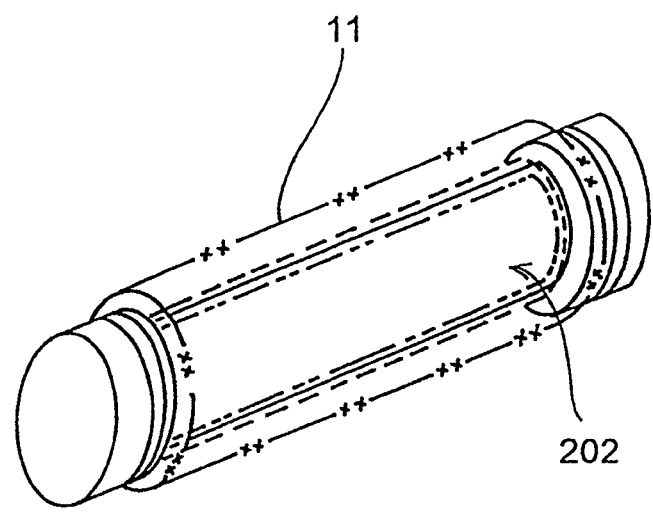
FIG. 26A is a perspective view showing an example of the ion generating electrode member provided with a catalyst impregnated member impregnated with an ozone decomposition catalyst.
Figure 26B:
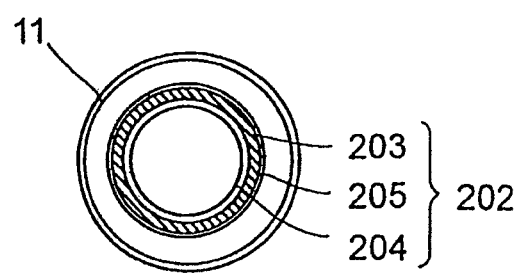
FIG. 26B is a sectional view of the ion generating electrode member.

Alternatively, it is also possible to separately provide a catalyst impregnated member impregnated with an ozone decomposition catalyst outside the outer electrode 205. FIGS. 26A and 26B show an example of the ion generating electrode member 202 provided with such a catalyst impregnated member 11. Here, a catalyst impregnated member 11 is provided outside the cylindrical outer electrode 205, at a predetermined distance therefrom. The catalyst impregnated member 11 is formed as a mesh, and its surface is impregnated with an ozone decomposition catalyst such as manganese dioxide. The catalyst impregnated member 11 may cover the whole or a part of the outer electrode 205.

In cases where the ion generating electrode member 202 has both the inner and outer electrodes 204 and 205 formed as a mesh, if the inner and outer electrodes 204 and 205 move relative to each other axially, the concentrations of positive and negative ions generated vary in the range from 1,000 to 180,000 ions/cc and in the range from 3,000 to 180,000 ions/cc, respectively. This is considered to result from the fact that the electric discharge that takes place between the inner and outer electrodes 204 and 205, which are here regarded as two aggregates of lines arranged so as to face each other with the glass tube 203 disposed in between, weakens as the pieces of wire constituting those electrodes are displaced relative to each other.

To avoid this problem, the ion generating electrode member 202 may be modified so as to have the inner electrode 204 formed as a sheet and the outer electrode 205 as a mesh. Here, forming the inner electrode 204 as a sheet makes it easier to put it into intimate contact with the glass tube 203 so that the distance between the inner and outer electrodes 204 and 205 is kept substantially fixed. Moreover, even if the inner and outer electrodes 204 and 205 move relative to each other, the inner electrode 204 formed as a sheet minimizes the influence of the displacement, as long as it is not too large. On the other hand, forming the outer electrode 205 as a mesh helps prompt the concentration of the electric field, and thus makes it possible to lower the voltage, as expressed in an rms value, applied between the inner and outer electrodes 204 and 205.

Here, as the glass tube 203, for example, a cylindrical tube of Pyrex glass is used. As the inner electrode 204, for example, a sheet of stainless steel 304 or 316 is used, and, as the outer electrode 205, for example, a wire mesh produced by plain-weaving wire of stainless steel 316 or 304 is used. In this case, except for the process of putting the inner electrode 204 into intimate contact with the glass tube 203, the ion generating electrode member 202 can be produced in the same manner as described earlier.

Figure 27:
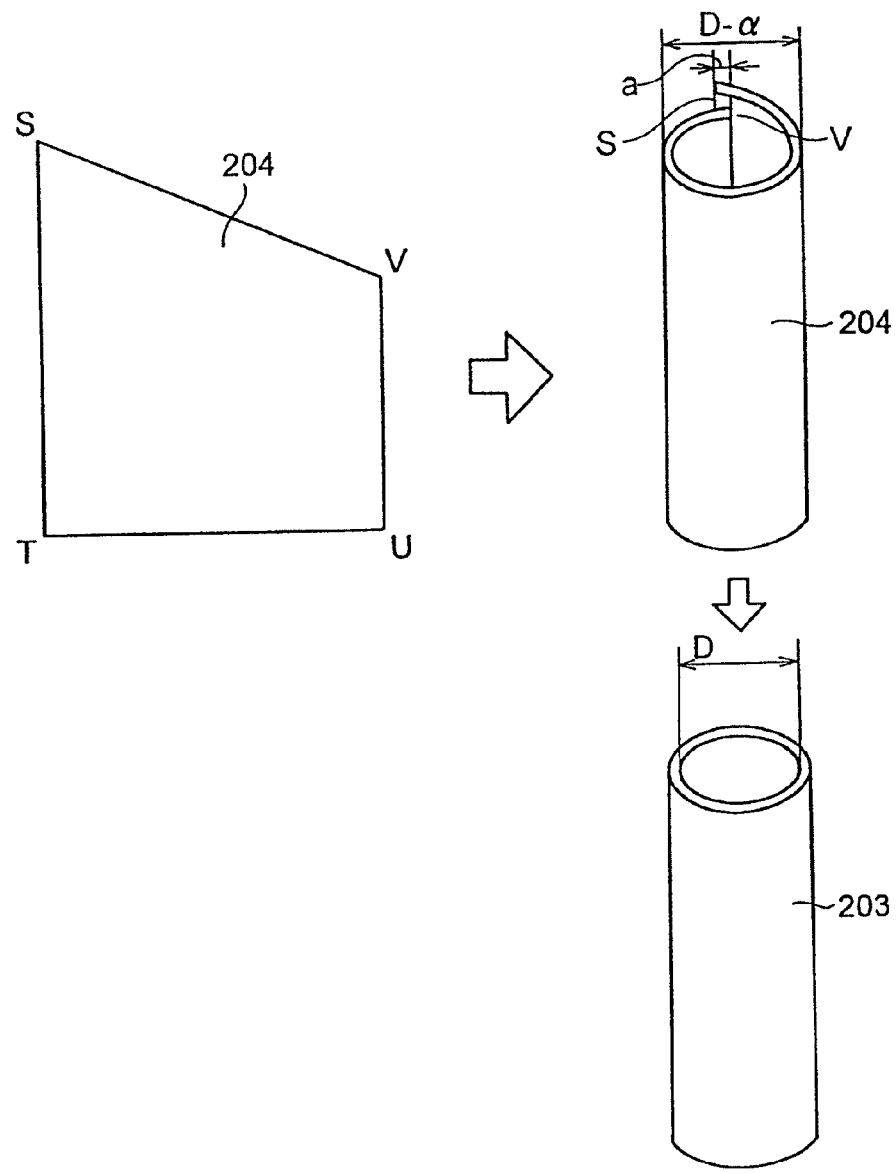
FIG. 27 is a perspective view illustrating an example of how the sheet-form inner electrode is put in intimate contact with the inner surface of the glass tube in the ion generating device.

The inner electrode 204 is put into intimate contact with the glass tube 203, for example, in the following manner. As shown in FIG. 27, sheet metal is pressed to blank out a sheet-form electrode having the shape of a quadrilateral STUV. Here, side ST is parallel to side UV, angle T=angle V=90°, angle S is an acute angle, and angle V is an obtuse angle. The inner electrode 204 is produced by rolling this sheet-form electrode into a cylindrical form in such a way that sides ST and UV are parallel to the axis of the cylinder and that the inner electrode 204 thus produced has an external diameter larger than the internal diameter of the glass tube 203. Here, opposite side edges (sides ST and UV) of the inner electrode 204 are left free, i.e. unwelded together. The resulting cylinder is substantially flat at one end corresponding to side TU, and has the acute-angle corner S protruding from the obtuse-angle corner V at the other end.

Figure 28:
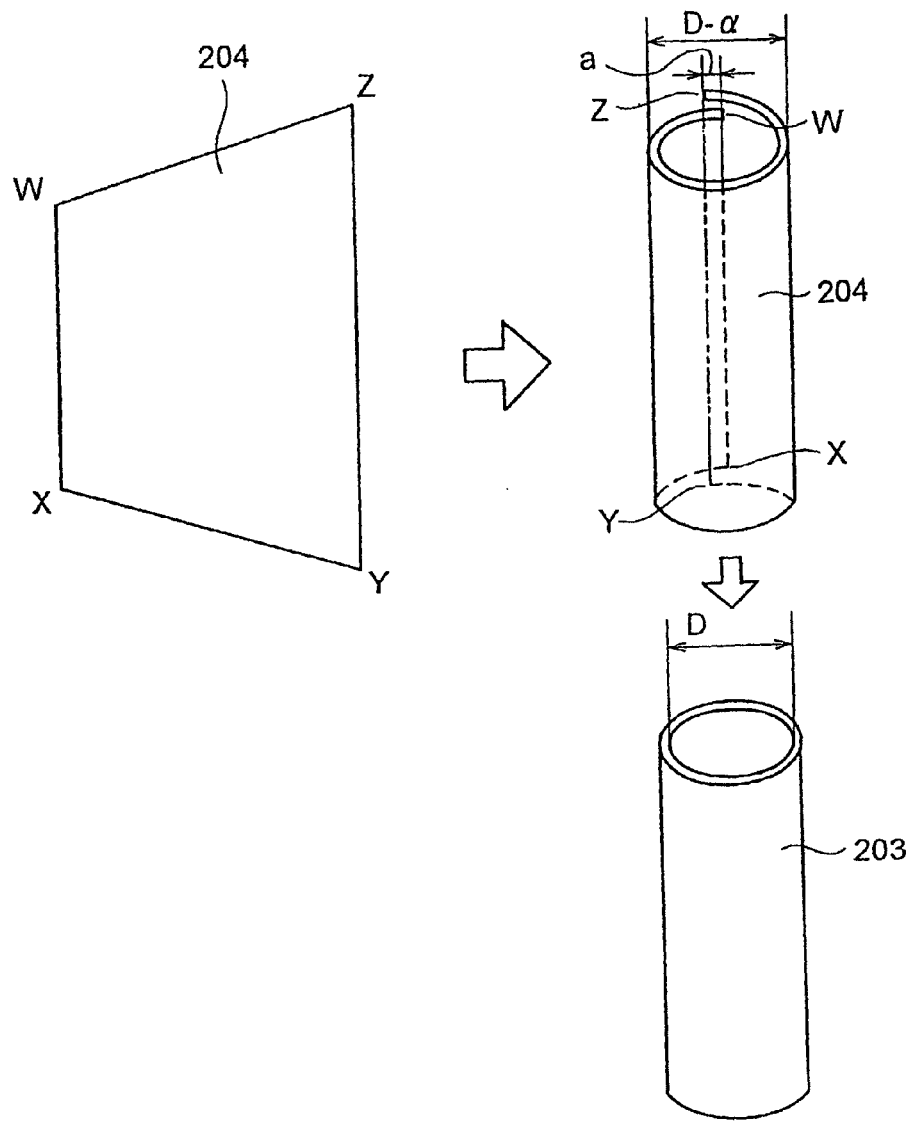
FIG. 28 is a perspective view illustrating another example of how the sheet-form inner electrode is put in intimate contact with the inner surface of the glass tube in the ion generating device.

Alternatively, it is also possible to press sheet metal so as to blank out a sheet-form electrode having a shape composed solely of non-90° angles, i.e. acute or obtuse angles, for example a trapezoid WXYZ as shown in FIG. 28. The inner electrode 204 is produced by rolling this sheet-form electrode into a cylindrical form in such a way that its parallel sides WX and ZY are parallel to the axis of the cylinder and that the inner electrode 204 so produced has an external diameter larger than the internal diameter of the glass tube 203. Here, angles W and X are obtuse angles, and angles Y and Z are acute angles. Opposite side edges (sides WX and ZY) of the inner electrode 204 are left free, i.e. unwelded together. The resulting cylinder has the two acute-angle corners Y and Z protruding outward.

Shapes composed solely of non-90° angles include a variety of shapes from polygons, such as triangles, quadrilaterals, pentagons, and hexagons, to shapes that are almost circular but has one corner, i.e. any shape that can be rolled into a cylindrical shape with at least one corner protruding outward.

Then, force is applied at one side edge of the inner electrode 204, thus produced by rolling a sheet-form electrode into a cylindrical shape, in a tangential direction, as if to roll up the cylinder further, so that the internal diameter of the inner electrode 204, which is otherwise greater than the internal diameter (D) of the glass tube 203, becomes temporarily smaller (D−α) than it. With the inner electrode 204 in this state, it is inserted in the glass tube 203. After insertion, when the tangential force ceases to be applied, the inner electrode 204 tends to restore its original state, and is thereby put into intimate contact with the inner surface of the glass tube 203.

The ion generating electrode member 202 thus produced was subjected to a test in which an alternating-current voltage was applied thereto to generate ions. The test showed that this ion generating electrode member 202 could generate negative and positive ions stably, both in concentrations of 400,000 to 600,000 ions/cc, even if the inner and outer electrodes 204 and 205 moved relative to each other, as long as the displacement was not too large. For comparison, forming the inner and outer electrodes 204 and 205 both as a sheet yielded almost no ions.

In this arrangement, where the inner electrode 204 is formed by rolling a sheet-form electrode into a cylindrical shape with at least one corner protruding from one end of the cylinder, making the inner electrode 204 shorter than the outer electrode 205 in the direction of their length permits the high alternating-current voltage to discharge from around such a corner of the inner electrode 204 to a wide area on the mesh-form outer electrode 205. This helps achieve a proper balance between the amounts of negative and positive ions. By contrast, making the inner electrode 204 longer than the outer electrode 205 in the direction of their length causes the high alternating-current voltage to discharge from around a corner of the inner electrode 204 to a localized spot on the mesh-form outer electrode 205. This tips the balance between the amounts of negative and positive ions in favor of positive ions.

Figure 29:
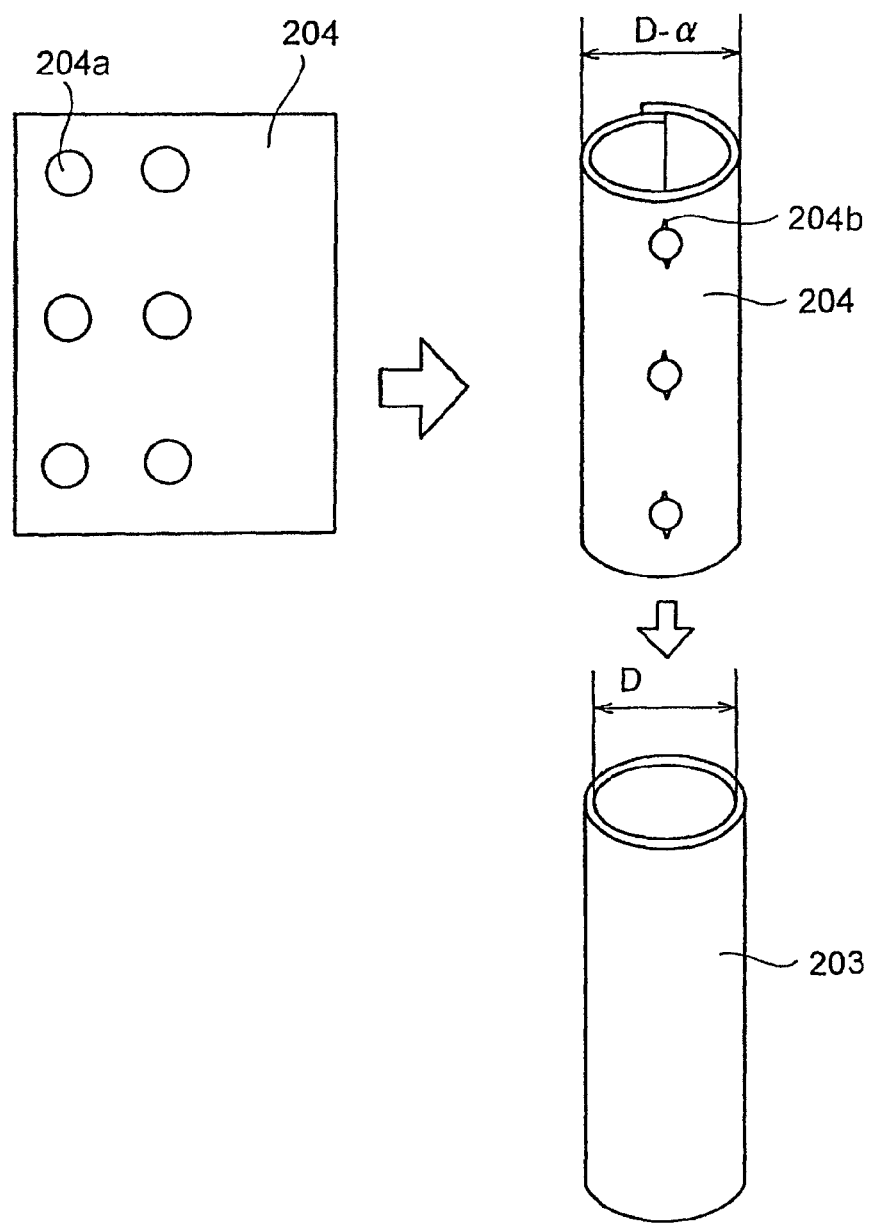
FIG. 29 is a perspective view illustrating another example of how the sheet-form inner electrode is put in intimate contact with the inner surface of the glass tube in the ion generating device.

Another way of putting the inner electrode 204 into intimate contact with the glass tube 203 is as follows. As shown in FIG. 29, a plurality of holes 204a are formed in sheet metal, then the sheet metal is pressed to form projections 204b around the holes, and then the inner electrode 204 is produced by rolling this sheet metal into a cylindrical shape in such a way that the projections 204b around the holes 204a protrude toward the glass tube 2 and that the inner electrode 204 thus produced has an external diameter larger than the internal diameter of the glass tube 2. Here, opposite side edges of the inner electrode 204 are left free, i.e. unwelded together. Moreover, the rolling is performed in such a way that, in the resulting cylinder, the projections 204b formed around the holes 204a protrude toward the inner surface of the glass tube 2.

Then, force is applied at one side edge of the inner electrode 204, thus produced by rolling a sheet-form electrode into a cylindrical shape, as if to roll up the cylinder further so that the internal diameter of the inner electrode 204, which is otherwise greater than the internal diameter (D) of the glass tube 203, becomes temporarily smaller (D−α) than it. With the inner electrode 204 in this state, it is inserted in the glass tube 203. After insertion, when the force ceases to be applied, the inner electrode 204 tends to restore its original state, and is thereby put into intimate contact with the inner surface of the glass tube 203.

As a result, between the sheet-form inner electrode 204 and the mesh-form outer electrode 205 that face each other with the glass tube 203 disposed in between, electric discharge takes place from a plurality of surfaces to a plurality of points. This ensures strong electric discharge on the surfaces. Moreover, the projections 204b prompt electric discharge by limiting the spots at which electric discharge occurs. This ensures stable electric discharge.

Example 16

Figure 30:
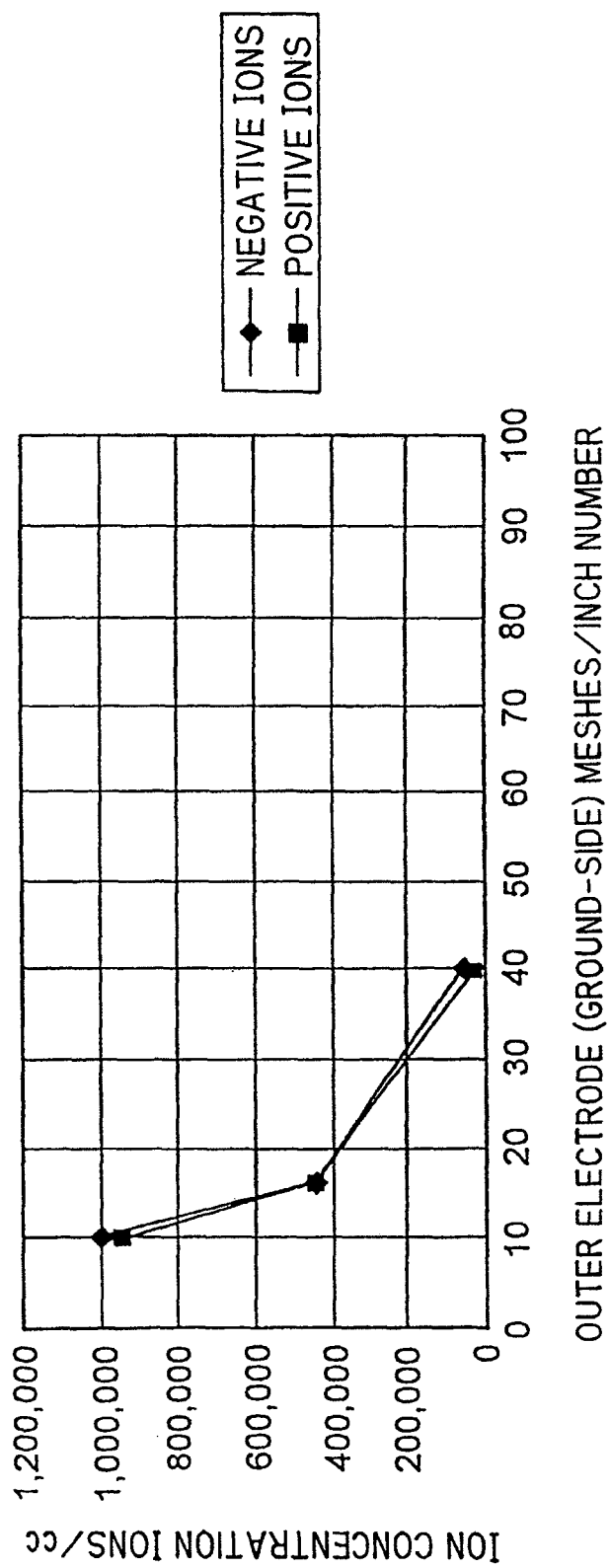
FIG. 30 is a graph showing the amounts of negative and positive ions generated, as measured at a measurement point located 10 cm away from the side surface of the glass tube when an alternating-current voltage of about 1.8 kV rms was applied to the ion generating electrode member of the ion generating device, in which the glass tube had an external diameter of 20 mm, was 63 mm long, and was 1.6 mm thick, the inner electrode, here a sheet formed into a cylindrical shape, was 45 mm long, and was 0.08 mm thick, and the outer electrode, here a mesh formed into a cylindrical shape, was 60 mm long, and had a varying number of meshes/inch.

FIG. 30 shows the amounts of negative and positive ions generated, as measured at a measurement point located 10 cm away from the side surface of the glass tube 203 when an alternating-current voltage of about 1.8 kV rms was applied to the ion generating electrode member 202, in which the glass tube 203 had an external diameter of 20 mm, was 63 mm long, and was 1.6 mm thick, the inner electrode 204, here a sheet formed into a cylindrical shape, was 45 mm long, and was 0.08 mm thick, and the outer electrode 205, here a mesh formed into a cylindrical shape, was 60 mm long, and had a varying number of meshes/inch. Here, the wire diameter of the outer electrode 205 varied according to its meshes/inch number. The concentrations of ions were measured using an airborne ion counter, model 83-1001B manufactured by Dan Kagaku Co., Ltd., Japan.

As shown in FIG. 30, the meshes/inch number of the outer electrode 205 greatly influences the amount of ions generated; specifically, the smaller its meshes/inch number, the larger the amounts of ions generated. Without the holes, the inner electrode 204 produced smaller amounts of ions.

Example 17

Figure 31:
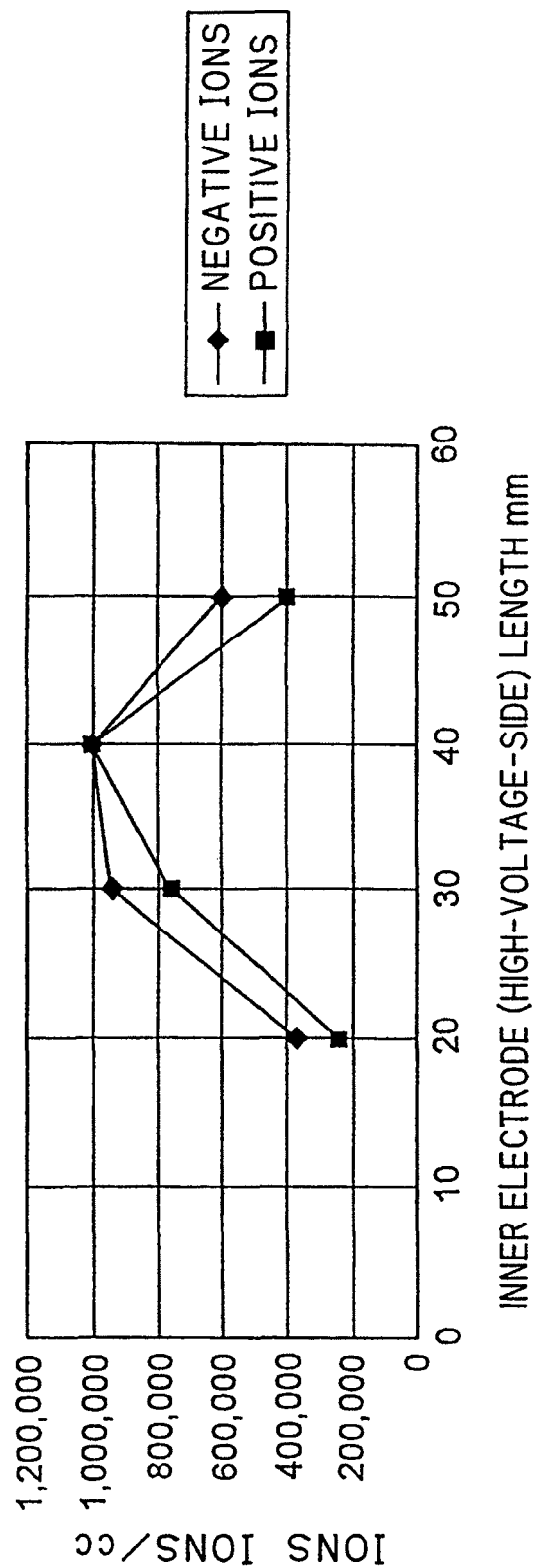
FIG. 31 is a graph showing the amounts of negative and positive ions generated, as measured at a measurement point located 10 cm away from the side surface of the glass tube when an alternating-current voltage of about 1.8 kV rms was applied to the ion generating electrode member of the ion generating device, in which the glass tube had an external diameter of 20 mm, was 63 mm long, and was 1.6 mm thick, the inner electrode, here a sheet formed into a cylindrical shape, was 0.08 mm thick, and had a varying length, and the outer electrode, here a mesh formed into a cylindrical shape, was woven from wire 0.22 mm across, was 60 mm long, and had 16 meshes/inch.

FIG. 31 shows the amounts of negative and positive ions generated, as measured at a measurement point located 10 cm away from the side surface of the glass tube 203 when an alternating-current voltage of about 1.8 kV rms was applied to the ion generating electrode member 202, in which the glass tube 203 had an external diameter of 20 mm, was 63 mm long, and was 1.6 mm thick, the inner electrode 204, here a sheet formed into a cylindrical shape, was 0.08 mm thick, and had a varying length, and the outer electrode 205, here a mesh formed into a cylindrical shape, was woven from wire 0.22 mm across, was 50 mm long, and had 16 meshes/inch. Here, the wire diameter of the outer electrode 205 varied according to its meshes/inch number. The concentrations of ions were measured using an airborne ion counter, model 83-1001B manufactured by Dan Kagaku Co., Ltd., Japan.

As shown in FIG. 31, the amounts of ions generated are low when the sheet-form inner electrode 204 and the mesh-form outer electrode 205 are made equally long, and the amounts of ions increase as the inner electrode 204 is made shorter than the outer electrode 205. However, when the inner electrode 204 is made too short, the amounts of ion start to drop.

Example 18

Figure 32:
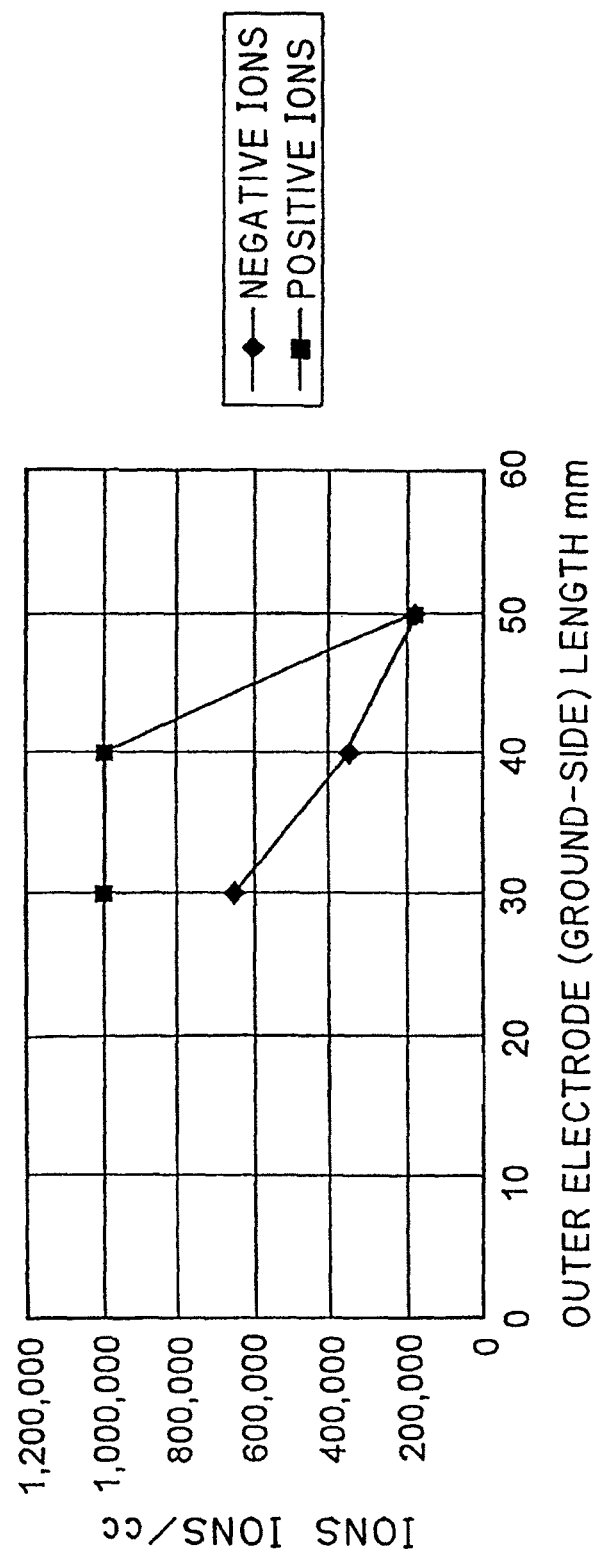
FIG. 32 is a graph showing the amounts of negative and positive ions generated, as measured at a measurement point located 10 cm away from the side surface of the glass tube when an alternating-current voltage of about 1.8 kV rms was applied to the ion generating electrode member of the ion generating device, in which the glass tube had an external diameter of 20 mm, was 63 mm long, and was 1.6 mm thick, the inner electrode, here a sheet formed into a cylindrical shape, was 0.08 mm thick, and was 50 mm long, and the outer electrode, here a mesh formed into a cylindrical shape, was woven from wire 0.22 mm across, had a varying length, and had 16 meshes/inch.

FIG. 32 shows the amounts of negative and positive ions generated, as measured at a measurement point located 10 cm away from the side surface of the glass tube 203 when an alternating-current voltage of about 1.8 kV rms was applied to the ion generating electrode member 202, in which the glass tube 203 had an external diameter of 20 mm, was 63 mm long, and was 1.6 mm thick, the inner electrode 204, here a sheet formed into a cylindrical shape, was 0.08 mm thick, and was 50 mm long, and the outer electrode 205, here a mesh formed into a cylindrical shape, was woven from wire 0.22 mm across, had a varying length, and had 16 meshes/inch. The concentrations of ions were measured using an airborne ion counter, model 83-1001B manufactured by Dan Kagaku Co., Ltd., Japan.

As shown in FIG. 32, as the outer electrode 205 is made shorter than the inner electrode 204, the amounts of ions generated increase, but positive ions tend to increase at a far higher rate than negative ions. Therefore, it is advisable that the outer electrode 205 be made longer than the inner electrode 204.

Figure 33A:
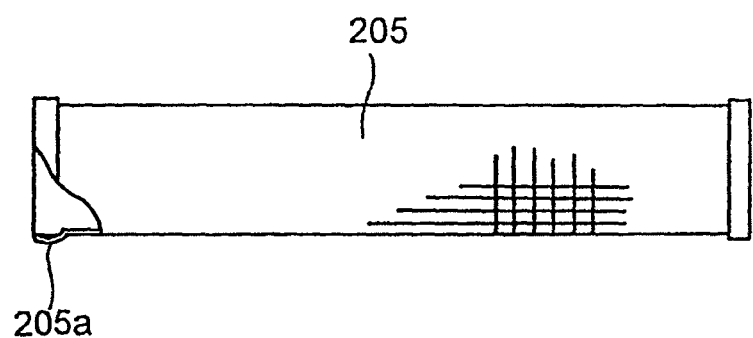
FIG. 33A is a plan view, partially cutaway, of an example of the mesh-form outer electrode that is fitted around the glass tube of the ion generating electrode member so as to be kept in intimate contact with the outer surface thereof.

As shown in FIG. 33A, parts of both ends of the outer electrode 205 may be folded back and curled to form folded portions 205a so that the outer electrode 205 is double-layered at both ends. In this case, the outer electrode 205 is so formed as to have an internal diameter slightly smaller than the external diameter of the glass tube 203.

Figure 33B:
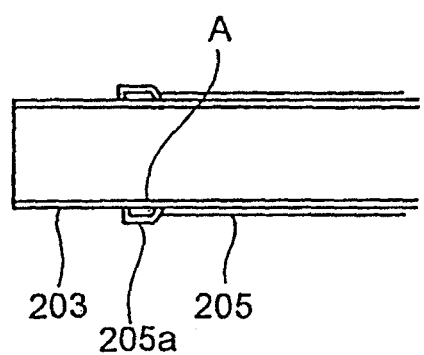
FIG. 33B is a sectional view showing how the outer electrode is fitted around the glass tube so as to be kept in intimate contact therewith.

Then, the outer electrode 205 is press-fitted into position around the glass tube 203. This puts the folded portions 205a, i.e. the double-layered portions, of the outer electrode 205 into intimate contact with the glass tube 203, leaving, as shown in FIG. 33B, spaces A around which the folded portions 205a do not make contact with the glass tube 203. Then, the outer electrode 205 is, in several positions along its axis, tightened from outside with elastic tightening members so as to be fixed to the glass tube 203. This puts the outer electrode 205 as a whole into intimate contact with the glass tube 203.

Example 19

An alternating-current voltage of 2.1 kV rms was applied to the ion generating electrode member 202 having folded portions 205a formed at both ends of the outer electrode 205 as shown in FIG. 33B, in which the glass tube 203 had an external diameter of 20 mm, was 150 mm long, and was 1.2 mm thick, the inner electrode 204 was 95 mm long, and was 0.08 mm thick, and the outer electrode 205 was woven from wire 0.4 mm across, was 98 mm long, and had 30 meshes/inch.

As a result, at a measurement point located 10 cm away from the side surface of the glass tube 203, negative and positive ions were obtained in concentrations of 400,000 to 600,000 ions/cc, with reproducibility of 80% for the total number of ion generating electrode members 202 produced in the same manner. The concentrations of ions were measured using an airborne ion counter, model 83-1001B manufactured by Dan Kagaku Co., Ltd., Japan.

Figure 34A:
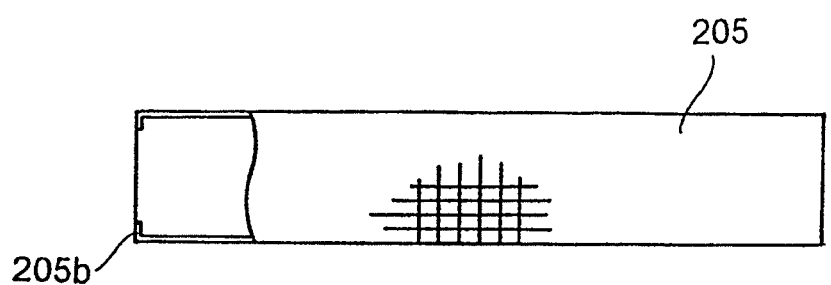
FIG. 34A is a plan view, partially cutaway, of another example of the mesh-form outer electrode that is fitted around the glass tube of the ion generating electrode member so as to be kept in intimate contact with the outer surface thereof.
Figure 34B:
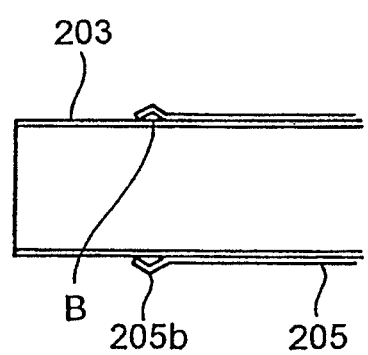
FIG. 34B is a sectional view showing how the outer electrode is fitted around the glass tube so as to be kept in intimate contact therewith.

As an alternative to curling both ends of the outer electrode 205, it is also possible, as shown in FIG. 34A, to form bent portions 205b there by bending the corresponding edges of the originally rectangular or square mesh material of the outer electrode 205 into an inward pointing L-shape. These bent portions 205b may be formed at any angle as long as, when the outer electrode 205 is formed by rolling the mesh material into a cylindrical shape, the tip portions of the bent portions 205b can be put into intimate contact with the glass tube 203 all around the periphery thereof as shown in FIG. 34B. The bent portions 205b may have an arch-shaped section as long as their tip portions make contact with the glass tube 203, achieving the same purpose. Thereafter, as required, spot welding is applied to four corners of the mesh material to prevent it from getting loose, and then the mesh material is rolled into a cylindrical shape.

Here, the outer electrode 205 is so produced as to have an internal diameter slightly larger than the external diameter of the glass tube 203. Then, the outer electrode 205 is press-fitted into position around the glass tube 203. This puts the bent portions 205b at both ends of the outer electrode 205 into intimate contact with the glass tube 203. When fitted around the glass tube 203, the bent portions 205b leave, as shown in FIG. 34B, slight spaces B between themselves and the glass tube 203. Then, the outer electrode 205 is, in several positions along its axis, fixed to the glass tube 203 with locking members, and is thereby brought into intimate contact with the glass tube 203.

Moreover, the electrodes 204 and 205 are mounted on the glass tube 203 in such a way that their axially central portions face each other. This makes it possible to arrange the inner and outer electrodes 204 and 205 in such a way that, when the outer electrode 205 is projected onto the inner electrode 204, the ends of the inner electrode 204 lie inside the projected view of the outer electrode 205. Specifically, here, the error in position between an end of the inner electrode 204 and the corresponding end of the outer electrode 205 falls within a range of about 0.5 to 1.0 mm.

This arrangement ensures stable electric discharge between a corner at an end of the sheet-form inner electrode 204 (corners Y and Z in FIG. 20) and the outer electrode 205 that is kept in intimate contact with the glass tube 203. Here, stable electric discharge is considered to result from the fact that, whereas the inner electrode 204 to which the voltage is applied has a pointed end, the outer electrode 205 acts as an aggregate of lines kept in contact with the glass tube 203, and thus electric discharge occurs, if considered locally, between a point and a surface Example 20

An alternating-current voltage of 2.1 kV rms was applied to the ion generating electrode member 202 having L-shaped bent portions 205b formed at both ends of the outer electrode 205 with the tip portions of those bent portions 205b kept in contact with the glass tube 203 as shown in FIG. 34B, in which the glass tube 203 had an external diameter of 20 mm, was 150 mm long, and was 1.2 mm thick, the inner electrode 204 was 95 mm long, and was 0.08 mm thick, and the outer electrode 205 was woven from wire 0.4 mm across, was 98 mm long, and had 30 meshes/inch.

As a result, at a measurement point located 10 cm away from the side surface of the glass tube 203, negative and positive ions were obtained in concentrations of 400,000 to 600,000 ions/cc, with reproducibility of 100% for the total number of ion generating electrode members 202 produced in the same manner. Here, it was confirmed that the electric discharge occurring between the inner and outer electrodes 204 and 205 was more stable when, of the bent portions 205b that might be formed at both ends of the outer electrode 205 and kept in contact with the glass tube 203, only one was formed than when none was formed, and that the electric discharge was still more stable when both of those bent portions 205b were formed than when only one was formed. The concentrations of ions were measured using an airborne ion counter, model 83-1001B manufactured by Dan Kagaku Co., Ltd., Japan.

As described above, in the ion generating device 201 of this embodiment, the use of a cylindrical dielectric makes the handling of the ion generating electrode member 202 easy, helps save space, and stabilizes the performance of the ion generating device 201. This permits the ion generating device 201 to be advantageously incorporated in various air conditioning apparatus.

Figure 35:
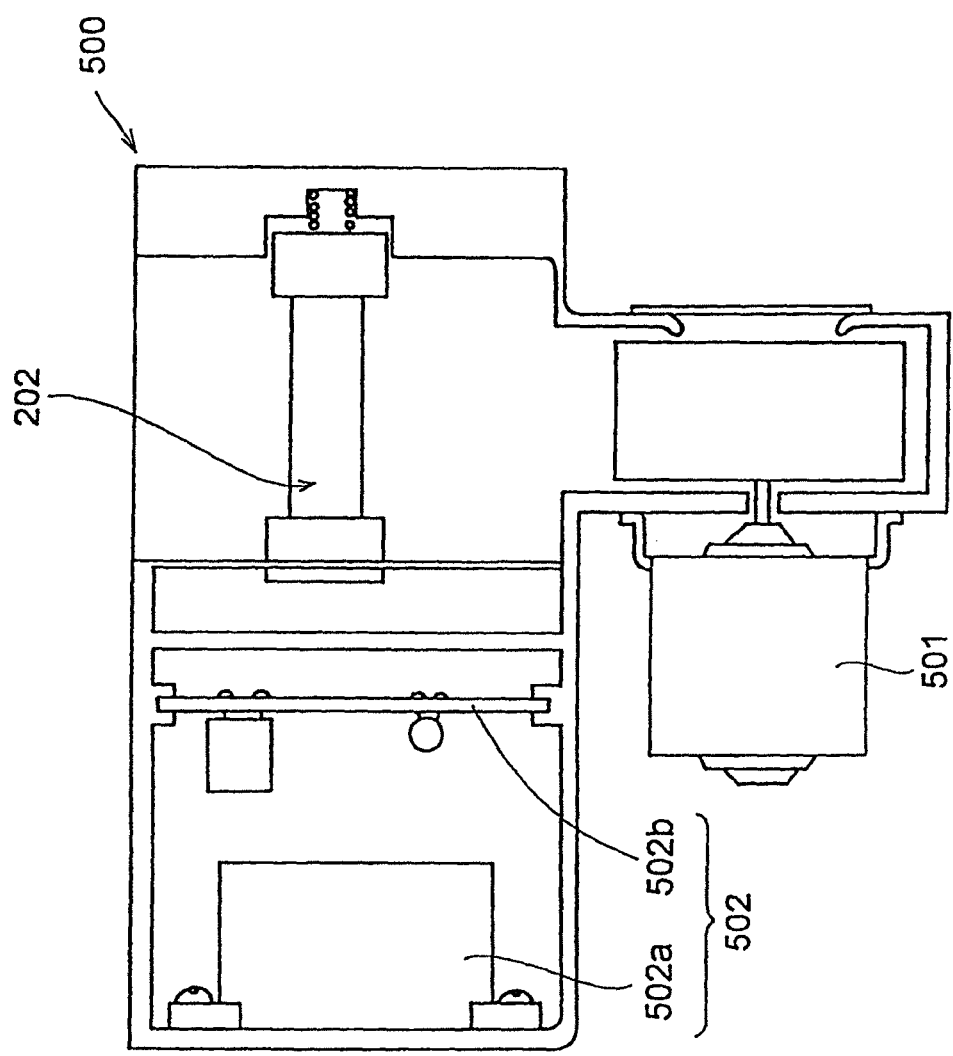
FIG. 35 is a sectional view showing an example of the ion generating device of an eighth embodiment of the invention.

Now, an eighth embodiment of the invention will be described with reference to the drawings. FIG. 35 is a sectional view showing an example of the ion generating device 500 of an eighth embodiment of the invention. One of the key features of this ion generating device 500 is that it is provided with the ion generating electrode member 202 of the ion generating device 201 (see FIG. 8) described above in connection with the seventh embodiment to generate negative and positive ions and kill and remove airborne germs therewith.

The ion generating device 500 is provided with an ion generating electrode member 202, a blower 501, a filter (not shown), and a high-voltage power supply circuit 502 composed of a high-voltage transformer 502a and a control circuit board 502b. Air taken in through an inlet (not shown) passes through the filter, which removes dust from the air, and then reaches the blower 501, which blows the air to the ion generating electrode member 202. The ion generating electrode member 202, when fed with a predetermined alternating-current voltage from the high-voltage power supply circuit 502, generates negative and positive ions from the air. By the action of these positive and negative ions, airborne germs are removed from the air. On the other hand, ozone is also generated as a byproduct when the negative and positive ions are generated. Usually, the amount of ozone generated in the ion generating electrode member 202 is within a permissible range. However, the amount of ozone contained in the air blown out of the device may be reduced, as required, by impregnating the ion generating electrode member 202 with an ozone decomposition catalyst or separately providing a catalyst impregnated member 11 (see FIG. 26A) in the air flow passage. The air, having ions generated therein and airborne germs removed therefrom in this way, is then blown out of the device.

This ion generating device 500 can be made compact, and can thus be installed anywhere with minimum space; it can even be hung on a wall. Moreover, by building the ion generating device 500 as a unit, and designing various products to permit the unit to be optionally attached thereto, it is possible to enhance the usability of those products.

Figure 36:
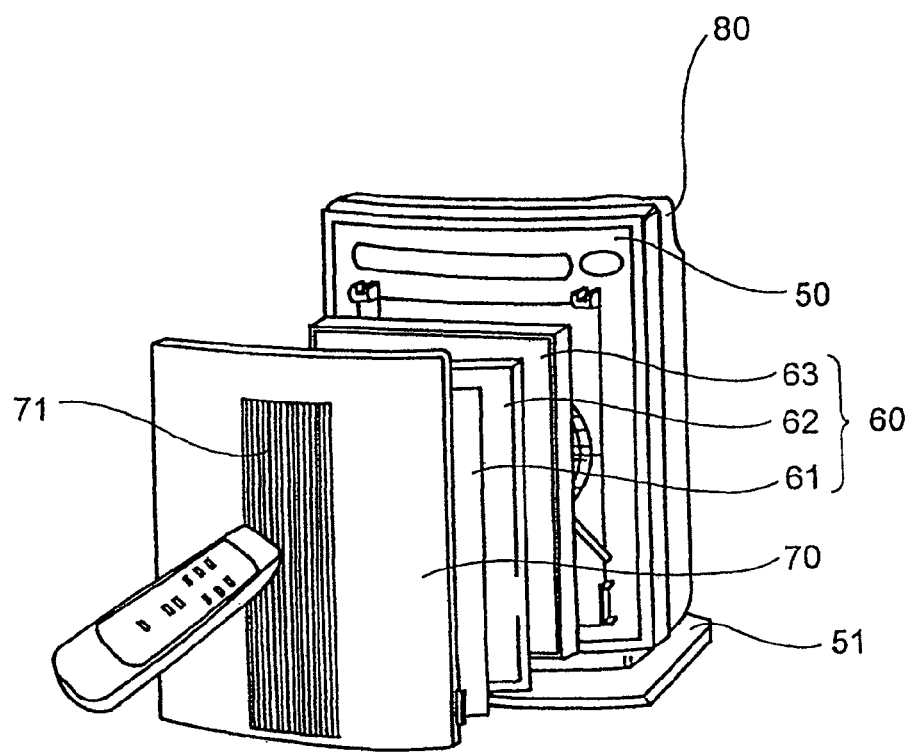
FIG. 36 is an exploded perspective view showing an example of the air purifier, incorporating an ion generating device, of a ninth embodiment of the invention.

Next, a ninth embodiment of the invention will be described with reference to the drawings. FIG. 36 is an exploded perspective view showing an example of the air purifier, incorporating an ion generating device 201, of a ninth embodiment of the invention. The air purifier is provided with a body 50 fixed on a base 51, a filter 60 housed in a housing 51 (see FIG. 37) formed in a front portion of the body 50, a front cover 70 for covering the filter 60 so housed, and a rear cover 80 for covering the back of the body 50.

The filter 60 is composed of, from the front side, a pre-filter 61, a deodorizing filter 62, and a dust collecting filter 63. The pre-filter 61 collects dust and other foreign particles contained in the air sucked into the air purifier. A preferred material for the pre-filter 61 is, for example, polypropylene, which offers high air resistance. The deodorizing filter 62 has a three-layer structure; specifically, it is produced by stretching a piece of nonwoven fabric of polyester on a rectangular frame, then evenly dispersing activated charcoal over it, and then stretching another piece of nonwoven fabric of polyester over it. This structure absorbs and removes odors, such as acetaldehyde, ammonia, and acetic acid, from the air. The dust collecting filter 63 is produced by folding up a filtering material consisting of an electret-type meltblown nonwoven fabric ("Toraymicron" manufactured by Toray Industries Inc., Japan) and a structural material (a polyester/vinylon-based nonwoven fabric), then thermocompression-bonding antibacterial sheets over the top and bottom surfaces thereof, then inserting the thus obtained filtering element into a frame, and then fusion-bonding the frame to the filtering element. This dust collecting filter 63 collects particularly small dust and other foreign particles in the air.

The front cover 70 is so curved as to be slightly convex frontward in the center thereof as seen in a horizontal section, and has an inlet 71, through which indoor air is sucked in, formed in the center thereof as seen in a front view. The front cover 70 is locked to the body 50 with a predetermine distance secured in between, and the gap between the front cover 70 and the body 50 is used as a side inlet 72 (see FIG. 38), through which indoor air is sucked in.

Figure 37:
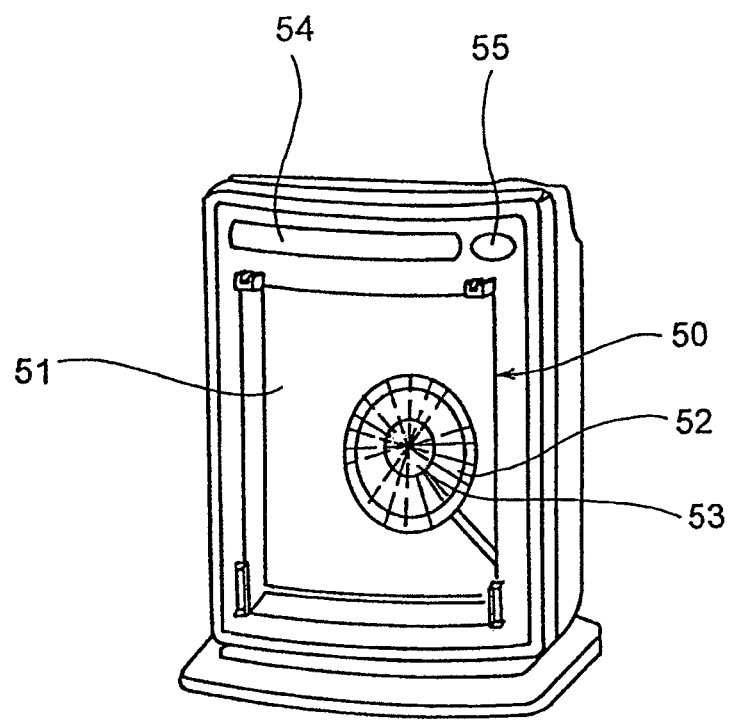
FIG. 37 is a perspective view of the body of the air purifier.

FIG. 37 shows a perspective view of the body 50. The body 50 has the shape of a vertically extending rectangular prism, has a housing 51, for housing the filter 60, formed as a rectangular recess in the front face thereof, and has a vent, consisting of a number of radiating elongate holes 52, formed in the center of the bottom surface of the housing 51. At the center of the vent 52 is formed a further recess 53 for housing a motor 56 (see FIG. 38). On the back side of this recess 53, a fan 57 (see FIG. 38) is fitted on the spindle of the motor 56. In an upper portion of the front face of the body 50 are formed an operation portion 54, including various switches and indicators such as a power switch, air quantity/timer/operation mode setting/selecting switches, and operation status indicator lamps, and a sight window 55 that permits the user to visually check the operation status of the ion generating electrode member.

Figure 39:
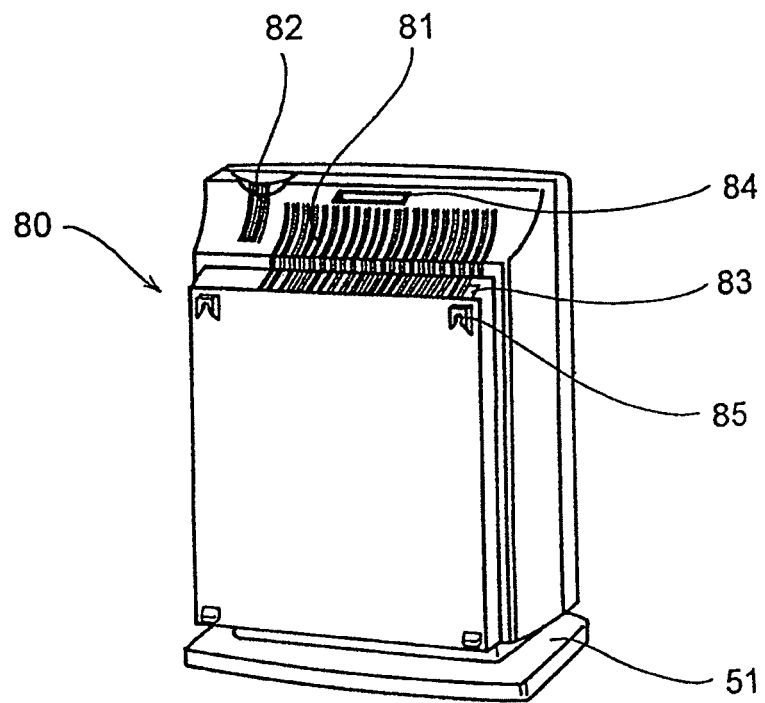
FIG. 39 is a back perspective view of the air purifier.

FIG. 39 shows a back perspective view of the air purifier. In an inclined surface formed in an upper portion of the rear cover 80, an outlet 81 consisting of a number of four-column slit holes is formed, and, in an upper left-hand portion of the inclined surface, an ion outlet 82 consisting of a number of slit holes is formed. Moreover, in an upper central portion of the rear cover 80, a grip 84 is formed as a rectangular recess, and, in two corners of a central, flat portion of the rear cover 80, hanging slots 85 are provided to permit the air purifier to be hung on a wall.

Figure 38:
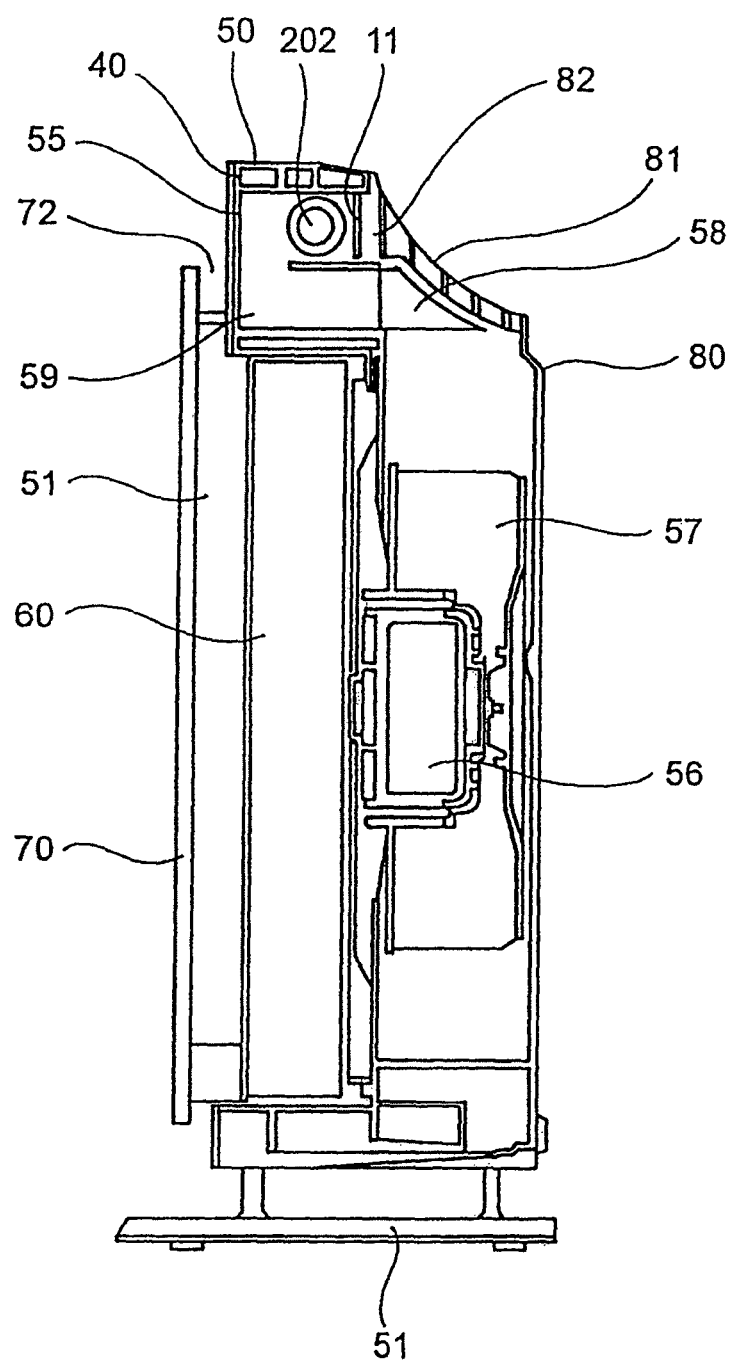
FIG. 38 is a side sectional view of the air purifier.
Figure 40:
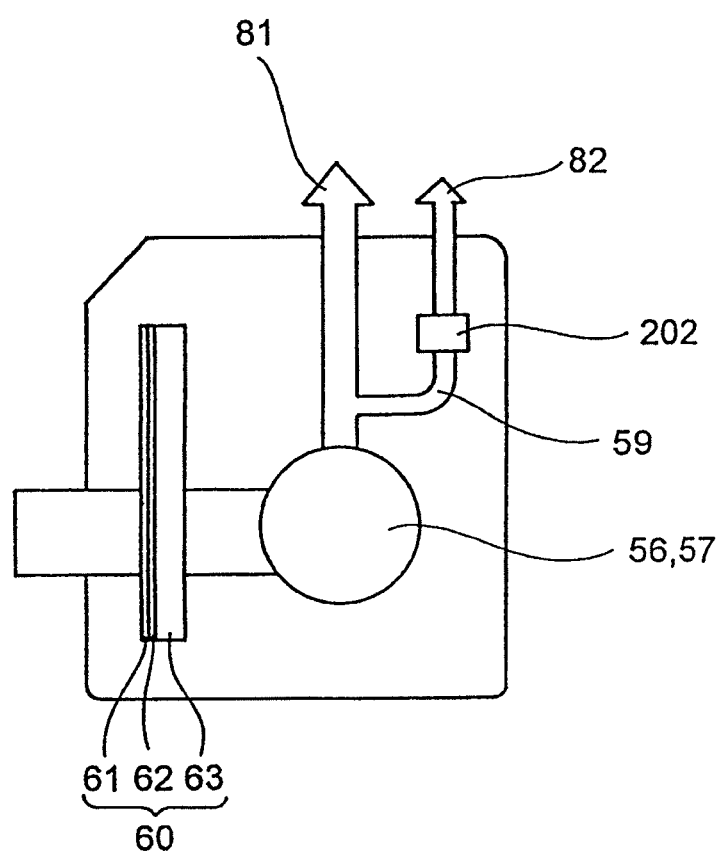
FIG. 40 is a conceptual diagram illustrating the air flow passage formed inside the air purifier.

FIG. 38 shows a side sectional view of the air purifier. When the motor 56 rotates the fan 57, air is sucked in through the inlet 71 and the side inlet 72 formed in the front cover 70. The air thus sucked in then passes through the filter 60 and reaches the fan 57, by which the air is made to flow upward, toward the outlet 81. On the way, a bypass passage 59 is formed that leads to the ion generating electrode member 202 fitted in an upper portion (in an upper right-hand portion as seen in a front view) of the body 50, so that part of the air that is about to be discharged is directed through the bypass passage 59 to the ion generating electrode member 202 (see FIG. 40). The ion generating electrode member 202 generates negative and positive ions simultaneously from part of the air directed thereto, and thus air containing those negative and positive ions is discharged through the ion outlet 82. When the ions are generated, ozone is also generated. However, this ozone is decomposed into oxygen by the catalyst impregnated member 11 impregnated with an ozone decomposition catalyst provided outside the outer electrode 205 (see FIG. 9). This reduces the amount of ozone contained in the air discharged through the ion outlet 82.

Figure 41:
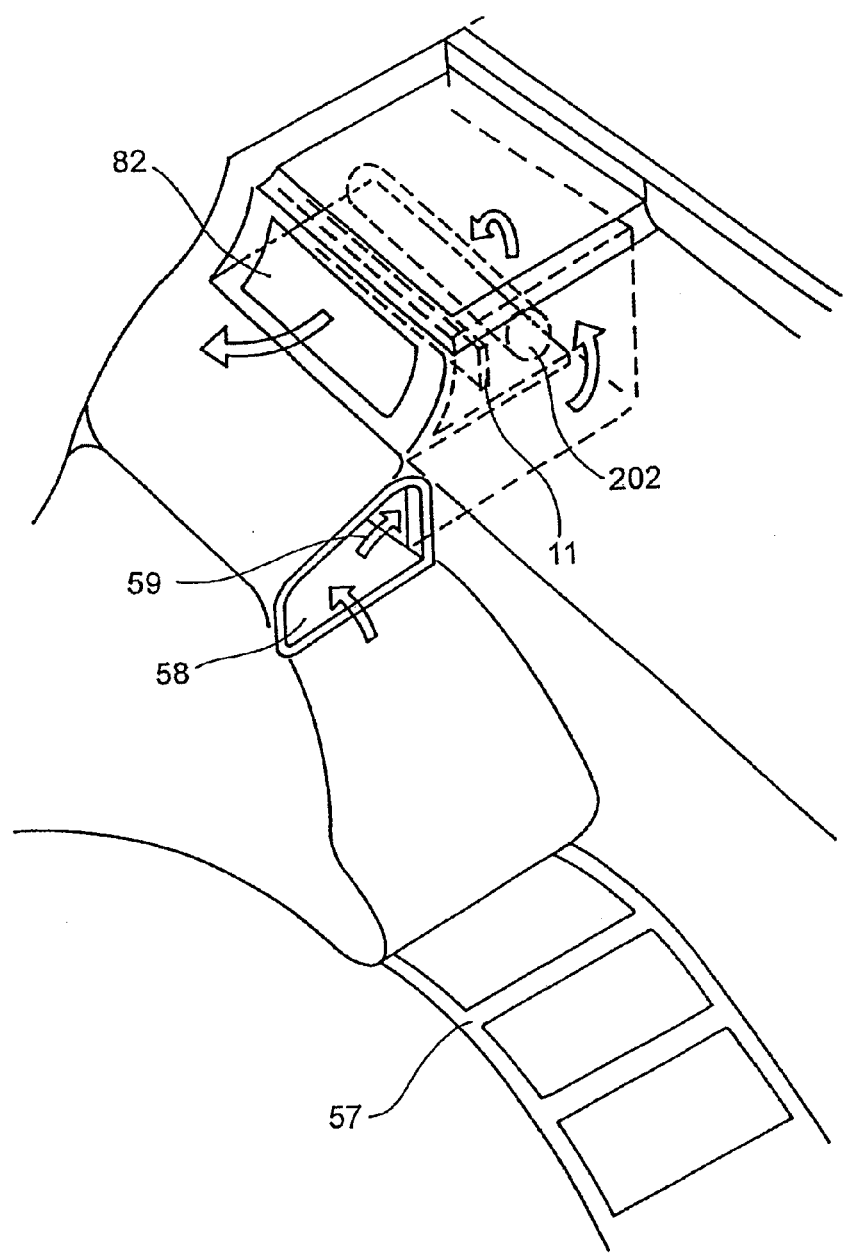
FIG. 41 is an enlarged view of a portion of the bypass passage and the ion generating electrode member of the air purifier.

FIG. 41 shows an enlarged view of a portion of the bypass passage 59 and the ion generating electrode member 202. The bypass passage 59 has a passage inlet 58 that is open toward the rotation direction of the fan 57, so that part of the air blown by the fan 57 is taken into the bypass passage 59 through the passage inlet 57. The bypass passage 59 first runs straight (in the rotation direction of the fan 57), then changes its course toward the front of the air purifier to run underneath the ion generating electrode member 202, and then charges its course upward to reach the ion generating electrode member 202.

In FIG. 38, in a portion of the front face of the body that faces the ion generating electrode member 202, the sight window 55 is provided to permit the user to check the operation status of the ion generating electrode member 202. On the surface of the sight window 55, a protection cover 40 is fitted to prevent air from leaking out from inside the air purifier. Preferably, this protection cover 40 is formed as part of a sheet that protects the whole front face of the body 50 including the sight window 55 (except for the housing 51) and that thus has an opening formed in a portion thereof that corresponds to the housing 51. For example, the sheet is made of a transparent resin material, and has a metallic silver color applied to or silk-screened on the back surface thereof. This gives the air purifier a massive look when seen from the front.

Making the front cover 70 see-through additionally, in combination with such coloring of the protection cover 40, gives the air purifier a refreshing, cleanly look.

Now, an example of how the air purifier operates will be described. When the power switch on the operation portion 54 is turned to the "on" position, the air purifier starts operating in an automatic mode. The motor 56 rotates the fan 57, and air is sucked into the air purifier through the inlet 71 and the side inlet 72 formed in the front cover 70. From the air, the prefilter 61 collects relatively large dust and other foreign particles, the deodorizing filter 62 absorbs and removes odors, and the dust collecting filter 63 collects relatively small dust and other foreign particles. The air, thus cleared of odors as well as dust and other foreign particles by the filter 60, is then discharged out of the air purifier by the fan 57. Meanwhile, part of the air is blown into the bypass passage 59 through the passage inlet 58 so as to be directed to the ion generating electrode member 202.

An alternating-current voltage of about 1.75 kV starts being applied to the ion generating electrode member 202 as soon as the air purifier starts operating. Thus, the ion generating electrode member 202 generates negative and positive ions from the air taken in, and also generates, as a byproduct, ozone simultaneously. Here, the negative and positive ions are generated in concentrations of 20,000 ions/cc, and the ozone in a concentration of 0.01 ppm or lower. By the action of the negative and positive ions thus generated simultaneously by the ion generating electrode member, airborne germs are removed from the air.

The concentrations of ions generated can be increased by increasing the alternating-current voltage applied to the ion generating electrode member 202. However, increasing the alternating-current voltage also increases the amount of ozone generated. To generate ions efficiently while minimizing the generation of ozone, it is advisable that the alternating-current voltage applied to the ion generating electrode member be 2.0 kV or lower. With the alternating-current voltage fulfilling this condition, it is possible to reduce the concentration of ozone down to $1/10$ or lower of the generally admitted maximum level (0.1 ppm). If the ion generating electrode member 202 is impregnated with an ozone decomposition catalyst, or a catalyst impregnated member 11 impregnated with an ozone decomposition catalyst is provided separately, it is possible to raise the upper limit of the applied voltage to 2.5 kV and thereby generate ions in higher concentrations.

Next, to evaluate the deodorization performance of the air purifier of this embodiment against odors in the air, the following experiment was conducted.

Example 21

The air purifier described above, incorporating the ion generating device 201 used in Example 10 described earlier, was installed in a test space 2.0 m long, 2.5 m wide, and 2.7 m high. After the atmosphere inside the test space was replaced with clean, dry air, five cigarettes were burned. Simultaneously, an alternating-current voltage of 1.1 kV rms having a frequency of 25 kHz was applied to the ion generating electrode member 202, and the motor 56 was activated to rotate the fan 57 at an air-flow rate of 4 $m^3$/sec, so that the air purifier started operating. Then, using a gas detector tube, the concentrations of ammonia, acetic acid, styrene, and carbon monoxide were measured at the time the air purifier started operating and 30 minutes thereafter. The experiment showed that 30 minutes' operation of the air purifier resulted in removal of 35% of the ammonia, 65% of the acetic acid, 58% of the styrene, and 90% of the carbon monoxide.

In this way, it was confirmed that the air purifier of this embodiment achieved satisfactory deodorization by quickly decomposing typical odors in households by the action of negative and positive ions.

Next, the sterilization performance of the air purifier of this embodiment against airborne germs will be described in terms of practical examples. It is to be understood, however, that the air purifier of this embodiment is not limited to the examples specifically described below, but may be implemented with modifications made in operating conditions and other factors as required.

Example 22

The air purifier described earlier, incorporating the ion generating device 201 used in Example 8 described earlier, was installed in a test space 2.0 m long, 2.5 m wide, and 2.7 m high. Then, common bacteria and fungi that had been cultured on a culture medium beforehand were sprayed in the test space. Simultaneously, the ion generating device 201 was put into operation under the same conditions as in Example 8 described earlier, and the motor 56 was started to rotate the blowing fan 57, so that the air purifier started operating.

Then, at predetermined time intervals, using an air sampler, model RCS manufactured by Biotest AG, Germany, the air inside the test space was extracted at a rate of 40 L/min and sampled for four minutes to measure the number of germs contained in the air. The results are shown in Table 8.

In two hours after the air purifier started operating, of the common bacteria and fungi that had originally been present in the test space, 77% and 80%, respectively, were removed. This proves that the air purifier of this embodiment, incorporating the ion generating device 201, is capable of satisfactorily killing most airborne germs by the action of the negative and positive ions that it blows out.

As described earlier in connection with the second and fifth embodiments, the air purifier 300 (see FIGS. 3 and 6) incorporating the ion generating electrode member 1 having a flat-plate-shaped glass plate 3 required three hours to kill and remove 70% or more of the germs inside the test space, as Example 3 (see Table 1) and Example 6 (see Table 3) exemplify. By contrast, the air purifier of this embodiment, incorporating the ion generating electrode member 202 having a cylindrical glass tube 203, requires one hour less. This proves superiority of the cylindrical glass tube 203.

Next, to check how much of the ozone that is generated inevitably together with the negative and positive ions in the space around the ion generating electrode member 202 is discharged through the outlet 81 of the air purifier by the blowing fan 57, the following experiment was conducted.

Example 23

Figure 42A:
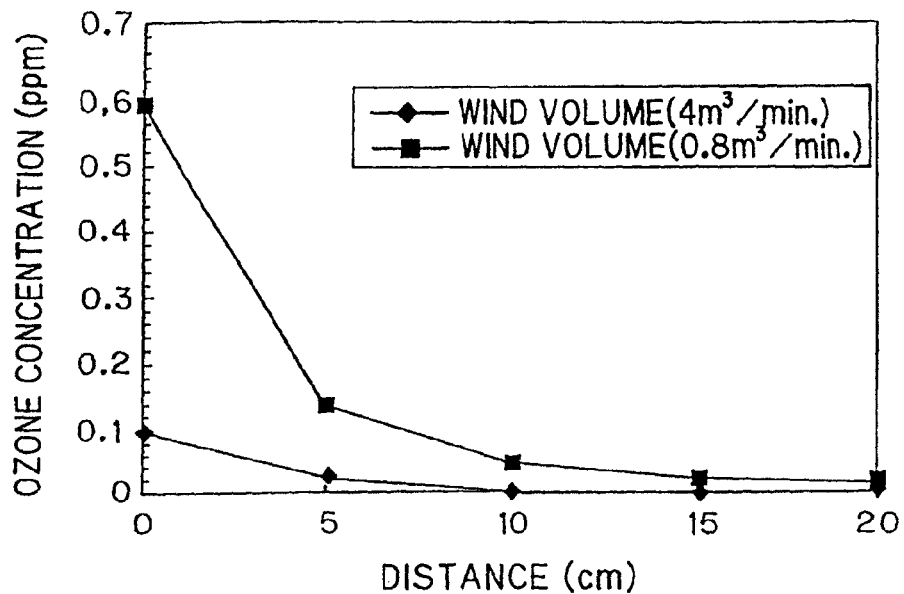
FIG. 42A is a graph showing the relationship between the concentration of the ozone generated by the ion generating electrode member and the distance from the outlet, as observed when an alternating-current voltage of 1.1 kV rms was applied to the ion generating electrode member and the blowing fan was driven in the air purifier.
Figure 42B:
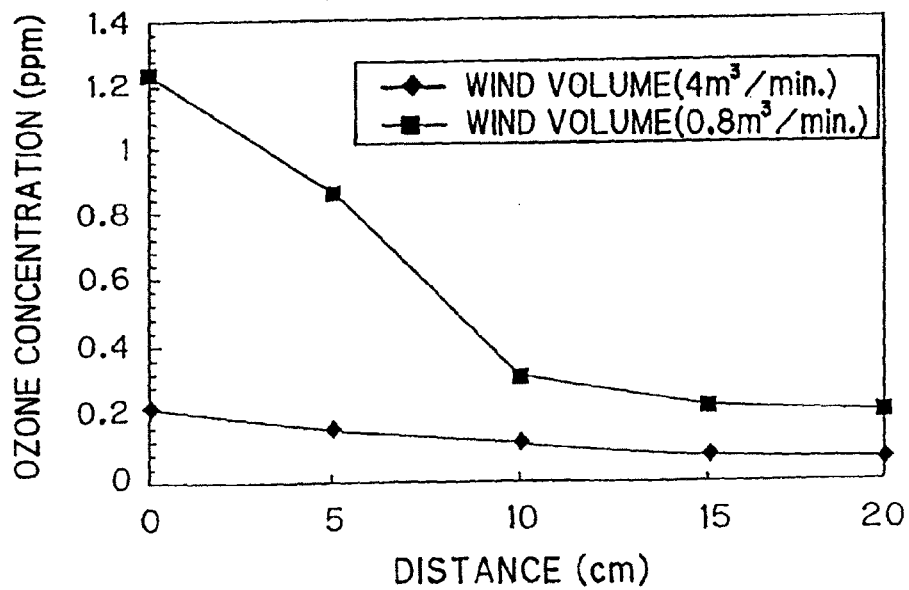
FIG. 42B is a graph showing the relationship between the concentration of the ozone generated by the ion generating electrode member and the distance from the outlet, as observed when an alternating-current voltage of 1.4 kV rms was applied to the ion generating electrode member and the blowing fan was driven in the air purifier.

An ozone concentration checker (not shown) was installed at each of five measurement points located 0 cm, 5 cm, 10 cm, 15 cm, and 20 cm away from the outlet 81 of the air purifier used in Example 22 described above. Then, an alternating-current voltage of 1.1 kV rms is applied to the ion generating electrode member 202, and the blowing fan 57 was started at an air-flow rate of 4 $m^3$/min or 0.8 $m^3$/min. In this state, the concentration of ozone was measured at each of the aforementioned measurement points. For comparison, with an alternating-current voltage of 1.4 kV rms applied under the same conditions, the concentration of ozone was measured in the same manner. The results in different cases are shown in FIGS. 42A and 42B. The concentration of ozone was measured using a UV absorption type ozone monitor, model EG-2001 manufactured by Ebara Jitsugyo Co., Ltd., Japan.

As shown in these figures, the higher the voltage applied, as expressed in an rms value, and the higher the air-flow rate at which the blowing fan 57 is driven, the higher the concentration of ozone. The concentration of ozone, however, drops quickly with the increasing distance from the outlet 81. Accordingly, by controlling the voltage applied, as expressed in an rms value, and the air-flow rate (i.e. the number of revolutions) at which the blowing fan 57 is driven, it is possible to control the amount of ozone that is generated as a byproduct by the ion generating electrode member 202.

Thus, an ozone sensor (not shown) may be additionally provided in the vicinity of the ion generating electrode member 202 to continually monitor the concentration of ozone, and the air purifier may be so configured that, according to the results of the detection by the ozone sensor, the high alternating-current voltage, as expressed in an rms value, applied to the ion generating electrode member 202 is determined in such a way as to keep the concentration of ozone below a predetermined admitted level.

This makes it possible to realize an air purifier that can kill and remove airborne germs by the action of negative and positive ions while keeping the concentration of the ozone generated by the ion generating electrode member 202 below an admitted level. As the aforementioned admitted level of the concentration of ozone, it is proper to use the level 0.1 ppm stipulated by Japan Society for Occupational Health.

Figure 43:
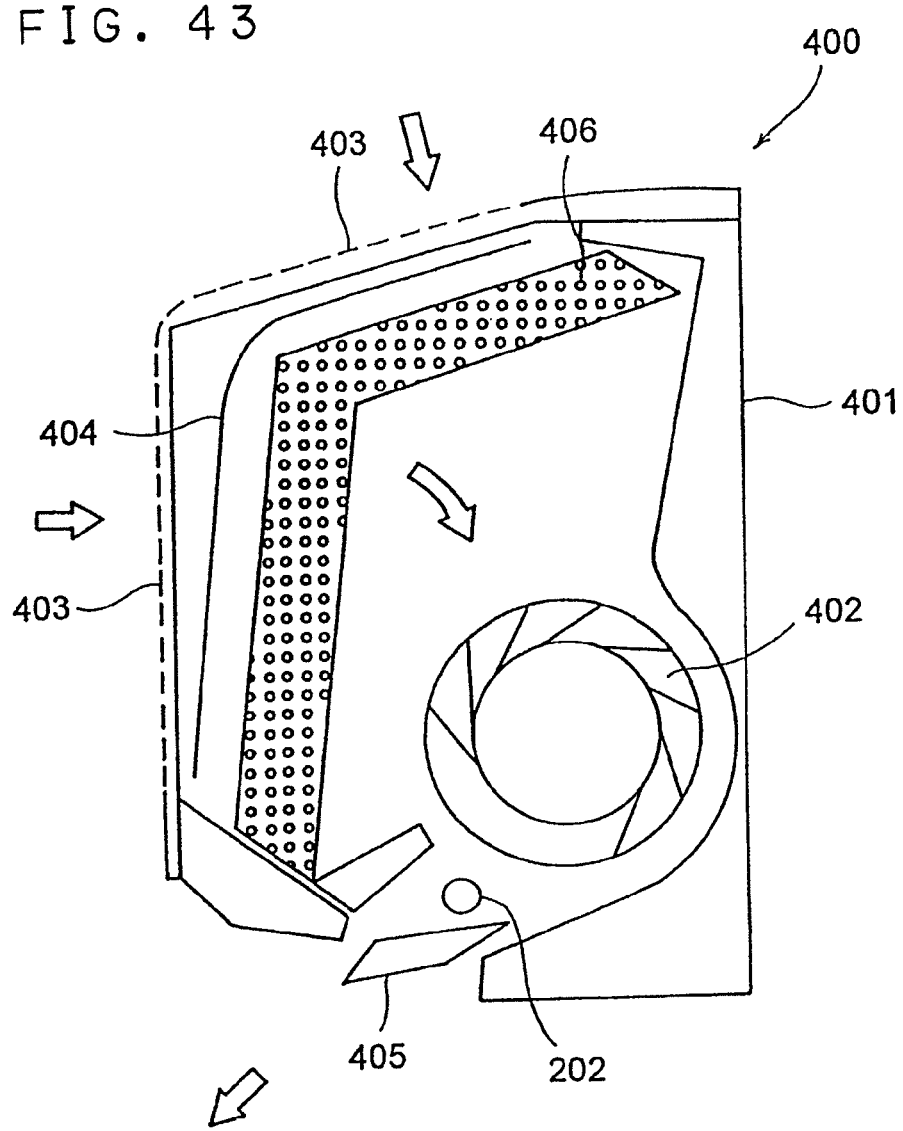
FIG. 43 is a sectional view showing the outline of the structure of the air conditioner, incorporating an ion generating electrode member, of a tenth embodiment of the invention.

Now, a tenth embodiment of the invention will be described with reference to the drawings. FIG. 43 is a sectional view showing the outline of the structure of the air conditioner 400, incorporating an ion generating electrode member 202, of a tenth embodiment of the invention.

In a rear portion inside the body 401 of the air conditioner 400, a blowing fan 402 is provided. In the front and top faces of the body 401, an air inlet 403 is formed that consists of a number of holes or slits. On the downstream side of the inlet 403, various filters 404 for dust removal and deodorization are provided. On the downstream side of the filters 404, a heat exchanger 406 is provided. Below the inlet 403 of the body 401, an air outlet 405 is formed that is provided with a louver for adjusting the direction of the air blown out. In this way, an air flow passage leading from the inlet 403 to the filters 404, then to the heat exchanger 406, and then to the outlet 405 is formed inside the body 401.

Moreover, the ion generating device 201 (see FIG. 8) of the seventh embodiment described earlier is arranged with its ion generating electrode member 202 placed in the air flow passage, in the vicinity of the outlet 405. Here, the high alternating-current voltage source 206 (see FIG. 8) may be provided separately from a power source for driving the blowing fan 402, or may be shared for this purpose also. In the latter case, a controller (not shown) is additionally provided so that the driving of the blowing fan 402 and of a compressor (not shown) and the operation of the ion generating device 201 can be controlled independently. This permits the ion generating device 201 to be turned on and off as required while the air conditioner 400 is operating, and thus enhances the usability of the air conditioner 400.

When this air conditioner 400, structured as described above, starts operating, the blowing fan 402 starts rotating. As a result, the air sucked through the inlet 403 into the air flow passage is passed through the filters 404, which remove dust and odors from the air, is then passed through the heat exchanger 406, which exchanges heat between the air and a cooling medium, and is then blown out through the outlet 405.

Meanwhile, if the ion generating device 201 is kept on, the negative and positive ions generated in the space around the ion generating electrode member 202 are blown out together with the clean air. In this way, it is possible to kill airborne germs by the action of negative and positive ions.

Next, the sterilization performance of the air conditioner 400 of this embodiment against airborne germs will be described in terms of a practical example. It is to be understood, however, that the air conditioner 400 of this embodiment is not limited to the example specifically described below, but may be implemented with modifications made in operating conditions and other factors as required.

Example 24

The air conditioner 400 described above, incorporating the ion generating device 201 used in Example 8 described earlier, was installed in a test space 2.0 m long, 2.5 m wide, and 2.7 m high. Then, common bacteria and fungi that had been cultured on a culture medium beforehand were sprayed in the test space. Simultaneously, the ion generating device 201 was put into operation under the same conditions as in Example 8 described earlier, and the blowing fan 402 was started, so that the air conditioner 400 started operating.

Then, at predetermined time intervals, using an air sampler, model RCS manufactured by Biotest AG, Germany, the air inside the test space was extracted at a rate of 40 L/min and sampled for four minutes to measure the number of germs contained in the air. The results are shown in Table 9.

In two hours after the air conditioner 400 started operating, of the common bacteria and fungi that had originally been present in the test space, 80% and 83%, respectively, were removed. This proves that the air conditioner 400 of this embodiment, incorporating the ion generating device 201, is capable of satisfactorily killing most airborne germs by the action of the negative and positive ions that it blows out.

As described earlier in connection with the second and fifth embodiments, the air conditioner 400 (see FIGS. 4 and 7) incorporating the ion generating electrode member 2 having a flat-plate-shaped glass plate 3 required three hours to kill and remove 70% or more of the germs inside the test space, as Example 4 (see Table 2) and Example 7 (see Table 4) exemplify. By contrast, the air conditioner 400 of this embodiment, incorporating the ion generating electrode member 202 having a cylindrical glass tube 203, requires one hour less. This proves superiority of the cylindrical glass tube 203.

In the air conditioner 400 described above, the ion generating electrode member 202 is placed in the air flow passage formed inside the body. Thus, when the air conditioner is operating, the ion generating electrode member 202, by being exposed to air containing dust, tends to collect dust on its surface. In particular, when the air conditioner is operating in a cooling or dehumidifying mode, the moisture in the air is likely to condense on the surface of the ion generating electrode member 202. If a foreign substance such as dust or dew attaches to the electrodes, abnormal electric discharge or leakage current is likely to result. This is undesirable because it lessens the safety of the air conditioner 400.

Figure 44:
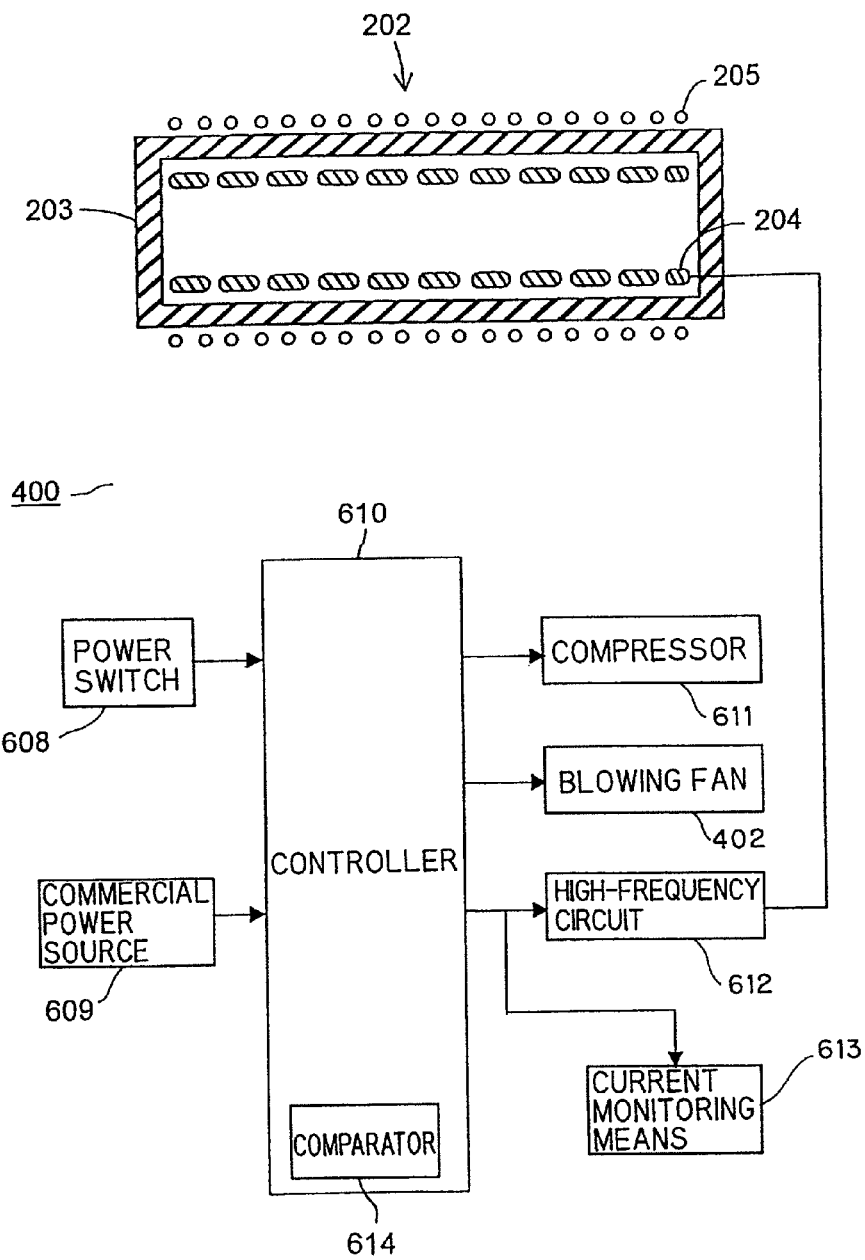
FIG. 44 is a block diagram showing the basic configuration of the controller of the air conditioner, incorporating an ion generating device, of an eleventh embodiment of the invention.

Now, an eleventh embodiment of the invention will be described with reference to the drawings. FIG. 44 is a block diagram showing the basic configuration of the controller of the air conditioner 400, incorporating an ion generating device 201, of an eleventh embodiment of the invention. In this figure, such members as are found also in the air conditioner 400 (see FIG. 43) of the tenth embodiment described above are identified with the same reference numerals.

As shown in FIG. 44, the input side of a controller 610 including a comparator 614 is connected to a power switch 608 and to a commercial power source 609, from which electric power is supplied to the controller 610 when the power switch 608 is operated. The output side of the controller 610 is connected to a compressor 611 and the blowing fan 402 of the air conditioner, and also through a high-frequency circuit 612 to the inner electrode 204 of the ion generating electrode member 202. Reference numeral 613 represents a current monitoring means for monitoring the current fed from the controller 610 to the high-frequency circuit 612. The result of the monitoring by the current monitoring means 613 is fed to the comparator 614.

Now, how this air conditioner configured as described above is used will be described. When the power switch 608 is turned on, electric power is fed from the commercial power source 609 to the controller 610. The controller 610 then energizes the compressor 611 and the blowing fan 402 to drive them, and also energizes the high-frequency circuit 612 so that the high-frequency circuit 612 applies an alternating-current voltage to the inner electrode 204.

As a result, by the action of the blowing fan 402, indoor air is sucked in through the inlet 403, is then passed through the filter 404, which removes dust and odors from the air, and is then passed through the heat exchanger 406, which exchanges the heat of the air, so that cooled or heated air is discharged through the outlet 405 into the room. Simultaneously, the ion generating electrode member 202 generates negative and positive ions, and an active species having a sterilizing effect is blown out into the room together with the air. This, in combination with proper air conditioning, realizes a comfortable living environment.

Example 25

In the air conditioner 400 configured as described above, an alternating-current voltage of 1.6 kV rms having a frequency of 20 kHz was applied to the ion generating electrode member 202, in which the glass tube 203 had an external diameter of 20 mm, was 150 mm long, and was 1.2 mm thick, the inner electrode 204 was woven from wire 0.18 mm across, was 80 mm long, and had 40 meshes/inch, and the outer electrode 205 was woven from wire 0.4 mm across, was 80 mm long, and had 16 meshes/inches. As a result, at a measurement point located 10 cm away from the side surface of the glass tube 203, negative and positive ions were obtained in concentrations of 30,000 to 40,000 ions/cc. Here, the current flowing through the outer electrode 205 was 1.2 mA. The concentrations of ions were measured using an airborne ion counter, model 83-1001B manufactured by Dan Kagaku Co., Ltd., Japan.

In this way, as long as the ion generating device 601 is operating normally, when the high-frequency circuit 612 is applying the alternating-current voltage to the inner electrode 204, the current flowing through the outer electrode 205 is as feeble as several milliamperes. However, if a foreign substance such as dust attaches to the ion generating electrode member 202, or if the glass tube 203 develops a breakage, a short circuit may occur locally between the inner and outer electrodes 204 and 205, causing a relatively high current to flow.

Such a short circuit not only makes it impossible to obtain a sufficient amount of ions to achieve satisfactory sterilization, but also shortens the life and degrades the performance of the ion generating electrode member 202. Moreover, if a person touches the glass tube 203, electric discharge may occur between the inner electrode 204 and the person's body. This causes a current to flow through the body, which is at the ground potential, and thus poses a risk of giving the person an electric shock.

To avoid this, when the high-frequency circuit 612 is applying the alternating-current voltage to the inner electrode 204, the current that flows from the controller 610 to the high-frequency circuit 612 is monitored with the current monitoring means 613. The result of this monitoring is fed to the comparator 614 included in the controller 610. The comparator 614 then compares the result fed thereto with a predetermined reference level and, if the result is higher than the reference level, the controller 610 de-energizes the high-frequency circuit 612.

Even when the air conditioner 400 is operating normally, the current may be as high as 50 mA at the maximum, depending on the environment in which it is used. On the other hand, it is known that a current of 100 mA or higher flowing through a human body is very likely to be fatal. Accordingly, it is proper to determine the reference level for the current within the range 50 to 100 mA.

This makes it possible to stop the application of the alternating-current voltage to the inner electrode 204 in case of trouble, and thereby prevent malfunctioning or failure of the ion generating device 601. In this way, it is possible to prolong the life of the ion generating electrode member 202 and prevent degradation of its performance, and to realize a safe air conditioner 400 that poses no risk of an electric shock even if a person accidentally touches the ion generating electrode member 202 from outside. In this embodiment, the power switch 608 is shared as a switch for starting the air conditioner 400; however, it is also possible to provide separate switches for these purposes so that the air conditioner 400 and the ion generating device 601 can be controlled independently.

Figure 45:
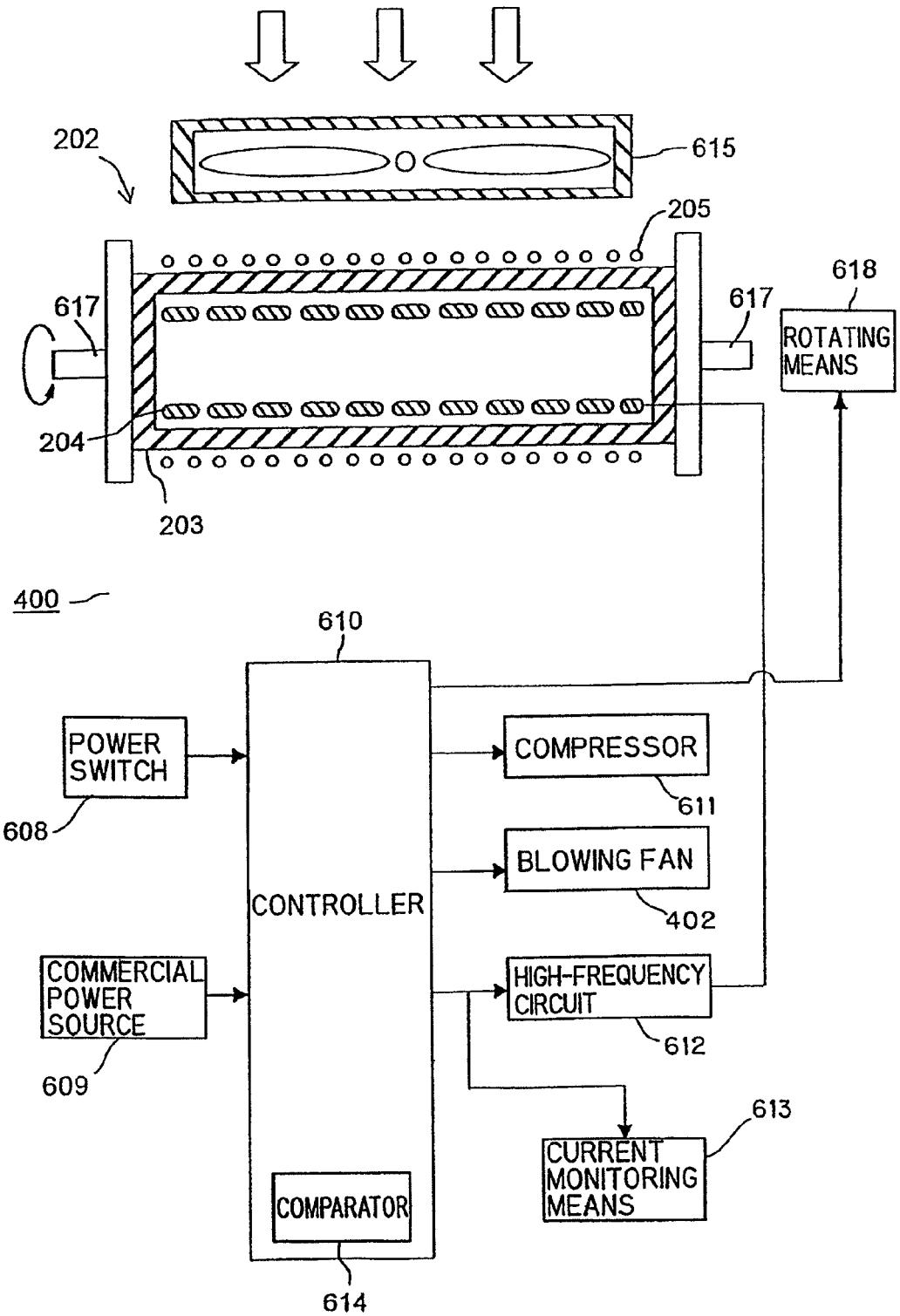
FIG. 45 is a block diagram showing the basic configuration of the controller of the air conditioner, incorporating an ion generating device, of a twelfth embodiment of the invention.

Now, a twelfth embodiment of the invention will be described with reference to the drawings. FIG. 45 is a block diagram showing the basic configuration of the controller of the air conditioner 400, incorporating an ion generating device 201, of a twelfth embodiment of the invention. In this figure, such members as are found also in the air conditioner 400 of the eleventh embodiment described above and shown in FIG. 44 are identified with the same reference numerals.

In this embodiment, the ion generating electrode member 202 is rotatable, and the air conditioner 400 is additionally provided with a rotary shaft 617 for rotating the ion generating electrode member 202, a rotating means 618 for rotating the rotary shaft 617, and a blowing element 615 serving as a foreign substance removing means. In other respects, the arrangement of this embodiment is the same as that of the eleventh embodiment described above.

The rotating means 618 and the bowing element 615 are connected to the controller 610, which controls their operation. Specifically, when the current being monitored by the current monitoring means 613 exceeds a predetermined level (for example, 200 mA), the rotating means 618 and the blowing element 615 are activated so that the ion generating electrode member 202 is rotated, and is blown with air.

In this way, it is possible to blow off the dust collected on the ion generating electrode member 202 and evaporate the dew condensed thereon. This helps prevent leakage current resulting from condensed dew and abnormal electric discharge resulting from collected dust. Moreover, it is possible to keep the ion generating electrode member 202 without maintenance.

Figure 46:
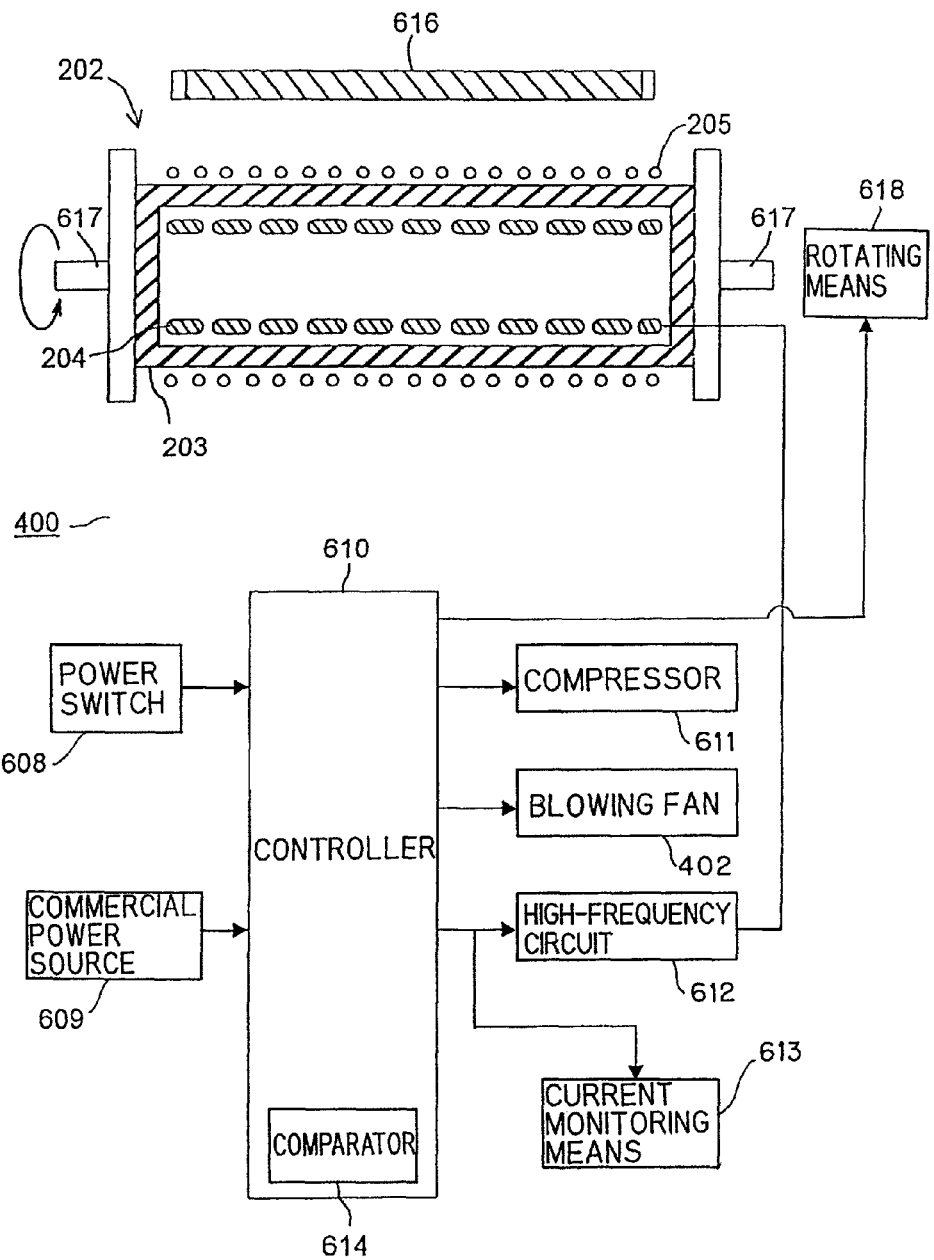
FIG. 46 is a block diagram showing the basic configuration of the controller of the air conditioner, incorporating an ion generating device, of a thirteenth embodiment of the invention.

Now, a thirteenth embodiment of the invention will be described with reference to the drawings. FIG. 46 is a block diagram showing the basic configuration of the controller of the air conditioner 400, incorporating an ion generating device 601, of a thirteenth embodiment of the invention. In this figure, such members as are found also in the air conditioner 400 of the eleventh embodiment described earlier and shown in FIG. 44 are identified with the same reference numerals.

In this embodiment also, the ion generating electrode member 202 is rotatable, and the air conditioner 400 is additionally provided with a rotary shaft 617, a rotating means 618, and a heating element 616 serving as a foreign substance removing means. In other respects, the arrangement of this embodiment is the same as that of the tenth embodiment described earlier.

The rotating means 618 and the heating element 616 are connected to the controller 610, which controls their operation. Specifically, when the current being monitored by the current monitoring means exceeds a predetermined level (for example, 200 mA), the rotating means 618 and the heating element 616 are activated so that the ion generating electrode member 202 is rotated, and is heated.

In this way, it is possible to evaporate the dew condensed all over the electrodes of the ion generating electrode member 202. This helps prevent leakage current resulting from condensed dew. Moreover, it is possible to operate the ion generating device 601 to generate negative and positive ions without causing leakage current.

The arrangements described above may be applied to air conditioning apparatus of any kind, such as air purifiers, dehumidifiers, and humidifiers, to gain similar advantages. It is also possible to design another arrangement by combining the desired features of different embodiments.

The ion generating device 201 of the present invention can be built as a unit so that it can easily be attached to and detached from various air conditioning apparatus such as air conditioners. This enhances the usability of those air conditioning apparatus and makes their maintenance, such as cleaning and repair, far easier.

Figure 47:
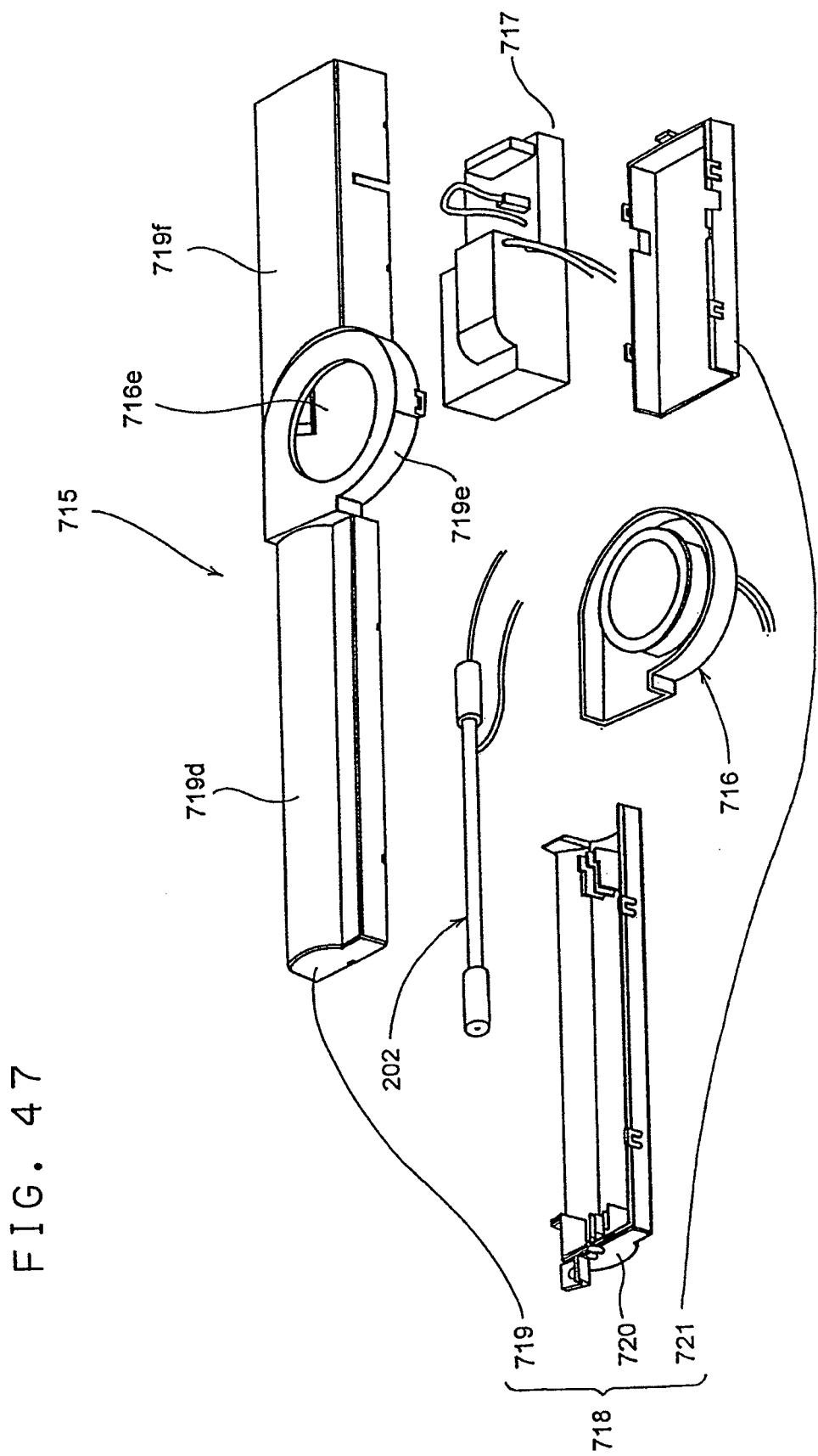
FIG. 47 is an exploded perspective view of the ion generating device unit of a fourteenth embodiment of the invention.
Figure 48:
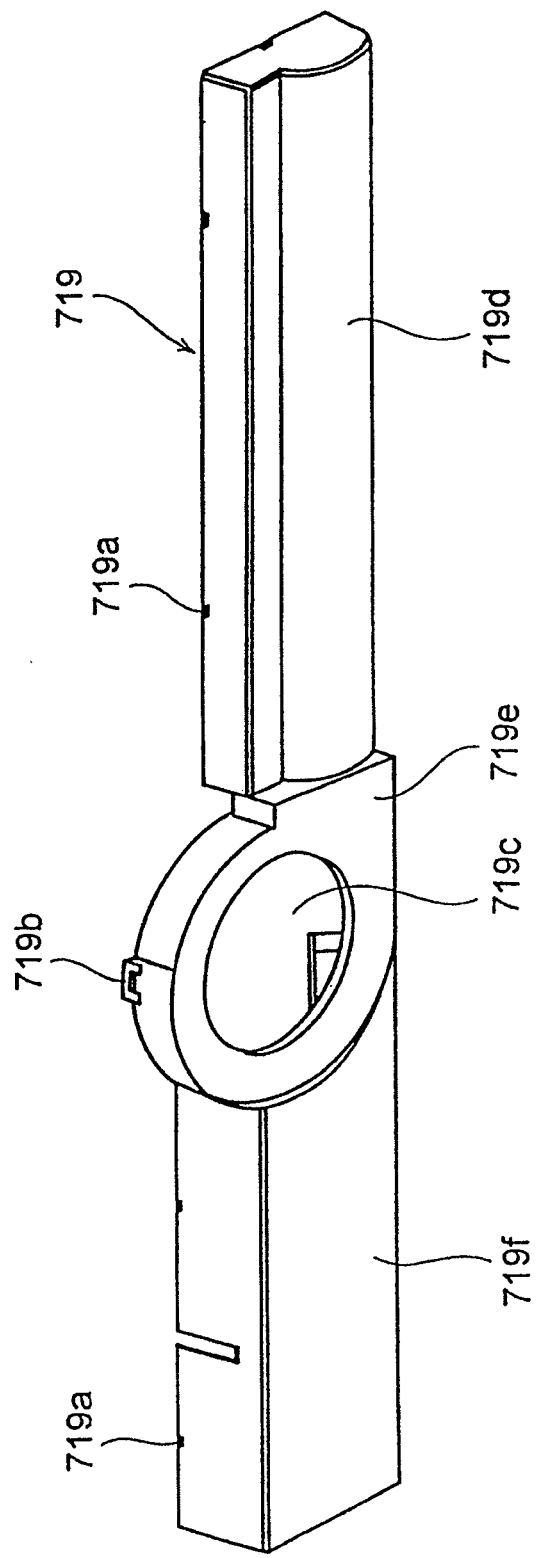
FIG. 48 is a perspective view of the front member of the ion generating device unit.
Figure 49A:
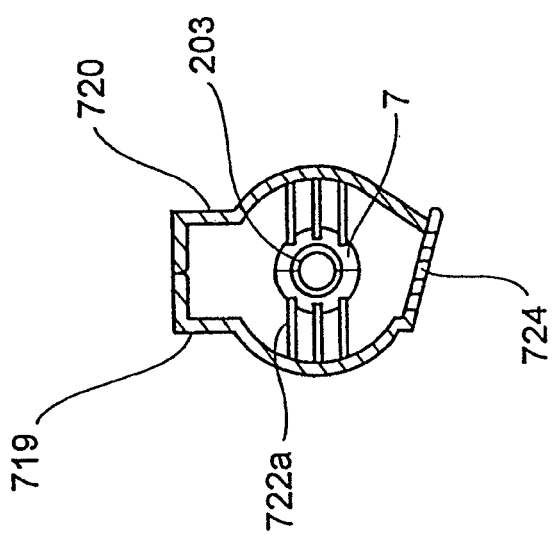
FIG. 49A is a sectional view showing how the ion generating electrode member is fitted in the ion generating device unit.
Figure 49B:
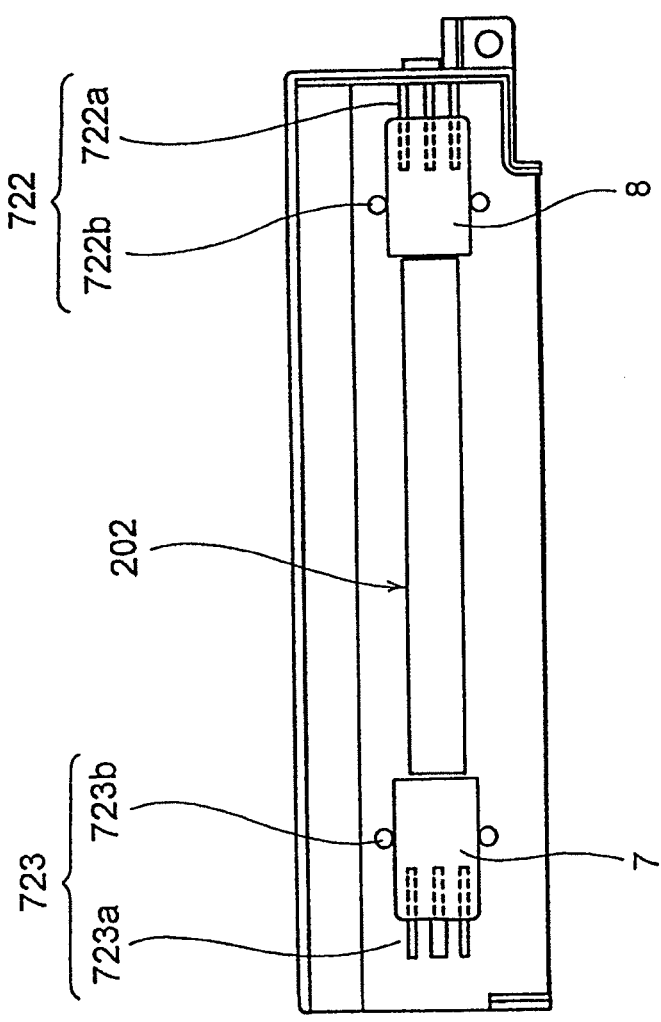
FIG. 49B is an exposed front view showing how the ion generating electrode member is fitted.
Figure 50:
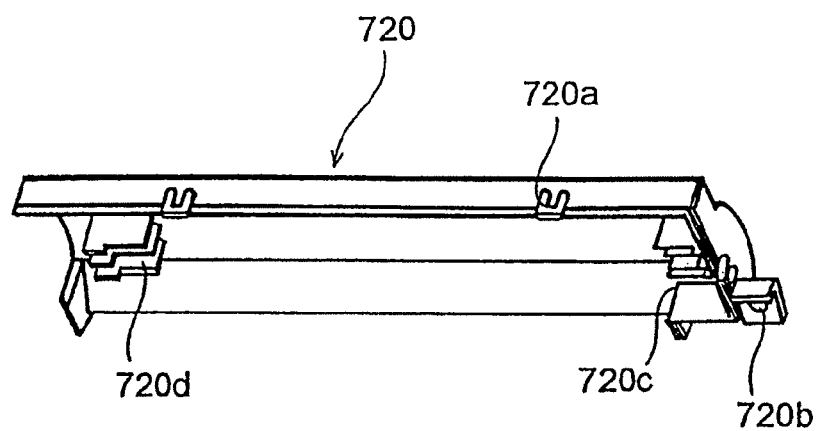
FIG. 50 is a perspective view of the rear left-hand member of the ion generating device unit.
Figure 51:
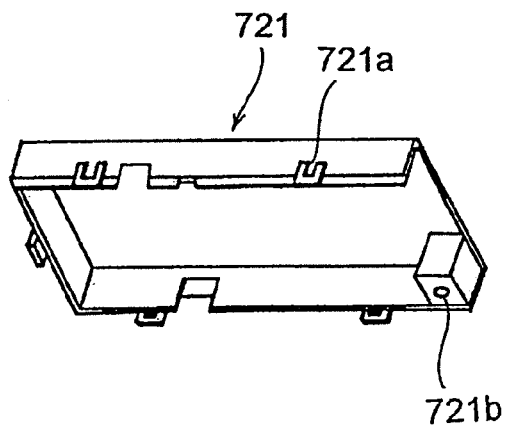
FIG. 51 is a perspective view of the rear right-hand member of the ion generating device unit.
Figure 52:
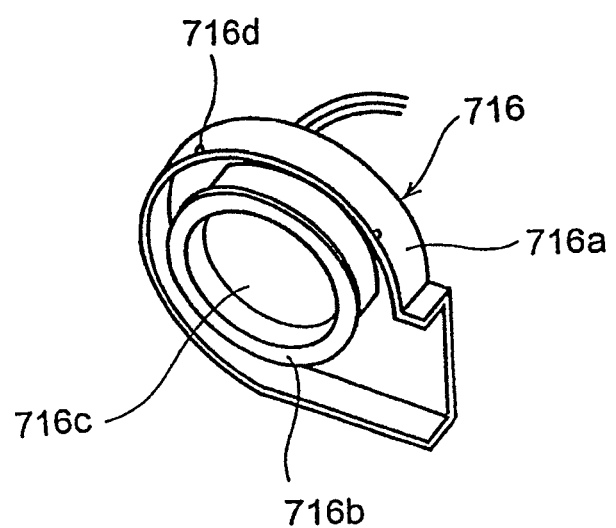
FIG. 52 is a perspective view of the sub blower unit of the ion generating device unit.

Now, a fourteenth embodiment of the invention will be described with reference to the drawings. FIG. 47 is an exploded perspective view of the ion generating device unit 715 of a fourteenth embodiment of the invention. FIG. 48 is a perspective view of the front member 719 of the ion generating device unit 715. FIG. 49A is a sectional view showing how the ion generating electrode member 202 is fitted in the ion generating device unit 715. FIG. 49B is an exposed front view showing how the ion generating electrode member 202 is fitted. FIG. 50 is a perspective view of the rear left-hand member 720 of the ion generating device unit 715. FIG. 51 is a perspective view of the rear right-hand member 721 of the ion generating device unit 715. FIG. 52 is a perspective view of the sub blower unit 716 of the ion generating device unit 715.

As shown in FIG. 47, the ion generating device unit 715 of this embodiment is composed of the ion generating electrode member 202 of the ion generating device 201 (see FIG. 8) of the seventh embodiment describe earlier, a sub blower unit 716, a driver circuit unit 717, and a unit body 718.

The sub blower unit 716 is structured as shown in FIG. 52. The sub blower unit 716 takes in air and blows it onto the ion generating electrode member 202, and also blows out the negative and positive ions generated. The sub blower unit 716 is composed of a casing 716*a* having a fan 716*b* and a motor 716*c* housed therein. On the joint surface of the casing 716*a*, a plurality of projections 716*d* are formed that fit into hoops 719*b* (see FIG. 48).

In this ion generating device unit 715, the front face is where the inlet 716*e* (see FIG. 47) of the sub blower unit 716 is located, and the back face is the face opposite thereto. That is, as the sub blower unit 716 operates, it sucks in air toward the back side thereof. The following descriptions assume that the direction in which the sub blower unit 716 blows out the air (i.e. the direction in which the sub blower unit 716 finds the ion generating electrode member 202 placed) is leftward, and that the direction opposite thereto is rightward.

The unit body 718 is composed of a front member 719, a rear left-hand member 720, and a rear right-hand member 721.

As shown in FIG. 48, the front member 719 consists of an ion generator housing portion 719*d* for housing the ion generating electrode member 202, a casing portion 719*e* for the sub blower unit 716, and a circuit housing portion 719*f* for housing the driver circuit unit 717 for driving the ion generating device unit 715, with all these three portions formed integrally. The front member 719 as a whole has a concave shape, and on the outside thereof, near the joint surface, are formed a plurality of locking hoops 719*b* for locking the sub blower unit 716 and a plurality of locking projections 719*a* for locking the rear left-hand member 720 and the rear right-hand member 721.

As shown in FIG. 49A, the ion generator housing portion 719*d* is so shaped as to have, as a part of the cross section thereof, arc-shaped curves. On the inner surfaces of those curved portions of the ion generator housing portion 719*d*, support portions 722 and 723 for supporting and holding the ion generating device unit 715 are formed at the left-hand and right-hand ends thereof, and, below the left-hand and right-hand support portions 722 and 723, an ion outlet 724 is provided through which the air that has passed through the ion generating electrode member 202 is blown out. By making the passage from the ion generating electrode member 202 to the ion outlet 724 as short as possible and in addition minimizing the volume of the ion generator housing portion 719*d* in this way, it is possible to reduce the air resistance of the passage and reduce the loss in the amount of negative and positive ions in the air. This makes it possible to discharge a stable amount of negative and positive ions.

As shown in FIG. 49B, each of the support portions 722 and 723 consists of three ribs 722*a* or 723*a* that together form a curved surface so as to hold the peripheral surface of the stopping member 7 or 8 of the ion generating electrode member 202, and bosses 722*b* or 723*b* that keep the stopping member 7 or 8 in position vertically. The ribs 722*a* and 723*a* and the bosses 722*b* and 723*b* are so formed as to protrude from the inner surfaces of the front member 719 and the rear left-hand member 720. Moreover, the ribs 722*a* and 723*a* have portions thereof formed higher than their portions forming the curved surfaces so as to hold the end surfaces of the stopping members 7 and 8 of the ion generating electrode member 202 and keep them in position laterally.

The ion outlet 724 is, for example, so shaped as to consist of three columns×three rows of small slit holes each 3 mm×50 mm. These slit holes make it difficult for a foreign body to be inserted through the ion outlet 724 to reach the ion generating electrode member 202.

In the casing portion 719*e*, a wall that serves as a casing for the fan of the sub blower unit 716 is formed so as to describe an involute curve. Along the free-end edge of the wall, a plurality of locking hoops 719*b* for locking the motor-side casing are formed. In the flat portion of the casing portion 719*e*, a sub blower inlet 719*c* through which air is sucked in is formed.

Inside the circuit housing portion 719*f*, a wall is formed so as to form a concave shape. Along the free-end edge of the wall, a plurality of projections 719*a* for locking the rear right-hand member 721 are formed. Moreover, an H-shaped rib for supporting a case incorporating the circuit board of the driver circuit is provided so as to protrude inward from outside. On the outside of the H-shape rib, hoops for locking the ion generating device unit 715 are formed.

The rear left-hand member 720 shown in FIG. 50 is for covering the ion generating device housing portion. On the inner surface of the rear left-hand member 720, support portions 720c and 720d forming partial curved surfaces for supporting and holding the ion generating electrode member 202 are formed at the left-hand and right-hand ends. Specifically, three R-shaped ribs for holding the peripheral surfaces of the stopping members 7 and 8 of the ion generating electrode member 202 are so formed as to protrude from the inner surface of the rear left-hand member 720. These R-shaped ribs have portions thereof formed higher than their portions forming the curved surfaces so as to hold the stopping members 7 and 8 to keep them in position laterally.

On the periphery of the rear left-hand member 720, along the joint surface, a plurality of hoops 720a for locking the front member 719 are formed. In the side wall of one of the support portions, a slit hole is formed through which leads are laid, and, in the side wall of the other of the support portions, a hole 720b for fixing the ion generating device unit 715 is formed.

The rear right-hand member 721 shown in FIG. 51 is for covering the circuit housing portion. Inside the rear right-hand member 721, a wall is formed so as to form a concave shape. Along the free-end edge of the wall, a plurality of hoops 721a with which the projections 719a of the front member 719 engage are formed. Moreover, at one open end of the wall, a hole 721b for fixing the ion generating device unit 715 is formed.

The ion generating device unit 715 structured as described above is assembled in the following manner. The sub blower unit 716 is inserted in a predetermined position in the casing portion 719e of the front member 719, and is fixed by inserting the projections 716d of the casing 716a into the locking hoops 719b of the front member 719. Then, the driver circuit unit 717 is inserted in a predetermined position in the driver circuit unit portion 719f of the front member 719, and the rear right-hand member 721 is placed over the driver circuit unit 717 and is fixed by inserting the locking projections 719a of the front member 719 into the hoops 721a of the rear right-hand member 721. Then, the ion generating electrode member 202 is inserted in a predetermined position in the ion generating device housing portion 719d, and the rear left-hand member 720 is placed over the ion generating electrode member 202 and is fixed by inserting the projections 719a of the front member into the hoops 20d of the rear left-hand member 720. This completes the assembly. In this way, simply by mounting the ion generating electrode member 202 on the support portions of the front member 719 and then placing the rear left-hand member 720 so as to cover it, it is possible to fix the ion generating electrode member 202 as a result of the support portions of the rear left-hand member 720 holding it. This helps keep the ion generating electrode member 202 in position during assembly. Moreover, the disuse of screws makes disassembly and assembly easy.

Figure 53:
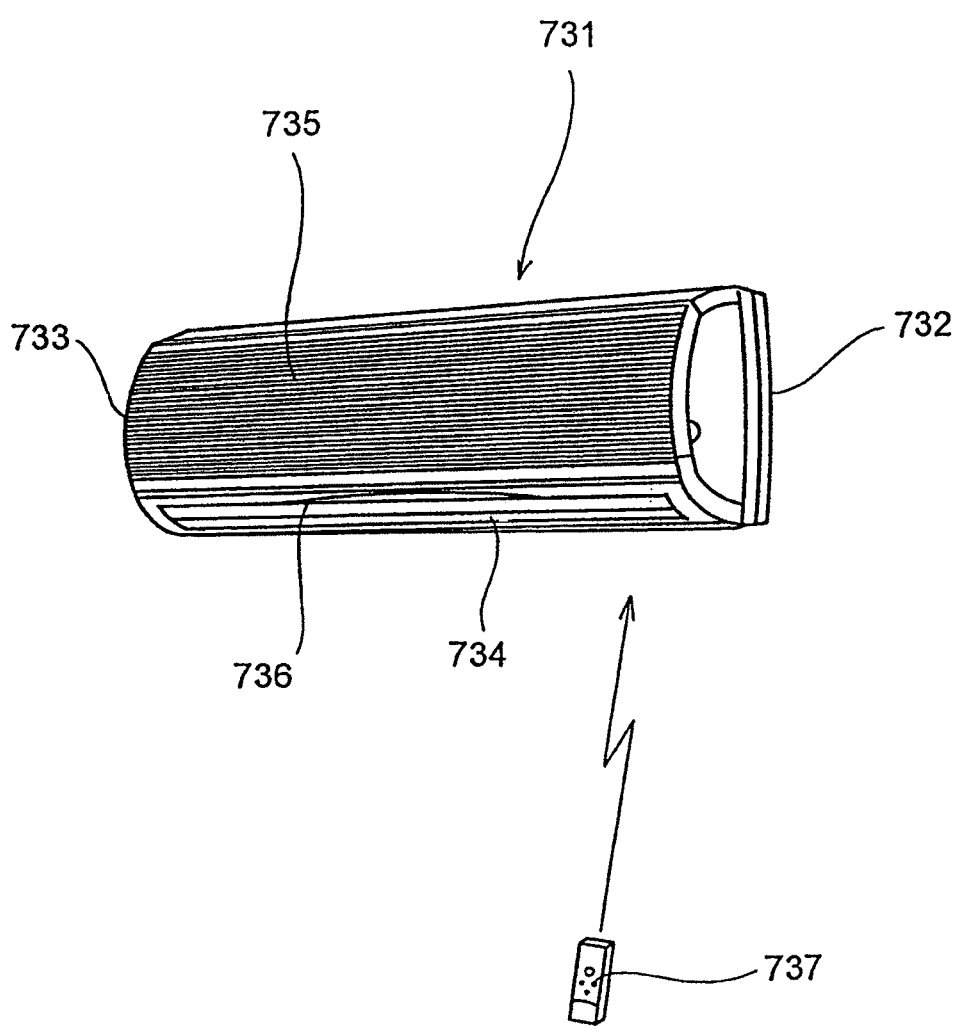
FIG. 53 is a front perspective view showing an outline of the structure of the air conditioner, incorporating an ion generating device unit, of a fifteenth embodiment of the invention.
Figure 54:
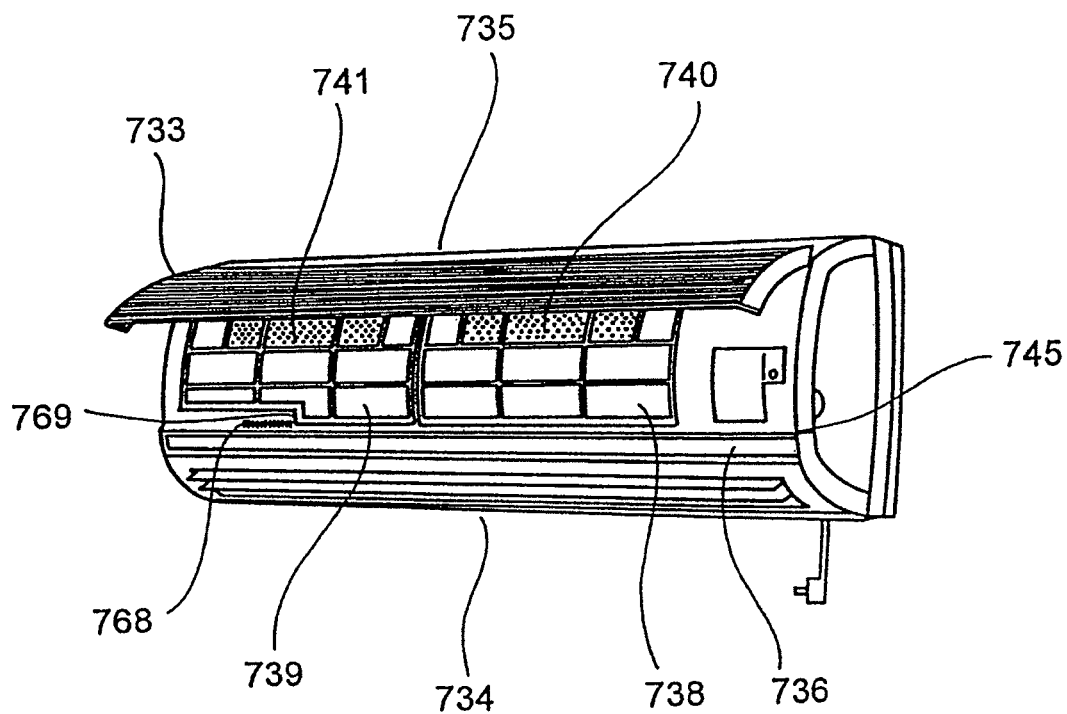
FIG. 54 is a front perspective view of the air conditioner, with its front panel opened.
Figure 55:
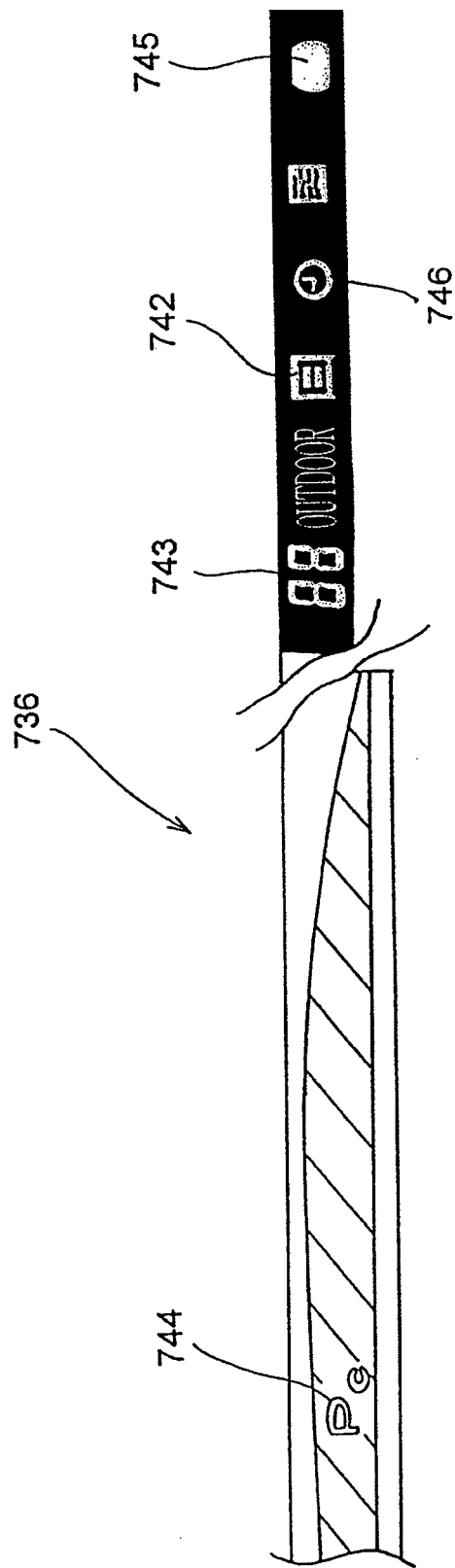
FIG. 55 is an enlarged front view of the display device provided on the body of the air conditioner.
Figure 56:
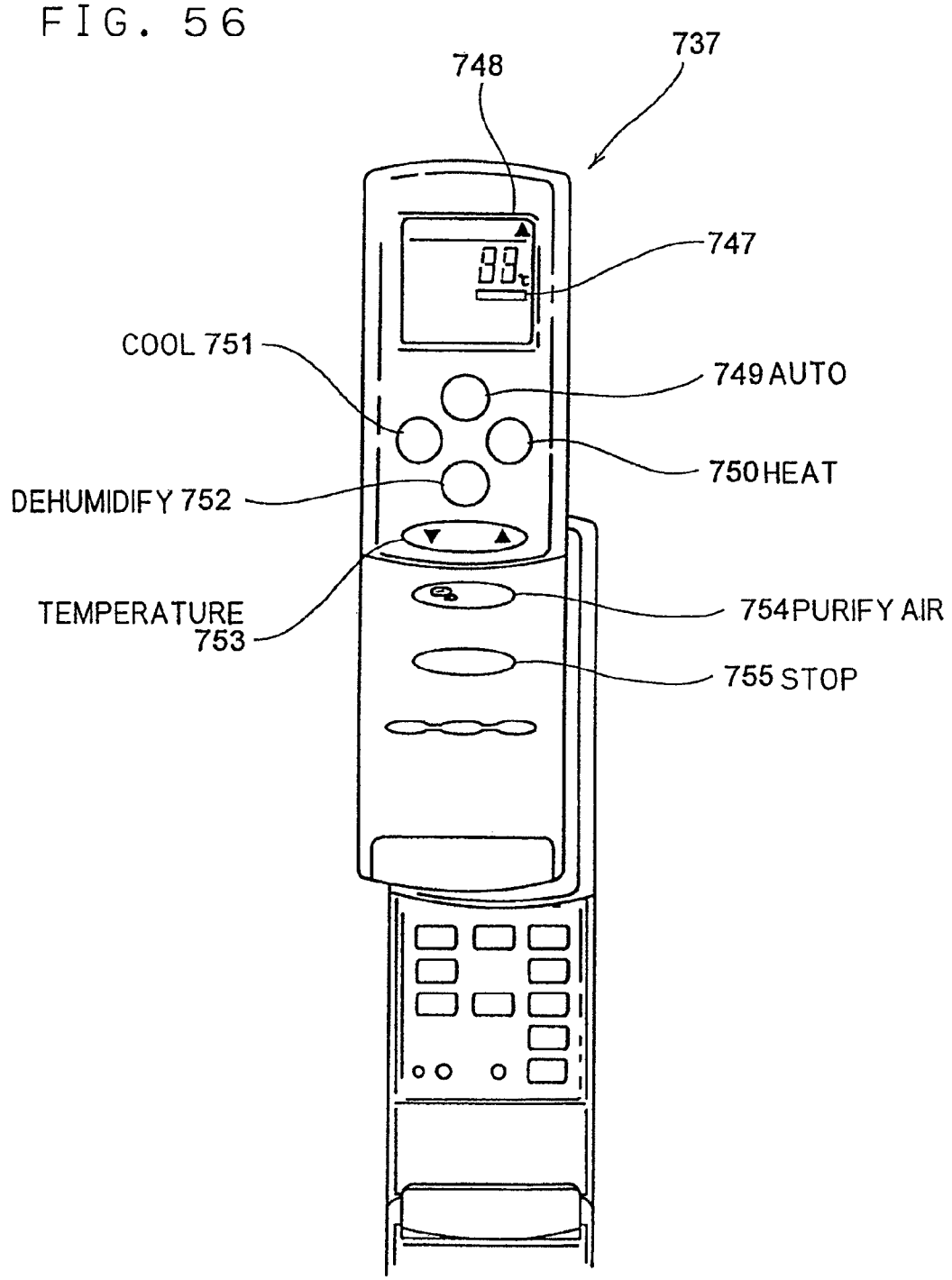
FIG. 56 is a perspective view of the remote control unit of the air conditioner.
Figure 57:
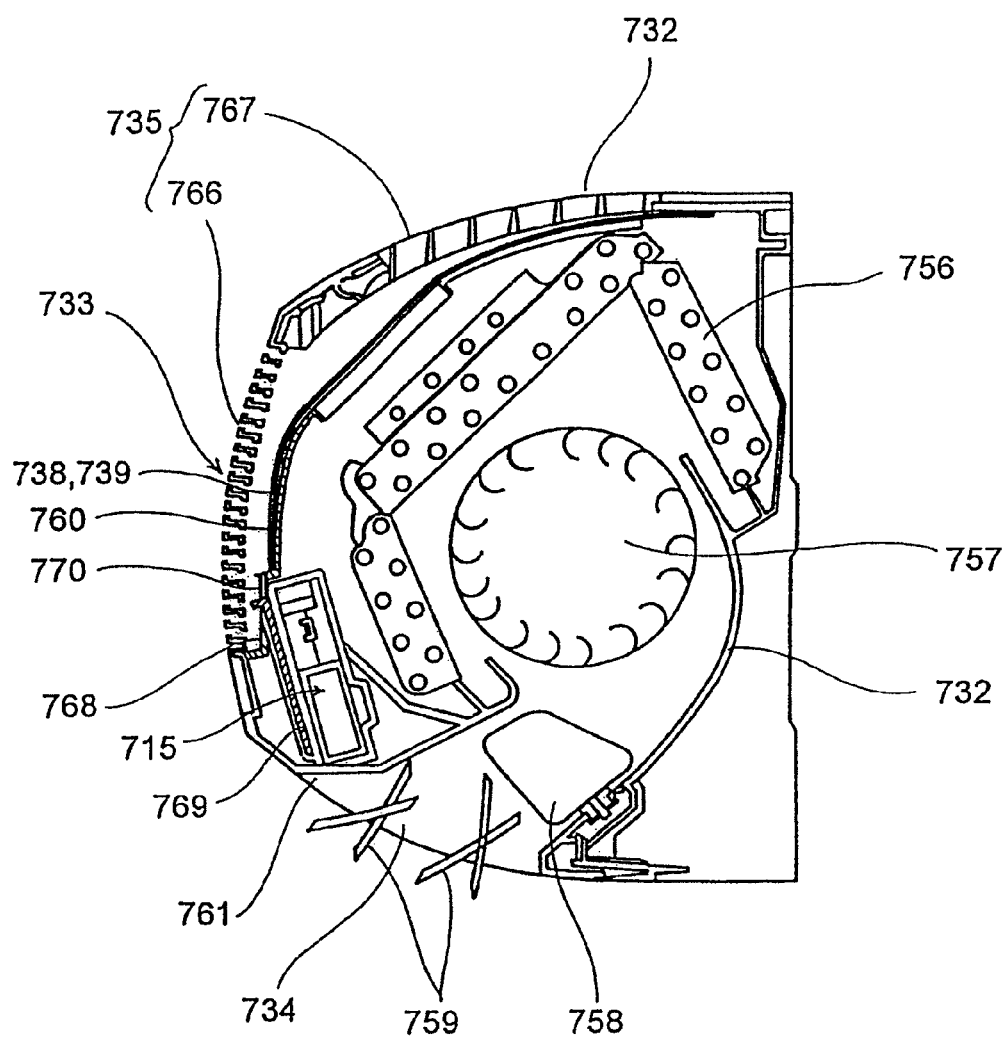
FIG. 57 is a side sectional view of the indoor unit of the air conditioner.
Figure 58:
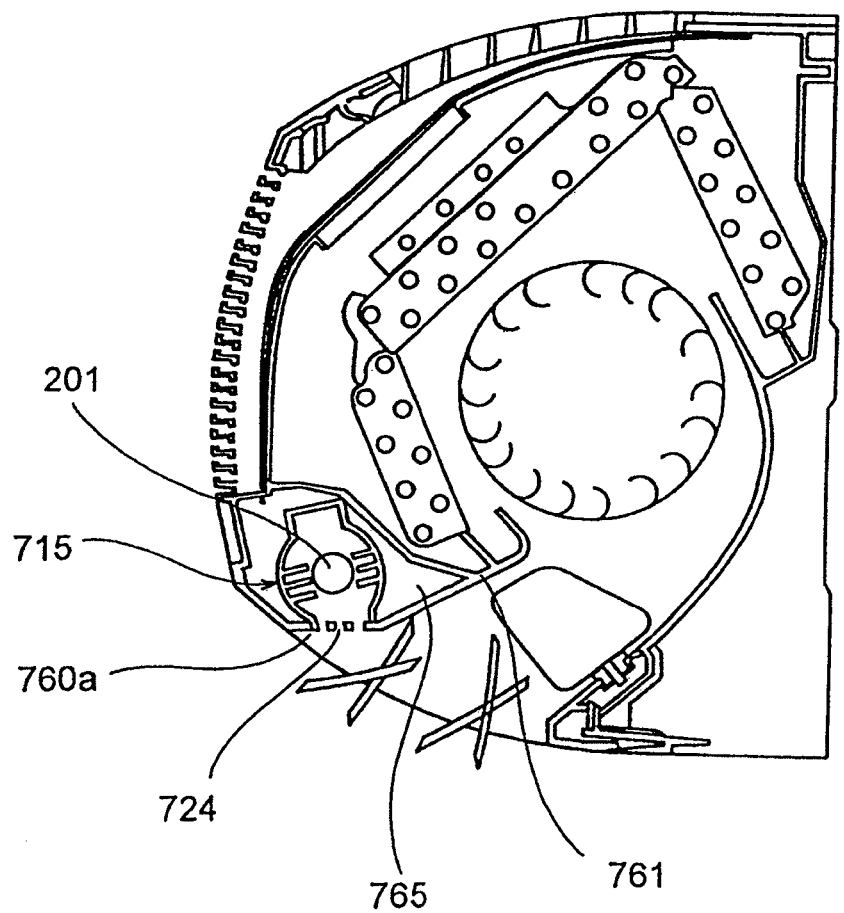
FIG. 58 is a side sectional view of the indoor unit as taken where the ion generating electrode member is located.
Figure 59:
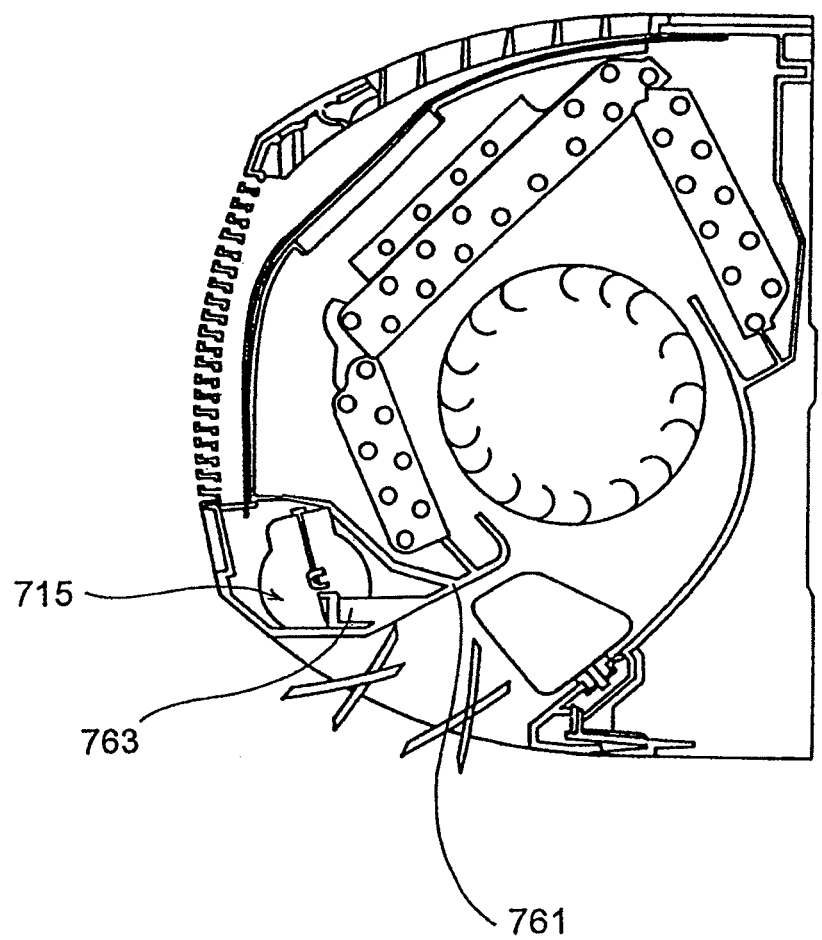
FIG. 59 is a side sectional view of the indoor unit as taken on the left side of where the ion generating device unit is located.
Figure 60:
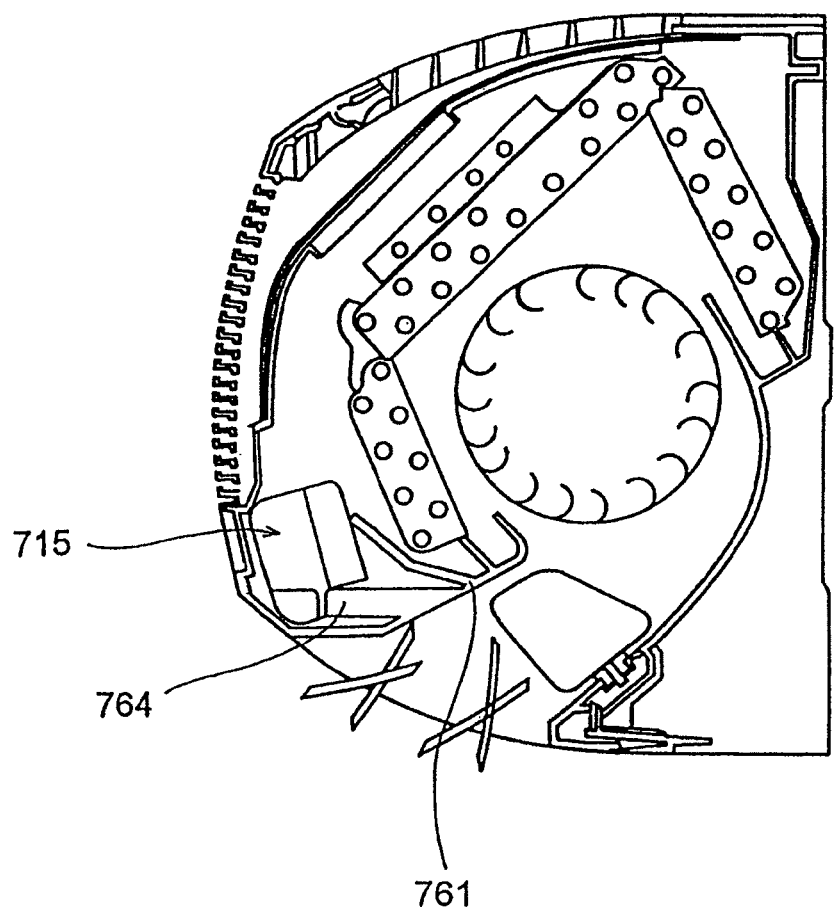
FIG. 60 is a side sectional view of the indoor unit as taken on the right side of where the ion generating device unit is located.
Figure 61:
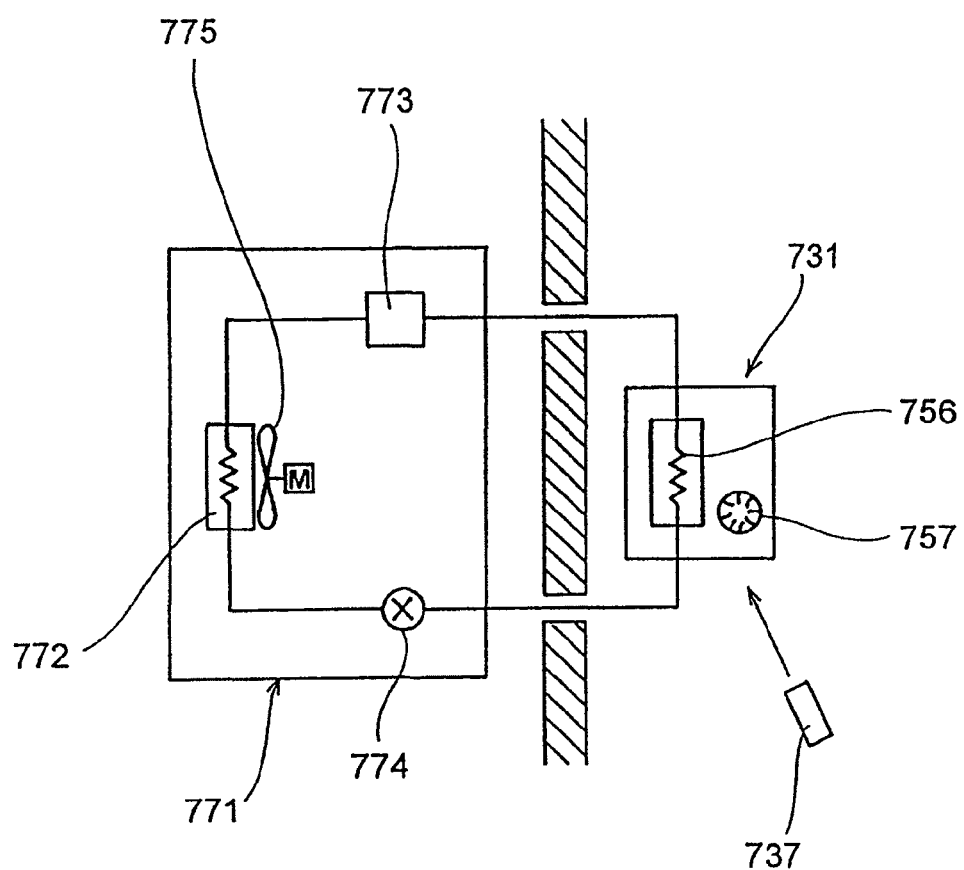
FIG. 61 is a diagram showing an outline of the overall configuration of the air conditioner.

Now, a fifteenth embodiment of the invention will be described with reference to the drawings. FIG. 53 is a front perspective view showing an outline of the structure of the air conditioner, incorporating an ion generating device unit 715, of a fifteenth embodiment of the invention. FIG. 54 is a front perspective view of the air conditioner with its front panel 733 opened. FIG. 55 is an enlarged front view of the on-the-body display panel of the air conditioner. FIG. 56 is a perspective view of the remote control unit of the air conditioner. FIG. 57 is a side sectional view of the indoor unit 731 of the air conditioner. FIG. 58 is a side sectional view of the indoor unit 731 as taken where the ion generating electrode member 202 is located. FIG. 59 is a side sectional view of the indoor unit 731 as taken on the left side of where the ion generating device unit 715 is located. FIG. 60 is a side sectional view of the indoor unit 731 as taken on the right side of where the ion generating device unit 715 is located. FIG. 61 is a diagram showing an outline of the overall configuration of the air conditioner.

As shown in FIG. 53, the indoor unit 731 of the air conditioner is composed of a body casing 732 that houses a heat exchanger, an indoor fan, and other components, a front panel 733 freely openable so as to permit the user to visually check the inside of the body for dirt on the filters, an outlet 734 through which cool or warm air is blown out, an inlet 735 through which indoor air is sucked in, and a on-the-body display panel 736 for indicating the operation status. Moreover, a remote control unit 737 permits remote control of the starting and stopping of operation and the setting of operation conditions.

As shown in FIG. 54, which shows the indoor unit 731 with the front panel 733 opened, over the grid-like inlet formed in the body casing 732, a right-hand filter 738 and a left-hand filter 739 are arranged so as to face the inlet 735 of the front panel 733. In substantially central portions of the right-hand and left-hand filters 738 and 739, air purifying filters 740 and 741, respectively, are fitted.

As shown in FIG. 55, the on-the-body display panel 736, which is provided above the outlet of the indoor unit 731, is composed of an operation lamp 742 for indicating that the air conditioner is operating, a two-digit temperature lamp 743 for indicating the indoor and outdoor temperatures, an air purification lamp 744 for indicating that the ion generating device is operating, a sensor 745 for receiving signals from the remote control unit 737, a timer lamp 746 that is lit when a timer-controlled operation is reserved, and other components.

The remote control unit 737 shown in FIG. 56 is composed of a remote-control display 747 for indicating the operation status, a transmission indicator 748 that is lit when signals are transmitted to the indoor unit, an "auto" button 749 for making the air conditioner operate in an automatic mode, a "heat" button 750 for making it operate in a heating mode, a "cool" button 751 for making it operate in a cooling mode, a "dehumidify" button 752 for making it operate in a dehumidifying mode, a temperature button 753 for setting the indoor temperature, a "purify air" button 754 for starting and stopping the operation of the ion generating device, a "stop" button 755 for stopping the operation of the air conditioner, and other components.

As shown in FIG. 57, which is a side sectional view of the indoor unit 731, the indoor unit 731 is composed of a body casing 732 that serves as the base of the indoor unit 731, an indoor heat exchanger 756, having a heating/cooling medium circulated therethrough, for exchanging heat between indoor air and the heating/cooling medium, an indoor fan 757 for blowing out of the indoor unit 731 the air sucked in and then subjected to heat exchange, a vertical louver 758 for horizontally varying the direction of the air blown out through the outlet 734, a horizontal louver 759 for vertically varying the direction of the air, and the right-hand and left-hand filters 738 and 739 for removing dust and other foreign particles from the air sucked in through the inlet 767.

With the front panel 733 open, the filters 738 and 739 are inserted into position by being guided along filter guides 760 formed in the body casing 732. The left-hand filter 739 is so shaped as not to cover the area where a sub filter 769 is detached from and attached to the inlet 768 of the sub blower unit 716 of the ion generating device unit 715.

Below the indoor heat exchanger 756, a drain pan 761 is provided for collecting the water drained as indoor air is subjected to heat exchange. From the bottom surface of the drain pan 761 frontward, an upper wall constituting an indoor circulation passage is formed, and this upper wall has an opening 760a formed therein that directly connects to the ion outlet 724 of the ion generating device unit 715 (FIG. 58). In a front portion of the drain pan 761, at the left-hand and right-hand ends thereof, bosses 763 and 764 are formed for fitting the ion generating device unit 715 (see FIGS. 59 and 60).

Between the drain pan 761 and the ion generating device unit 715, a styrene foam member 756 is fitted to prevent condensation on the outside of the drain pan 761 under the influence of the water collected in the drain pan 761 and to prevent condensed water from entering the ion generating device unit 715 (see FIG. 58).

The inlet 735 consists of an inlet 766 for sucking in indoor air from the front, i.e. through the front panel 733, and an inlet 767 for sucking in indoor air through the top face of the body casing 732.

In the outlet 734 of the body casing 732 is formed the horizontal louver 759 for vertically varying the direction of the flow of the air that has passed through the indoor heat exchanger 756 and then the fan, and on the upstream side of the horizontal louver 759 is formed the vertical louver 758 for horizontally varying the direction of the flow of air. Substantially above the horizontal louver 759 is formed the ion outlet 724 of the ion generating device unit 715.

The air flow inside the ion generating device unit 715 is as follows. As shown in FIG. 57, the sub blower unit 716 sucks in air through the ion inlet 768 of the front panel 733 and then through the detachable sub filter 769 provided between the body casing 732 and the sub blower unit 716 of the ion generating device unit 715. The air is then passed through the ion generating device unit 715 and is then discharged through the ion outlet 724 together with the negative and positive ions generated therein by the ion generating electrode member 202. The air containing negative and positive ions thus discharged through the ion outlet 724 is discharged into the room together with the air that has passed through the indoor air circulation passage, i.e. the air sucked in through the inlet 735 by the indoor fan 757, then passed through the indoor heat exchanger 756 so as to be subjected to heat exchange, and then delivered to the outlet 734. In this way, the air containing the negative and positive ions generated by the ion generating electrode member 202 is discharged through the outlet 734 of the indoor unit 731, and thus the air passage between the ion generating electrode member 202 and the outlet 734 of the indoor unit 731 is short. This helps reduce the loss in the amount of negative and positive ions in the air, and thereby enhances the effect of sterilization in the room.

The sub filter 769 is detachably attached in the vicinity of the inlet of the sub blower unit 716 of the ion generating device unit 715, and therefore, with the front panel 733 opened upward, can easily be detached through a sub filter slot 770 and cleared of dust and other foreign particles. This helps minimize the settlement of dust and other foreign particles on the ion generating device unit 715, and thereby achieve stable generation of negative and positive ions. Moreover, providing the sub filter 769 separately from the filters 738 and 739 of the indoor unit 731 enhances usability and facilitates maintenance.

The ion generating device unit 715 is fitted to the indoor unit 731 by being fixed thereto with screws with the bosses 763 and 764 that are formed at both ends of the drain pan 761 fitted into the fitting holes 720b and 721b of the unit body 718 as shown in FIGS. 59 and 57. In this way, the ion generating device unit 715 is placed at the lower end of the indoor heat exchanger 756, substantially parallel thereto. This makes efficient use of the space inside the indoor unit 731 possible, and thus helps make the indoor unit 731 compact enough not to require an unduly large space for its installation.

As shown in FIG. 61, the entire system of this embodiment, when seen in an outline of its configuration, is composed of the indoor unit 731, an outdoor unit 771, and the remote control unit 737. The indoor unit 731 is composed of the indoor heat exchanger 756 and the indoor fan 757. The outdoor unit 771 is composed of an outdoor heat exchanger 772, a compressor 773, an expansion valve 774, and an outdoor fan 775.

Now, how the air conditioner configured as described above operates will be described. First, the operation procedure will be described. When the "auto" button 749 on the control panel of the remote control unit 737 is pressed, the air conditioner starts operating. At this point, the "operation" lamp 742 on the on-the-body display panel 736 of the indoor unit 731 is lit, the indoor temperature is indicated digitally by the temperature lamp 743, and the operation mode (here, automatic), wind volume, wind direction, and other pieces of information are indicated on the display 747 of the control panel of the remote control unit 737.

On the other hand, when the "heat" button 750 on the control panel of the remote control unit 737 is pressed, the "operation" lamp 742 on the on-the-body display panel 736 of the indoor unit 731 is lit, the indoor temperature is indicated digitally by the temperature lamp 743, and the operation mode (here, heating), wind volume, wind direction, temperature, and other pieces of information are indicated on the display 747 of the control panel of the remote control unit 737.

To stop the operation, the "stop" button 755 on the control panel of the remote control unit 737 is pressed. As a result, the operation lamp 742 on the on-the-body display panel 736 of the indoor unit 717 goes out, and the air conditioner stops operating.

To change the temperature, for example to raise the temperature by 1° C., the "Δ" switch of the temperature button 753 is pressed once. This changes the target temperature by 1° C., and, in the heating and cooling mode, the target temperature is indicated on the remote-control display 747 on the control panel of the remote control unit 737 and on the on-the-body display panel 736 of the indoor unit 731.

In the automatic or dehumidifying mode, the value by which the temperature is to be raised is indicated on the remote-control display 747 of the control panel of the remote control unit 737, and the target temperature is indicated on the on-the-body display panel 736 of the indoor unit 731.

Now, an example of how the air conditioner operates will be described. When the air conditioner operates in the cooling mode, the heat-exchange medium condensed and thereby brought into a high-temperature state by the compressor 773 of the outdoor unit 771 is passed to the outdoor heat exchanger 772 of the outdoor unit 771. In the outdoor heat exchanger 772, the outdoor fan 775 takes way heat from the heat-exchange medium and thereby cools it. The heat-exchange medium is then passed through the expansion valve to the indoor heat exchanger 756, where the heat-exchange medium evaporates. As a result, indoor air, which is passed through the indoor heat exchanger 756 by the indoor fan 757, is cooled. When the air conditioner operates in the heating mode, the heat-exchange medium is circulated in the opposite direction to the direction in which it is circulated in the cooling mode. Specifically, the condensed heat-exchange medium is passed to the indoor heat exchanger 756 of the indoor unit 731, and indoor air is passed through the indoor heat exchanger 756 and is thereby heated. In this way, the room is heated.

When the ion generating device unit 715 is started, by pressing the "purify air" button 754 on the control panel of the remote control unit 737, while the air conditioner is operating in any of the automatic, cooling, heating, dehumidifying, and other modes, then, when the air conditioner is started next time, air purification is started simultaneously. When the "purify air" button 754 is pressed, a high alternating-current voltage is applied to the driver circuit unit 717 of the ion generating device unit 715, so that $H^+(H_2O)_m$ and $O_2^-(H_2O)_n$ are generated as negative and positive ions, respectively.

The indoor air sucked in through the ion inlet 768 by the sub blower unit 716 is passed through the sub filter 769, which removes dust and other foreign particles from the air, and is then passed to the ion generating electrode member 202, which generates negative and positive ions in the air. The air, now containing negative and positive ions, then flows out through the ion outlet 724, and is then blown out, together with the air that has passed through the indoor circulation passage, through the outlet 734 so as to be circulated throughout the room by convection.

To start the ion generating device unit 715 independently when the air conditioner is not in operation, the "purify air" button 754 on the remote control unit 737 is pressed. As a result, a high alternating-current voltage starts being applied to the ion generating device unit 715, and also to the motors that drive the indoor fan 756 and the horizontal louver 759 of the indoor unit 731.

The indoor air sucked in through the ion inlet 768 of the front panel 733 is passed through the sub filter 769, which removes dust and other foreign particles from the air, and is then passed to the ion generating electrode member 202, which generates negative and positive ions in the air. The air, now containing negative and positive ions, then flows out of the unit body through the ion outlet 724, and is then blown out, together with the air that has passed through the indoor circulation passage, through the outlet 734 into the room. In this way, indoor air is not only conditioned, but also sterilized, with airborne germs killed and removed therefrom by the action of positive and negative ions.

In this embodiment, an air conditioner is taken up as an example of an air conditioning apparatus that incorporates an ion generating device unit. However, the ion generating device unit maybe incorporated in an air conditioning apparatus of any kind, for example, an air purifier, dehumidifier, humidifier, refrigerator, kerosene fan heater, kerosene stove, electric stove, etc. In any case, it is possible to achieve sterilization by the action of negative and positive ions.

Figure 62:
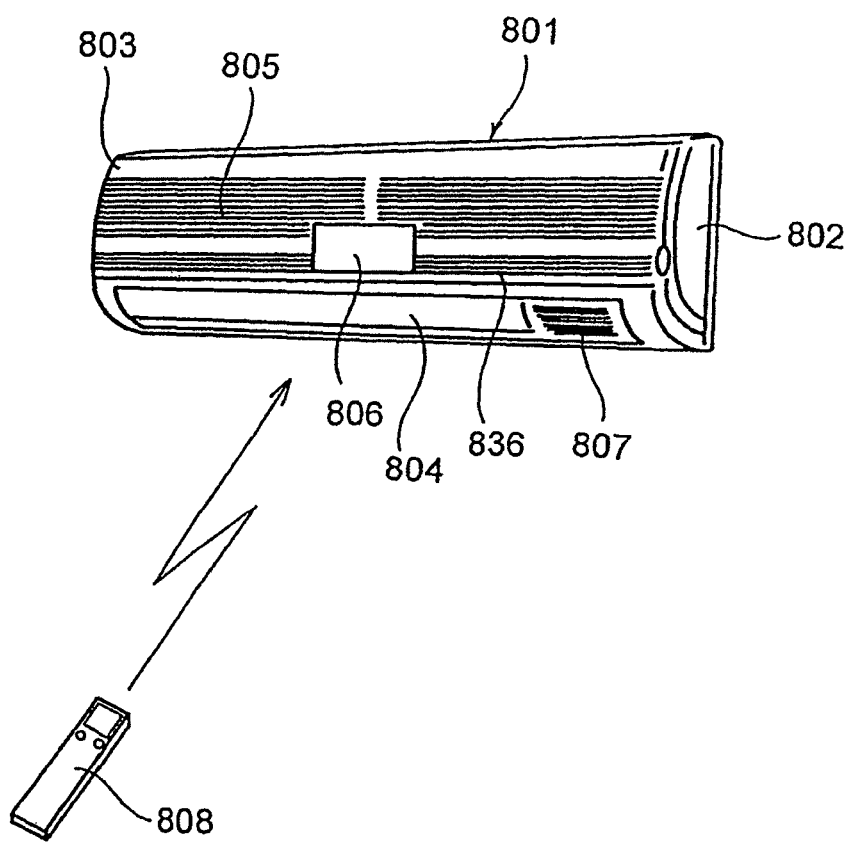
FIG. 62 is a perspective view of the indoor unit of the air conditioner, incorporating an ion generating device unit, of a sixteenth embodiment of the invention.
Figure 63:
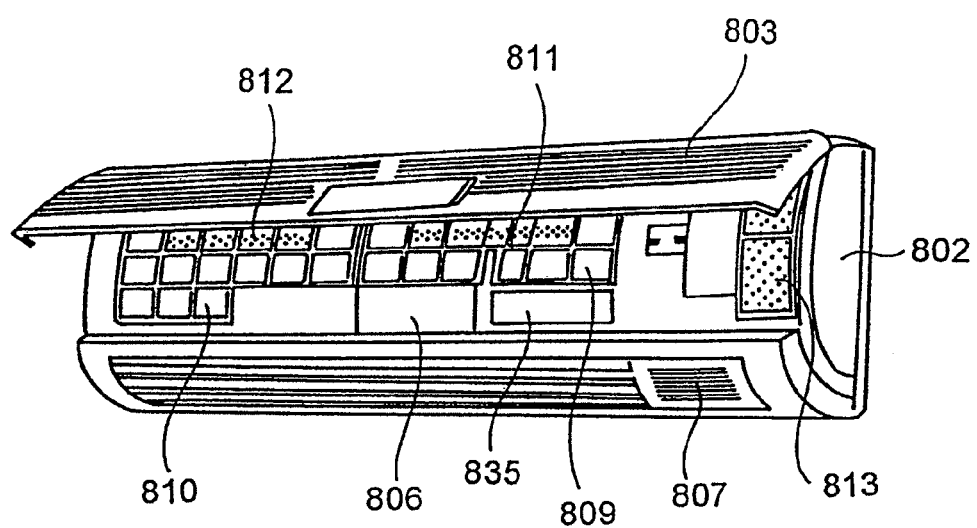
FIG. 63 is a perspective view of the indoor unit, with its front panel opened.
Figure 64:
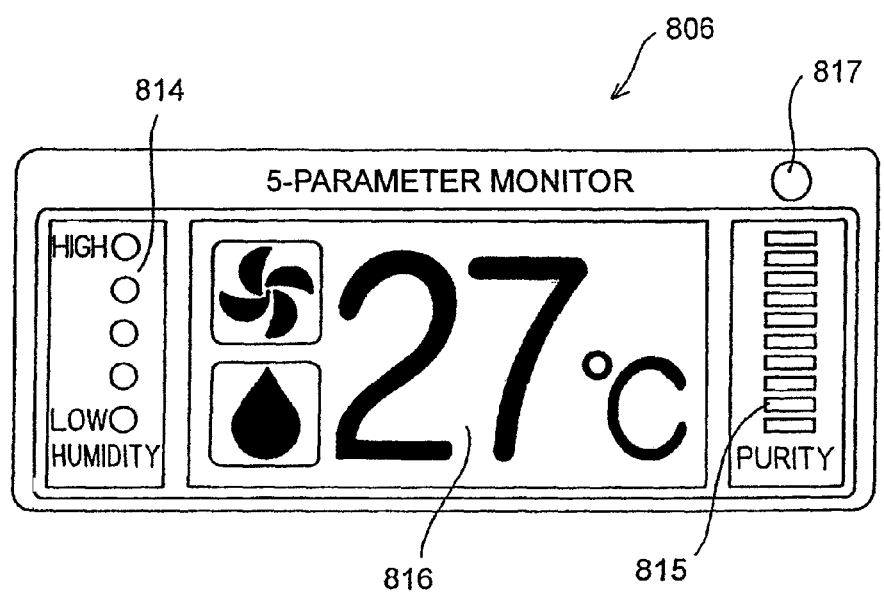
FIG. 64 is an enlarged front view of the liquid crystal display device of the air conditioner.
Figure 65:
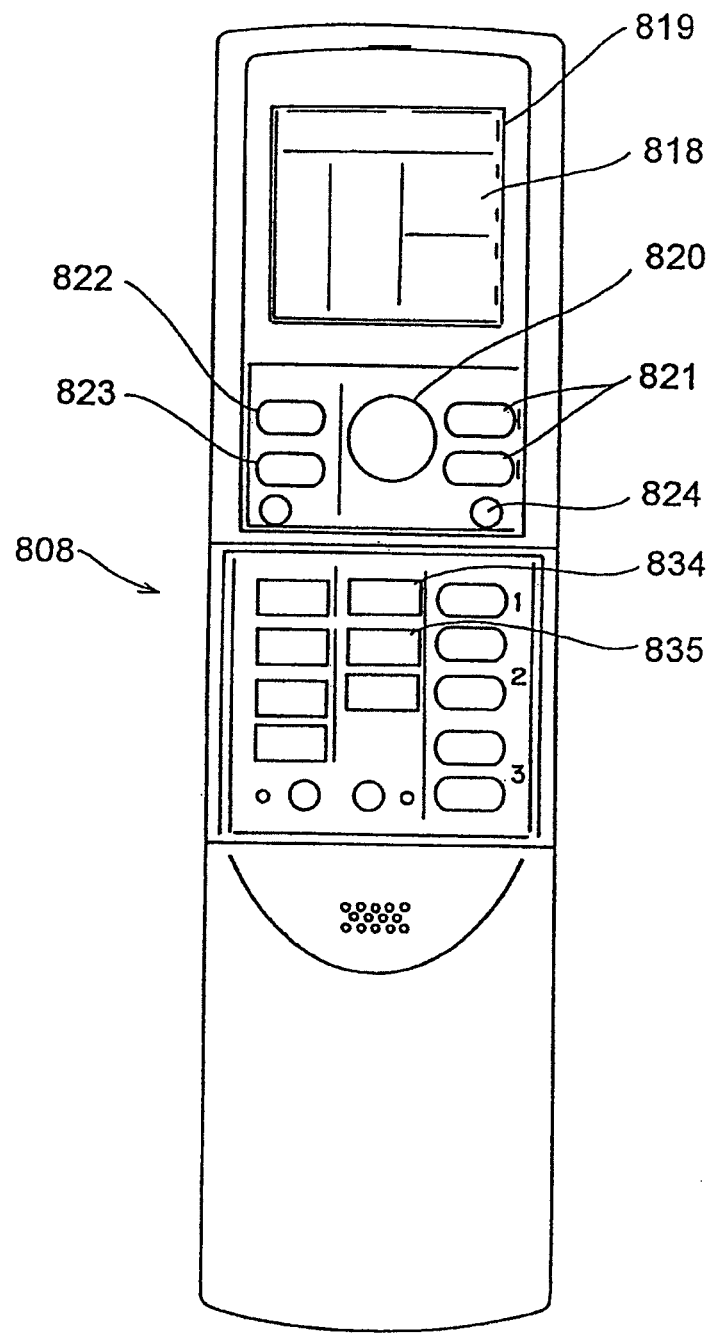
FIG. 65 is an enlarged view of the remote control unit of the air conditioner.
Figure 66:
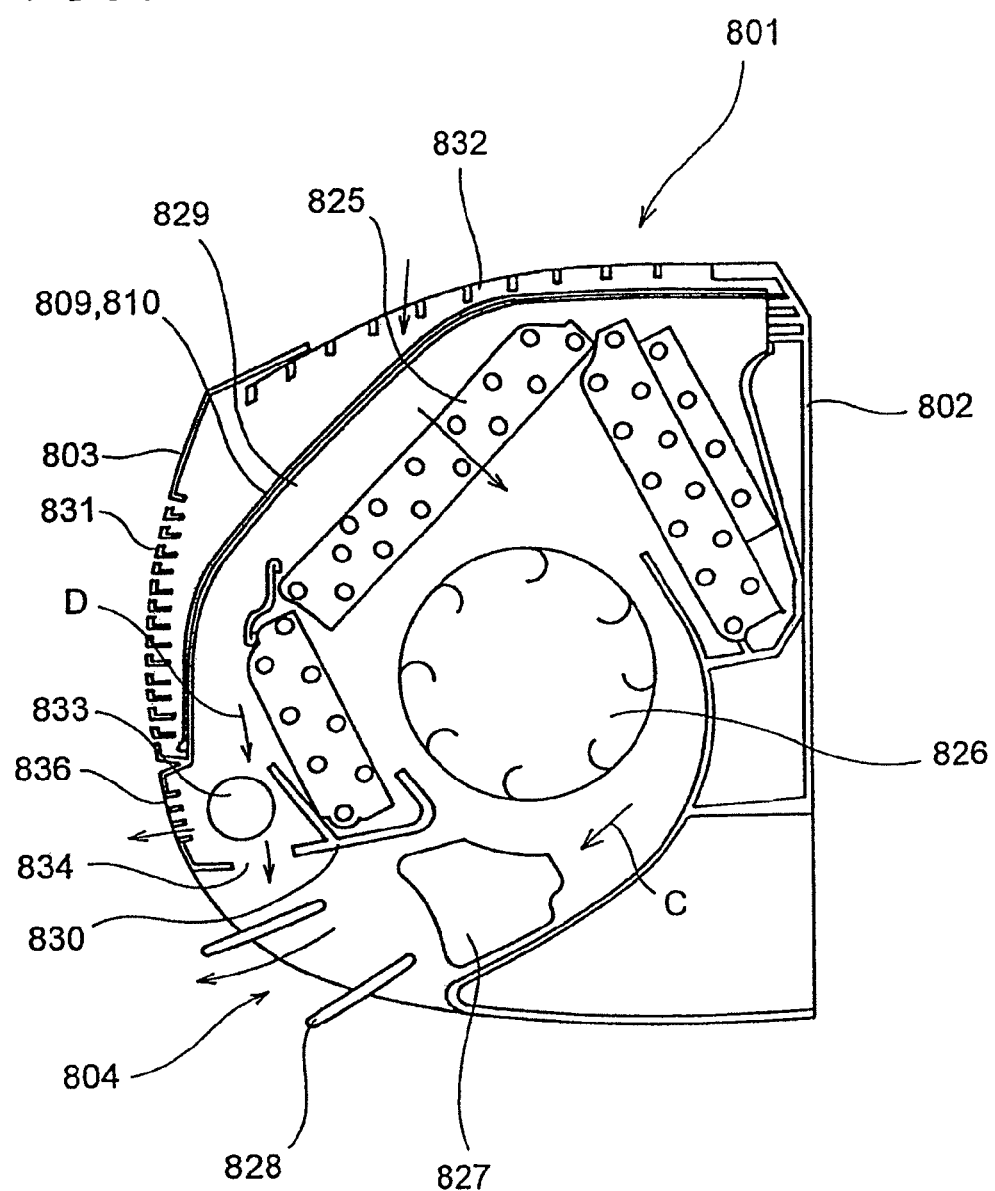
FIG. 66 is a side sectional view of the indoor unit of the air conditioner.
Figure 67:
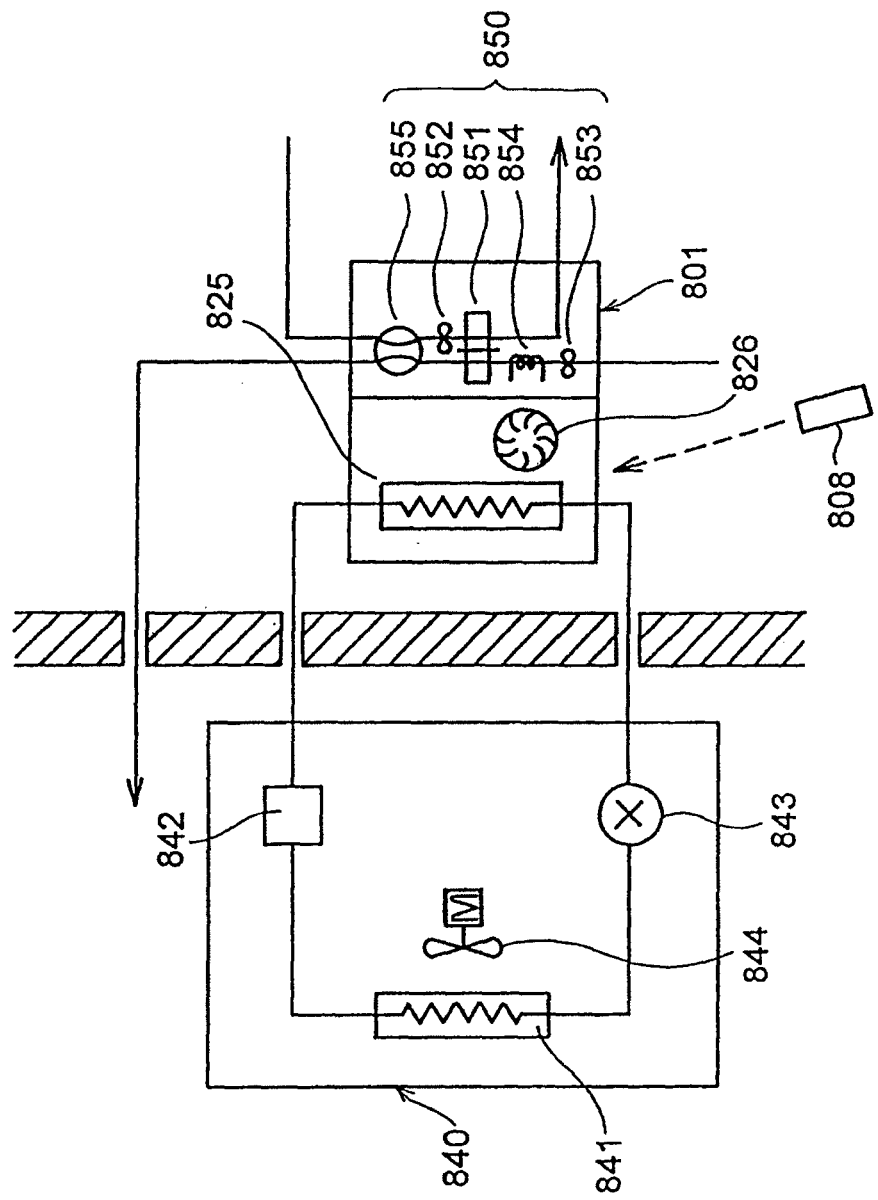
FIG. 67 is a diagram showing an outline of the overall configuration of the air conditioner.
Figure 68:
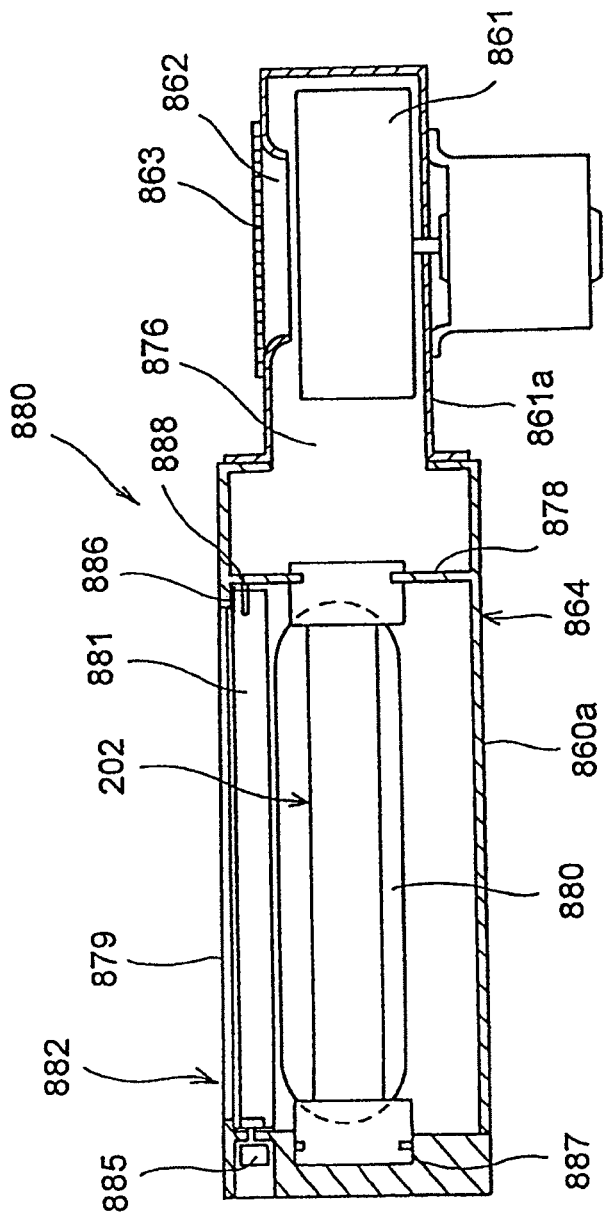
FIG. 68 is a sectional view of the ion generating device unit incorporated in the air conditioner.
Figure 69A:
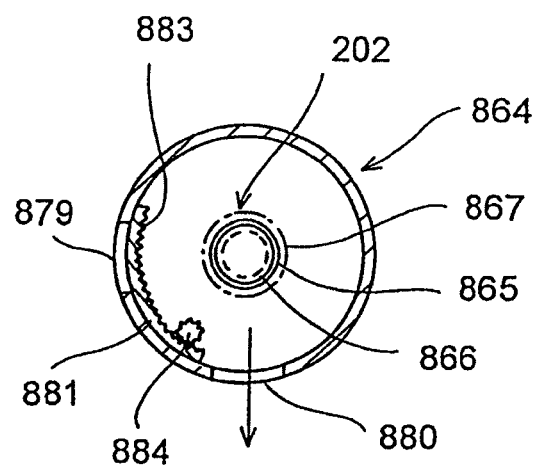
FIG. 69A is a sectional view of the ion generating device unit, with its first outlet closed and its second outlet opened.
Figure 69B:
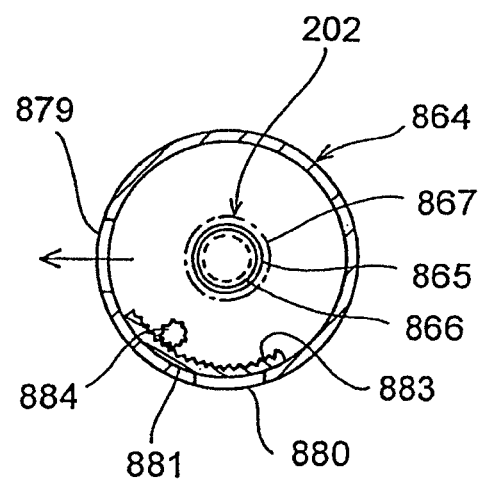
FIG. 69B is a sectional view of the ion generating device unit, with its first outlet opened and its second outlet closed.
Figure 70:
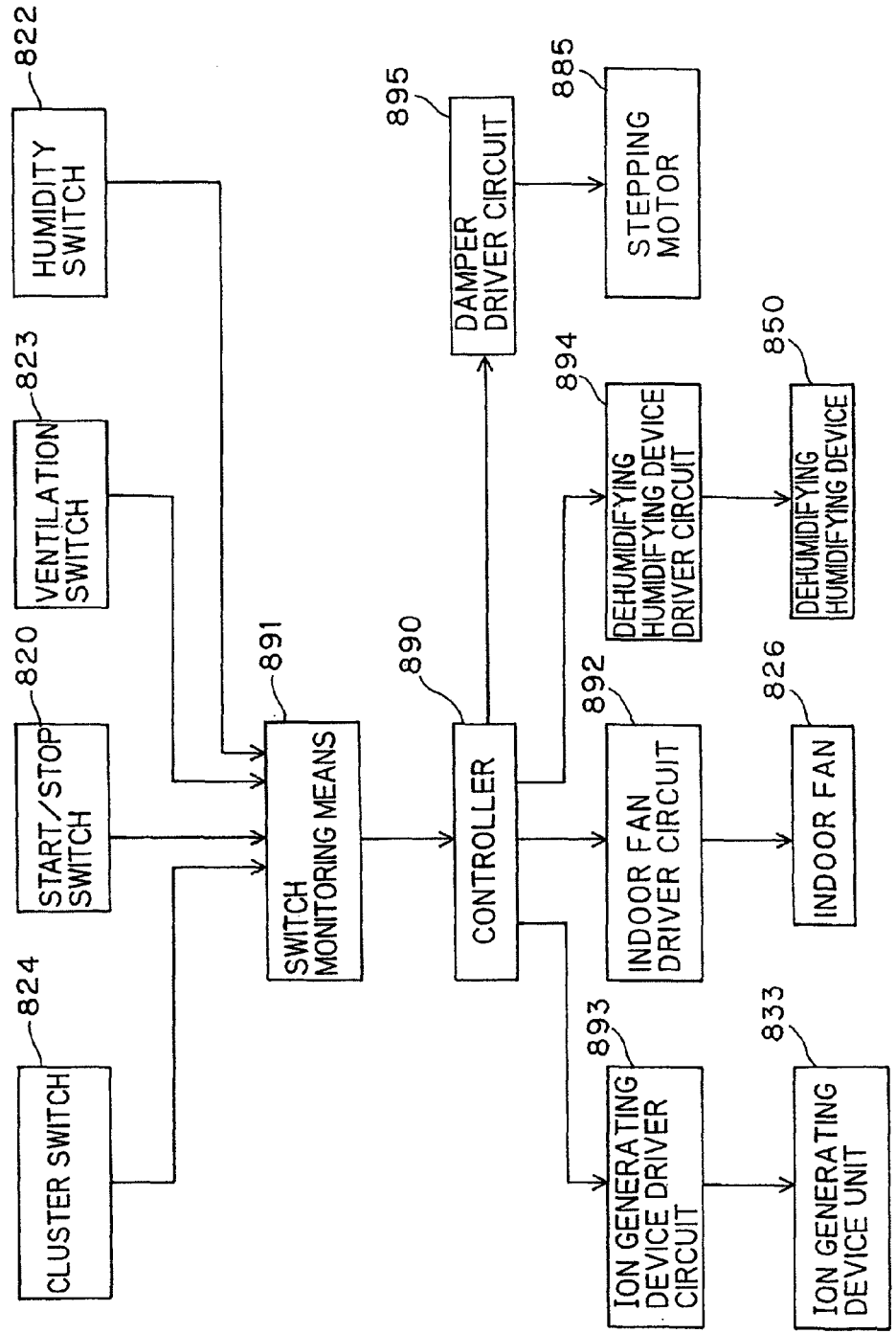
FIG. 70 is a block diagram of the controller of the air conditioner.
Figure 71:
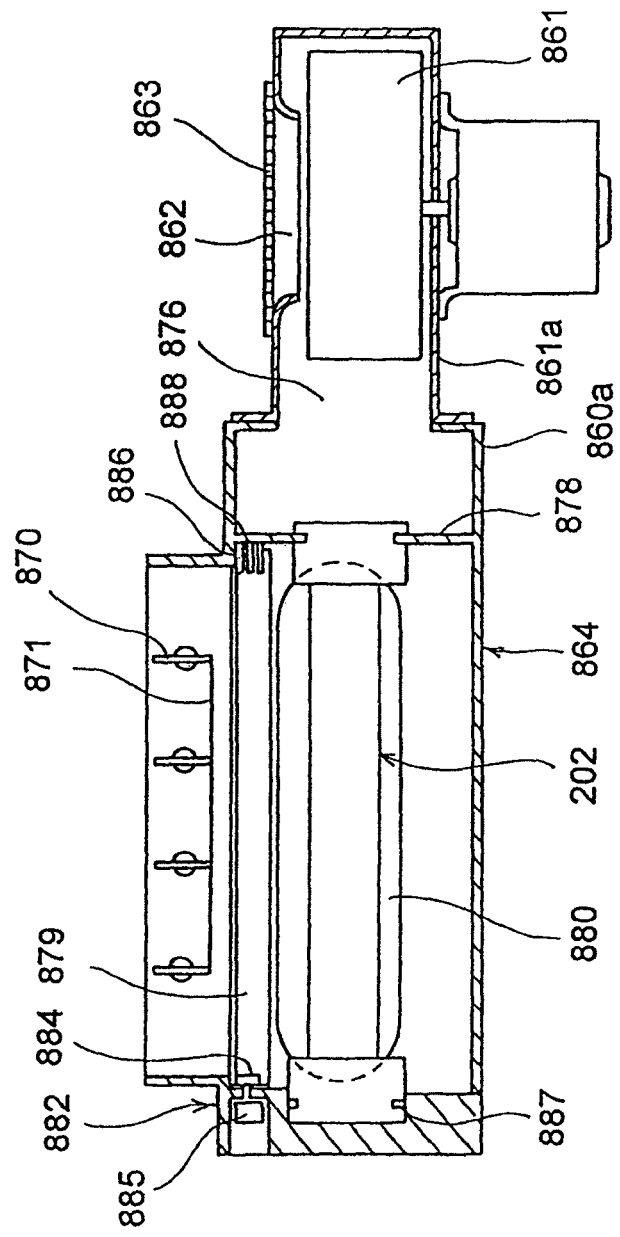
FIG. 71 is a sectional view of another example of the ion generating device unit.
Figure 72:
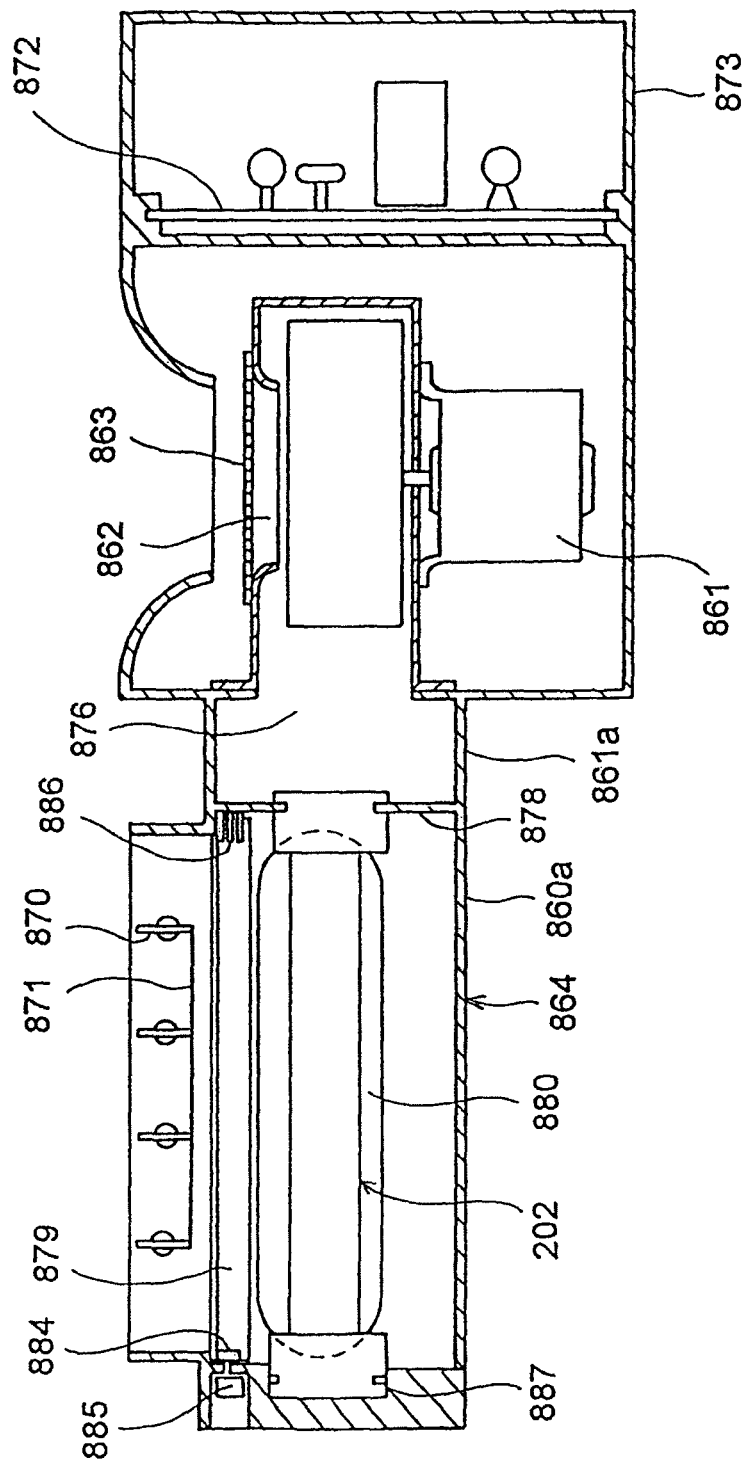
FIG. 72 is a sectional view of yet another example of the ion generating device unit.
Figure 73:
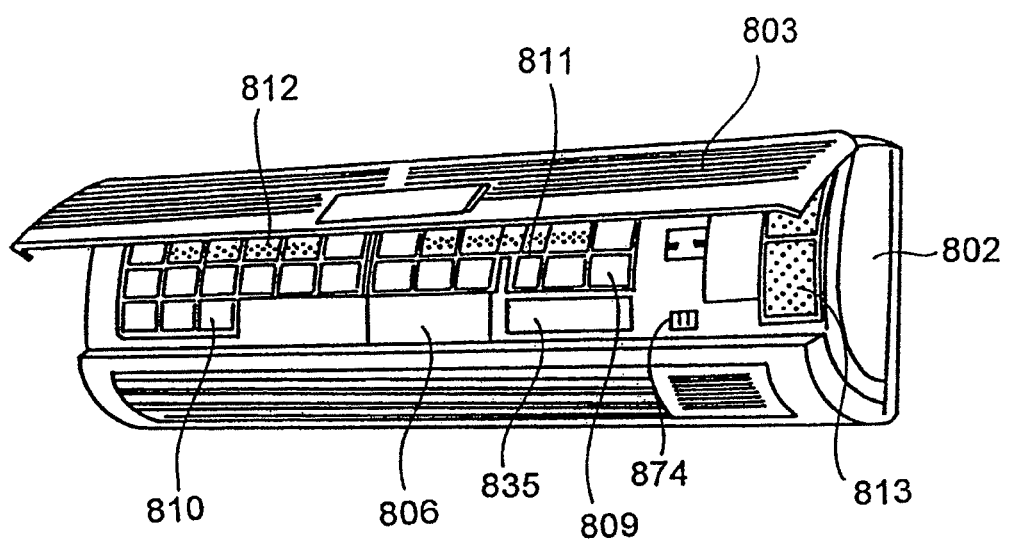
FIG. 73 is a perspective view of the indoor unit of an air conditioner provided with a connector for connection with the ion generating device unit, with its front panel opened.

Now, a sixteenth embodiment of the invention will be described with reference to the drawings. FIG. 62 is a perspective view of the indoor unit 801 of the air conditioner, incorporating an ion generating device unit 833, of a sixteenth embodiment of the invention. FIG. 63 is a perspective view of the indoor unit 801, with its front panel 803 opened. FIG. 64 is an enlarged front view of the liquid crystal display panel 806 of the air conditioner. FIG. 65 is an enlarged view of the remote control unit 808 of the air conditioner. FIG. 66 is a side sectional view of the indoor unit 801 of the air conditioner. FIG. 67 is a diagram showing an outline of the overall configuration of the air conditioner. FIG. 68 is a sectional view of the ion generating device unit 833 incorporated in the air conditioner. FIG. 69A is a sectional view of the ion generating device unit 833, with its first outlet 879 closed and its second outlet 880 opened. FIG. 69B is a sectional view of the ion generating device unit 833, with its first outlet 879 opened and its second outlet 880 closed. FIG. 70 is a block diagram of the control system of the air conditioner. FIG. 71 is a sectional view of another example of the ion generating device unit 833. FIG. 72 is a sectional view of yet another example of the ion generating device unit 833. FIG. 73 is a perspective view of the indoor unit 801 of an air conditioner provided with a connector for connection with the ion generating device unit 833, with its front panel 803 opened.

As shown in FIG. 62, the indoor unit 801 is provided with a body casing 802 that houses a heat exchanger, an indoor fan, and other components, a front panel 803 openable so as to permit the user to visually check the inside of the body for dirt on the filters and the like, an outlet 804 through which cool or warm air is blown out, an inlet 805 through which indoor air is sucked in, a liquid crystal display panel 806 for indicating the operation status, and a dehumidifying/humidifying outlet 807 through which the air dehumidified or humidified by a dehumidifying/humidifying device is blown out. Moreover, a remote control unit 808 permits remote control of the starting and stopping of operation and the setting of operation conditions.

As shown in FIG. 63, the front panel 803 is openably supported on the body casing 802. In the body casing 802, a grid-like outlet 804 is formed so as to face the inlet 805 formed in the front panel 803. In this inlet 805, a right-hand filter 809 and a left-hand filter 810 for removing dust and other foreign particles from the air sucked in through the inlet 805 are arranged. In substantially central portions of the right-hand and left-hand filters 809 and 810, air purifying filters 811 and 812, respectively, are fitted. In a right-hand portion of the body casing 802, a dehumidifying/humidifying inlet for sucking in indoor air for the dehumidifying/humidifying device is formed, and, in this inlet, a dehumidifying/humidifying filter 813 is fitted.

In a central portion of the body casing 802, a liquid crystal display panel 806 as shown in FIG. 64 is provided. This liquid crystal display panel 806 is composed of a humidity lamp 814 that is lit according to the indoor humidity, an air purity lamp 815 that changes its color according to how contaminated indoor air is, a display 816 for indicating the indoor atmosphere condition and the operation status according to the signals transmitted as the operation buttons on the remote control unit 808 are pressed, and a sensor 817 for receiving signals from the remote control unit 808.

As shown in FIG. 65, the remote control unit 808 is composed of a remote-control display 818 for indicating the operation status, a transmission indicator 801 that is lit when signals are transmitted to the indoor unit 801, a start/stop switch 820 for starting and stopping the operation of the air conditioner, a temperature switch 821 for setting the indoor temperature, a humidity switch 822 for starting and stopping the dehumidifying operation of the dehumidifying/humidifying device, a ventilation switch 823 for starting and stopping the ventilating operation of the dehumidifying/humidifying device, a cluster switch 824 for starting and stopping the operation of the ion generating device unit 833, and other components.

As shown in FIG. 66, inside the indoor unit 801 are housed an indoor heat exchanger 825 that exchanges heat between the heating/cooling medium passed inside it and the indoor air passed outside it, and an indoor fan 826 for blowing out the indoor air sucked in and then subjected to heat exchange by the indoor heat exchanger 825.

In the outlet 804 formed in a lower portion of the front face of the body casing 802, a vertical louver 827 for horizontally varying the direction the flow of the air and a horizontal louver 828 for vertically varying the direction of the flow are rotatably fitted.

In the front face of the body casing 802, filter guides 829 are formed so that, with the front panel 803 opened, the filters 809 and 810 are inserted into position by being guided along those filter guides 829. The right-hand filter 809 is so shaped as not to cover the liquid crystal display panel 806. Below the heat exchanger 825, a drain pan 830 is provided for collecting the water drained as indoor air is subjected to heat exchange. The inlet 805 consists of a front inlet 831 formed so as to surround the liquid crystal display panel 806 provided on the front panel 803 and an upper inlet 832 formed in the top surface of the body casing 802.

A circulation passage C is formed that leads from the inlet 805 to the filters 809 and 810, then to the heat exchanger 825, and then to the outlet 804. The indoor air sucked in through the inlet 805 and then passed through the circulation passage C is then blown out into the room. In this way, indoor air is circulated.

In the vicinity of the outlet 804 of the body casing 802, an ion generating device unit 833 is placed. Through this ion generating device unit 833, an air flow passage D is formed separately from the circulation passage C. The air flow passage D is formed between the heat exchanger 825 and the filters 809 and 810, and communicates with the circulation passage C. Thus, the air that has entered the air flow passage D passes directly through the ion generating device unit 833, i.e. without passing through the inlet 805, then flows, through a confluence 834 located on the downstream side of the heat exchanger 825, into the circulation passage C, and is then blown out into the room together with the air that has been passing through the circulation passage C. In the body casing 802, an ion discharge opening 835 is formed so as to face the ion generating device unit 833, and, in the front panel 803, an ion outlet 836 is formed so as to communicate with that opening 835. By placing the ion generating device unit 833 in the air flow passage D in this way, it is possible to prevent the lowering of its ion generating performance resulting from condensation.

As shown in FIG. 67, the air conditioner is composed of the indoor unit 801, an outdoor unit 840, and the remote control unit 808. The indoor unit 801 is provided with the heat exchanger 825 and the indoor fan 826. The outdoor unit 840 is provided with an outdoor heat exchanger 841, a compressor 842, an expansion valve 843, and an outdoor fan 844.

The indoor unit 801 incorporates a dehumidifying/humidifying device 850. The dehumidifying/humidifying device 850 is composed of a moisture absorbing rotor 851 that absorbs the moisture contained in indoor air and separates it, a dehumidifying fan 852 that sucks in indoor air, a regeneration fan 853 that passes regenerated air to the moisture absorbing rotor 851, a regeneration heater 854 that heats the regenerated air that is passed to the moisture absorbing rotor 851, and a damper 855 that switches passages.

As shown in FIG. 68, the ion generating device unit 833 is composed of the ion generating electrode member 202 of the ion generating device 201 (see FIG. 8) of the seventh embodiment described earlier, a blower 861, a unit inlet 862, a filter 863, a unit case 864, and a plurality of outlets.

The unit case 864 is formed by fitting integrally together a 860a for housing the ion generating electrode member 202 and a casing 861a for the blower 861. The unit case 864 has the shape of an elongate cylinder or rectangular prism, and is made of a material that excels in resistance to ozone, for example polybutylene terephthalate (PBT). The unit case 864 may be given any other shape than specifically described here. The blower 861 is placed on the upstream side of the ion generating electrode member 202 in the direction of its axis so as to communicate, through a fitting opening 876, with the ion generating electrode member 202.

The air taken in through the unit inlet 805 formed in the casing 861a is passed through the fitting opening 876 and then through a ventilation opening 878 to the ion generating electrode member 202 by the blower 861, so that the negative and positive ions generated by the ion generating electrode member 202 are blown out. The shapes of the casing, fan, and motor are determined according to how they are housed in the air flow passage D of the indoor unit 801.

In the unit inlet 805, the filter 863 is fitted. The filter 863 here is a pre-filter for removing dust and other foreign particles, or a deodorizing filter for removing odors in the room, or a combination of both.

In the case 860a of the unit case 864, two outlets 804 are formed so as to face the ion generating electrode member 202, namely a first outlet 879 through which the air is blown out directly into the room through the ion outlet 836 and a second outlet 880 through which the air is blown out toward the confluence 834. The two outlets 879 and 880 are arranged so as to point 90° apart from each other. The unit inlet 862 is arranged so as to point in the same direction as the first outlet 879, or 180° apart from the second outlet 880.

To permit the direction in which the ion generating device unit 833 blows out ions to be switched according to the operation status of the air conditioner, a switching means is provided, which is composed of a damper 881 that opens and closes the outlets 879 and 880 individually and a driving mechanism for driving the damper 881. As shown in FIGS. 69A and 69B, the damper 881 is an arc-shaped plate that fits along the inner surface of the unit case 864, and is so sized as to cover one-third of that surface. The damper 881 is supported at both ends in the direction of its axis so as to be slidable along the inner surface of the unit case 864, and is fitted with, at one end, a gear 884 that meshes with a pinion gear 883 and a stepping motor 885 for rotating the gear 884. When the stepping motor 885 is driven, it moves the damper 881 in such a way that one of the outlets 879 and 880 is opened and the other is closed. In this way, switching between the outlets 879 and 880 is achieved. By designing the damper 881 to be movable up to a position where it leaves both the outlets 879 and 880 open, it is possible to blow out the air through both the outlets 879 and 880 simultaneously.

In the vicinity of the ion generating electrode member 202, a light emitter 886 is provided. The damper 881 is made of a transparent material, and, when the ion generating electrode member 202 is operating, the light emitter 886 illuminates it with, for example, blue light so that the user can visually check the ion generating electrode member 202. The light emitter 886 may be so arranged that its light can be seen directly from outside.

In the ion generating device unit 833 structured as described above, the damper 881 is mounted in a predetermined position inside the unit case 864, then the stepping motor 885 is mounted on and temporarily fixed to the unit case 864 from outside, then the gear 884 is fitted on the shaft of the stepping motor 885 and meshed with the pinion gear 883 of the damper 881, and then the stepping motor 885 is fixed earnestly. Then, a circuit board having the light emitter 886 mounted thereon is fitted in a predetermined position. Then, in a fitting hole 887 inside the unit case 864, an insulating gasket 868 of the ion generating electrode member 202 is fitted, and then the casing 861a of the blower 861 fitted with the filter 863 is fitted in position with screws or the like. This completes the assembly of the ion generating device unit 833. This ion generating device unit 833 is then removably fitted in a predetermined position in the air flow passage D with screws or the like.

Next, an example of how the air conditioner operates will be described. The air conditioner is operated using the remote control unit 808, and therefore the operation procedure using it will be described. Every time the mode selection switch 834 on the control panel of the remote control unit 808 is pressed, the operation mode switches from "automatic" to "heating" to "cooling" to "drying" to "automatic", and so forth, and the selected mode is indicated on the remote-control display 818. Through this operation, the desired operation mode is selected.

The signals transmitted from the remote control unit 808 are received by the sensor 817 of the liquid crystal display panel 806 of the indoor unit 801. The indoor unit 801 incorporates a control system. As shown in FIG. 70, the control system is provided with a controller 890 consisting of a CPU, a memory, and other components, a switch monitoring means 891, an indoor fan driver circuit 892, an ion generating device driver circuit 893, a dehumidifying/humidifying device driver circuit 894, and a damper driver circuit 895. The control system activates the individual circuit blocks thereof according to the signals from the remote control unit 808.

When the start/stop switch 820 is pressed, the operation mode, target temperature, and indoor temperature are indicated one after another on the liquid crystal display panel 806 of the indoor unit 801. During operation, the indoor temperature is kept indicated. To stop the operation, the start/stop switch 820 is pressed. This causes the indication on the liquid crystal display panel 806 to go out and the operation to stop. To change the temperature, for example to raise the temperature by 1° C., the "Δ" switch of the temperature switch 821 is pressed once. This raises the target temperature by 1° C., and, in the heating or cooling mode, the target temperature is indicated on the remote-control display 818 and on the liquid crystal display panel 806. Here, the target temperature is indicated on the liquid crystal display panel 806. On the other hand, in the automatic or drying mode, the value by which the temperature is to be raised is indicated on the remote-control display 818, and the target temperature is indicated on the liquid crystal display panel 806. Here, the indication of the target temperature on the liquid crystal display panel 806 switches back to the indication of the indoor temperature after about four seconds. To change the wind volume, every time a wind volume switch 835 is pressed, the wind volume is changed so that the indication on the remote-control display 818 changes from "wind volume auto" to "wind volume Δ" to "wind volume ΔΔ" to "wind volume ΔΔΔ" to "wind volume auto", and so forth, and the indication on the liquid crystal display panel 806 changes from "wind volume auto" to "gentle wind" to "moderate wind" to "strong wind", to "wind volume auto", and so forth.

In this way, the desired operation mode is selected. In the cooling mode, the heat-exchange medium condensed and thereby brought into a high-temperature state by the compressor 842 is passed to the outdoor heat exchanger 841 of the outdoor unit 840. In the outdoor heat exchanger 841, the outdoor fan 844 passes outdoor air to the outdoor heat exchanger 841, which thus takes away heat from the heat-exchange medium and thereby cools it. The heat-exchange medium is then passed through the expansion valve 843 to the heat exchanger 825, where the heat-exchange medium evaporates. The indoor air sucked in by the indoor fan 826 is passed through the heat exchanger 825, which takes heat away from the air. In this way, indoor air is cooled and circulated, and as a result the room is cooled.

In the heating mode, the heat-exchange medium is circulated in the opposite direction to the direction in which it is circulated in the cooling mode. Specifically, the condensed heat-exchange medium is passed to the indoor heat exchanger 825, and indoor air is passed through the indoor heat exchanger 825 and is thereby heated. In this way, the room is heated. The heat-exchange medium is passed through the expansion valve 843 to the outdoor heat exchanger 841, where the heat-exchange medium evaporates. The heat of the heat-exchange medium is exchanged with that of the outdoor air passed to the outdoor heat exchanger 841 by the outdoor fan 844. Thus, the heat-exchange medium takes away heat from the outdoor air, and then returns to the compressor 842.

Here, the flow of air is as follows. Air is sucked in through the inlet 831 formed in the front panel 803 of the indoor unit 801 and through the inlet 832 formed in the body casing 802 by the indoor fan 826. The air is then passed through the filters 809 and 810 to the heat exchanger 825. The air is blown to all over the surface of the heat exchanger 825, and this enhances the heat exchange efficiency of the heat exchanger 825. The air that has passed through the heat exchanger 825 is blown out through the outlet 804.

When the air conditioner starts operating, simultaneously a high alternating-current voltage is applied to the ion generating device unit 833, which thus starts generating negative and positive ions. Moreover, at the same time that the air conditioner starts operating, the stepping motor 885 is driven so that, as shown in FIG. 69A, the damper 881 moves in such a way that the second outlet 880 is opened. This causes the air flow passage D to communicate, through the confluence 834, with the outlet 804.

Part of the air sucked in through the inlet 831 and then passed through the filters 809 and 810 enters the air flow passage D, and is sucked into the ion generating device unit 833. The air is passed through the filter 863 of the unit case 864, which removes odors, dust, and other foreign particles from the air, and is then passed to the ion generating electrode member 202, which generates negative and positive ions therein. The air, now containing negative and positive ions, is blown out through the second outlet 880. The air blown out of the ion generating device unit 833 is then passed through the air flow passage D and then through the confluence 834 so as to be blown out through the outlet 804 together with the air that has been passed through the circulation passage C and subjected to heat exchange. In this way, air is circulated throughout the room by convection. As a result, indoor air is not only conditioned, but also sterilized, with airborne germs killed and removed therefrom by the action of positive and negative ions.

In this air conditioner, the ion generating device unit 833, which generates ions, can be operated independently. In this case, when the air conditioner is not in operation, the cluster switch 824 of the remote control unit 808 is turned to the "on" position. This causes a high alternating-current voltage to be applied to the ion generating electrode member 202, and also to the indoor fan 826 of the indoor unit 801. Moreover, the stepping motor 885 is driven so that, as shown in FIG. 69B, the damper 881 moves in such a way that the first outlet 879 is opened. This causes the air flow passage D to communicated with the ion outlet 836.

The air sucked in through the inlet 805 by the indoor fan 826 is passed through the air flow passage D by the blower 861, and is sucked into the ion generating device unit 833. The air blown out of the ion generating device unit 833, now containing negative and positive ions, is passed through the first outlet 879, and is blown out through the ion outlet 836 into the room. In this way, the ion generating device unit 833 can be operated independently of air conditioning to achieve sterilization, i.e. to kill airborne germs in indoor air. This enhances the usability of the air conditioner.

Moreover, by activating the dehumidifying/humidifying device 850, it is possible to adjust the properties of indoor air by dehumidifying or humidifying it. To achieve this, when the dehumidifying/humidifying device 850 is activated, simultaneously the operation of the ion generating device unit 833 is started. When the humidity switch 822 or the ventilation switch 823 of the remote control unit 808 is turned to the "on" position to start the operation of the dehumidifying/humidifying device 850, a high alternating-current voltage is applied to the ion generating device unit 833, and also to the indoor fan 826. Moreover, the stepping motor 885 is driven so that the damper 881 moves in such a way that the first outlet 879 is opened. This causes the air flow passage D to communicate with the ion outlet 836.

Thus, air containing negative and positive ions is blown out through the ion outlet 836, and air having its moisture content controlled is blown out through the dehumidifying/humidifying outlet 807. In this way, airborne germs are killed and removed from indoor air.

As another example of the ion generating device unit 833 of this embodiment, FIG. 71 shows an arrangement in which a wind direction adjusting means for varying the direction of the flow of air is additionally provided in the first outlet 879. In other respects, this modified version of the ion generating device unit 833 has the same structure as the original version of this embodiment described above.

As the wind direction adjusting means, a plurality of vertically arranged fins, together constituting a vertical louver 870, are rotatably fitted in the first outlet 879. The individual fins of the vertical louver 870 are coupled together by a coupling plate 871, and are positioned at a desired angle, or continuously swung, by a stepping motor (not shown). This makes it possible to blow out air containing ions in a particular direction, or uniformly in all directions.

As still another example of the ion generating device unit 833 of this embodiment, FIG. 72 shows an arrangement in which the ion generating device unit 833 is additionally provided with a control circuit board 872 having control and power-supply circuits, for driving the ion generating device 201 and the blower 861, formed thereon. Specifically, a housing 873 for housing the control circuit board 872 is formed integrally with the casing 861*a*, and the control circuit board 872 is removably housed in this housing 873. Moreover, as shown in FIG. 73, in the front face of the body casing 802, a connector 873 for connection with the ion generating device unit 833 is provided. This connector 874 is normally covered with a cover.

After the ion generating device unit 833 is fitted in a predetermined position inside the body casing 802, a cable from the control circuit board is connected to the connector 874. This makes it possible to feed a supply voltage and transmit control signals from the air conditioner to the ion generating device unit 833. The ion generating device unit 833, when designed in this way, can easily be fitted afterward, and thus can be offered as an accessory that the user can select if he or she wants it.

In this embodiment, an air conditioner is taken up as an example of an air conditioning apparatus that incorporates an ion generating device unit. However, the ion generating device unit maybe incorporated in an air conditioning apparatus of any kind, for example, an air purifier, dehumidifier, humidifier, refrigerator, kerosene fan heater, kerosene stove, electric stove, etc. In any case, it is possible to achieve sterilization by the action of negative and positive ions. In the ion generating device unit described above, the blower is arranged on the upstream side of the ion generating electrode member; however, it may be arranged on the downstream side thereof.

The number of outlets provided is not limited to two; that is, three or more outlets may be provided. In that case, a shutter is provided one for each outlet so that switching among the outlets is achieved by opening and closing those shutters in such a way that the outlets are opened and closed individually. This makes it possible to set the direction of the blown-out air by combining a plurality of outlets, and thereby permits the air conditioner to be used in various ways to suit various purposes.

Figure 74:
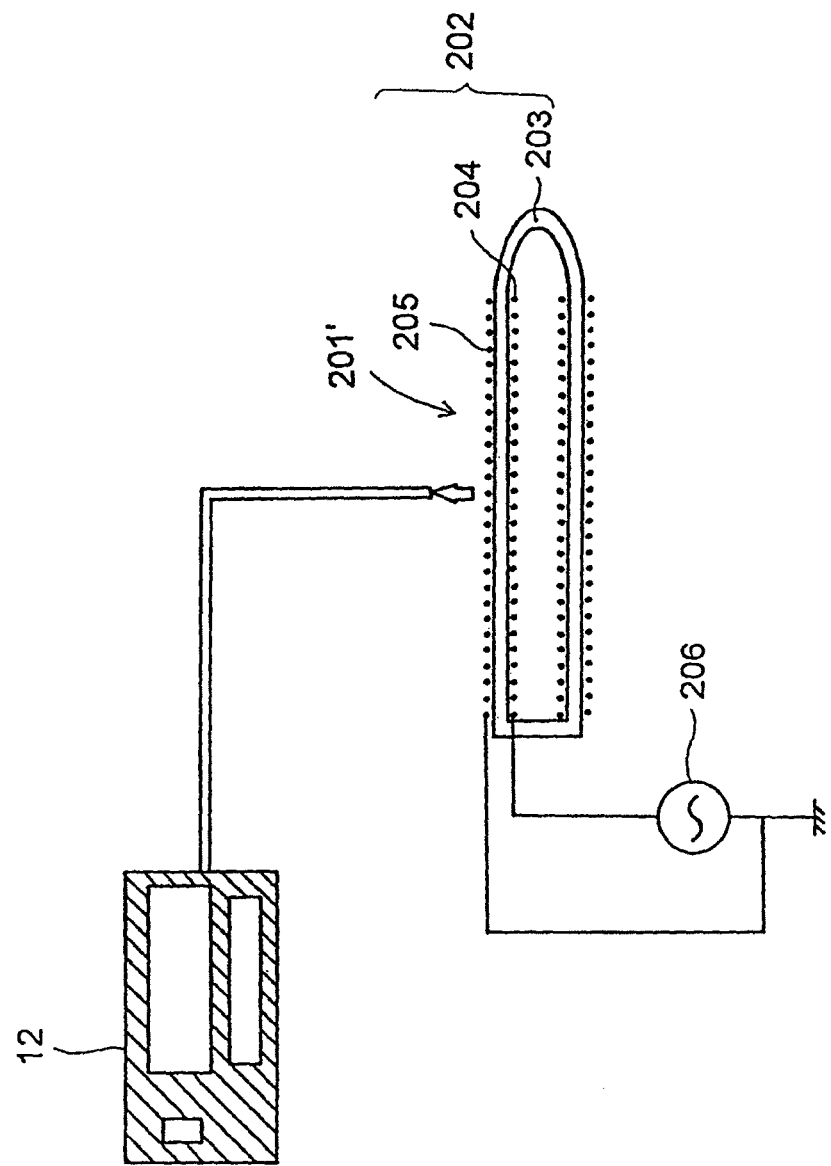
FIG. 74 is a diagram showing an outline of the configuration of the ion generating device of a seventeenth embodiment of the invention.

Now, a seventeenth embodiment of the invention will be described with reference to the drawings. FIG. 74 is a diagram showing an outline of the configuration of the ion generating device 201' of a seventeenth embodiment of the invention. In FIG. 74, reference numeral 202 represents the ion generating electrode member of the ion generating device 201 (see FIG. 8) of the seventh embodiment described earlier.

The ion generating device 201' is composed of an ion generating electrode member 202, a high alternating-current voltage source 206 connected to the inner and outer electrodes 204 and 205 thereof, which serve as a voltage application electrode and a grounding electrode respectively, and a power switch (not shown). To measure the concentration of ozone generated in the space around, an ozone concentration checker 12 is installed, with its ozone sensor arranged in the vicinity of the glass tube 203.

In the ion generating device 201' configured as described above, when the power switch is turned to the "on" position, negative and positive ions are generated on the side surface of the glass tube 203 of the ion generating electrode member 202. Simultaneously, ozone is generated as well. To measure the rate at which ozone is generated by the operation of the ion generating device 201', and the life of the ozone so generated, the following experiment was conducted.

Example 26

In the ion generating electrode member 202, as the glass tube 203, a cylindrical tube of Pyrex glass, having an internal diameter of 10 mm, 1.0 mm thick, and 150 mm long, was used. As the inner electrode 204, a wire mesh, 80 mm long, having 48 meshes/inch, and produced by plain-weaving wire of stainless steel 304, 0.23 mm across, was used. As the outer electrode 205, a wire mesh, 80 mm long, having 16 meshes/inch, and produced by plain-weaving wire of stainless steel 304, 0.4 mm across, was used.

The ion generating device 201', with its ion generating electrode member 202 structured as described above, was installed in a test space, 27 L in volume and hermetically enclosed in a vessel made of acrylic resin. Then, using the high alternating-current voltage source 206, an alternating-current voltage of 1.1 kV rms having a frequency of 12 kHz was applied to the inner electrode 204, with the outer electrode 205 at the ground potential. In this state, using the ozone concentration checker 12, the concentration of ozone generated by the ion generating device 201' was measured. As the ozone concentration checker 12, a UV absorption type ozone monitor, model EG-2001 manufactured by Ebara Jitsugyo Co., Ltd., Japan, was used.

Figure 75:
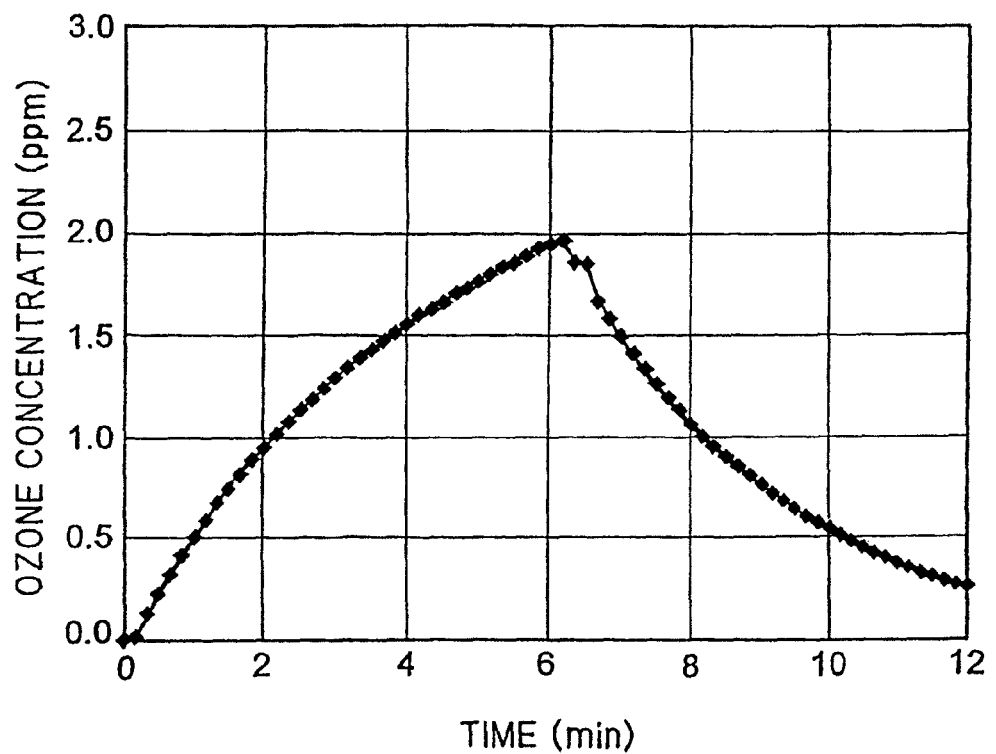
FIG. 75 is a graph showing the variation of ozone concentration observed using the ion generating device when, in an atmosphere in which the initial concentration of ozone was 0.001 ppm or lower, its power switch was kept in the "on" position for six minutes and then turned to the "off" position.

FIG. 75 shows the variation of ozone concentration observed when, in an atmosphere in which the initial concentration of ozone was 0.001 ppm or lower, the power switch 207 was kept in the "on" position for six minutes and then turned to the "off" position. As FIG. 75 shows, the variation of ozone concentration was approximated exponentially both when the power switch 207 was in the "on" position and when it was in the "off" position.

When ozone is generated indoors, as in an ordinary household, the variation of ozone concentration with time is given, if its initial value is assumed to be 0, by $$C_{OZONE} = (n_0/(\eta+K))(1-\exp(\eta+K)t))$$

where n0 represents the rate at which ozone is generated, η represents the decay coefficient of ozone (i.e. the reciprocal of the life r of ozone), K represents the ventilation rate, and t represents time.

On the other hand, the variation of ozone concentration due to natural decay is given by $$C_{OZONE} = C_0 \exp(-(\eta+K)t)$$

where $C_0$ represents the initial concentration of ozone.

By fitting these formulae to the curve of FIG. 75 representing the actually measured variation of ozone concentration with time, it is possible to calculate the rate of ozone generation and the life of ozone. In this specific case, the ozone generation rate $n_0$ and the life τ were calculated as 1.02 mg/min and 170.6 sec, respectively, assuming that the ventilation rate K was 0. Normally, the life τ of ozone in an ordinary atmosphere, as indoors in an ordinary household, is 180 sec or shorter. Therefore, the calculated life r of ozone is considered to be proper.

In this embodiment, on the basis of the ozone generation rate specific to the ion generating device 201, the periods for which the power switch 207 is kept in the "on" and "off" positions are controlled so that the ion generating device 201 operates intermittently. This makes it possible to secure a sufficient amount of negative and positive ions while minimizing the generation of ozone.

Figure 76:
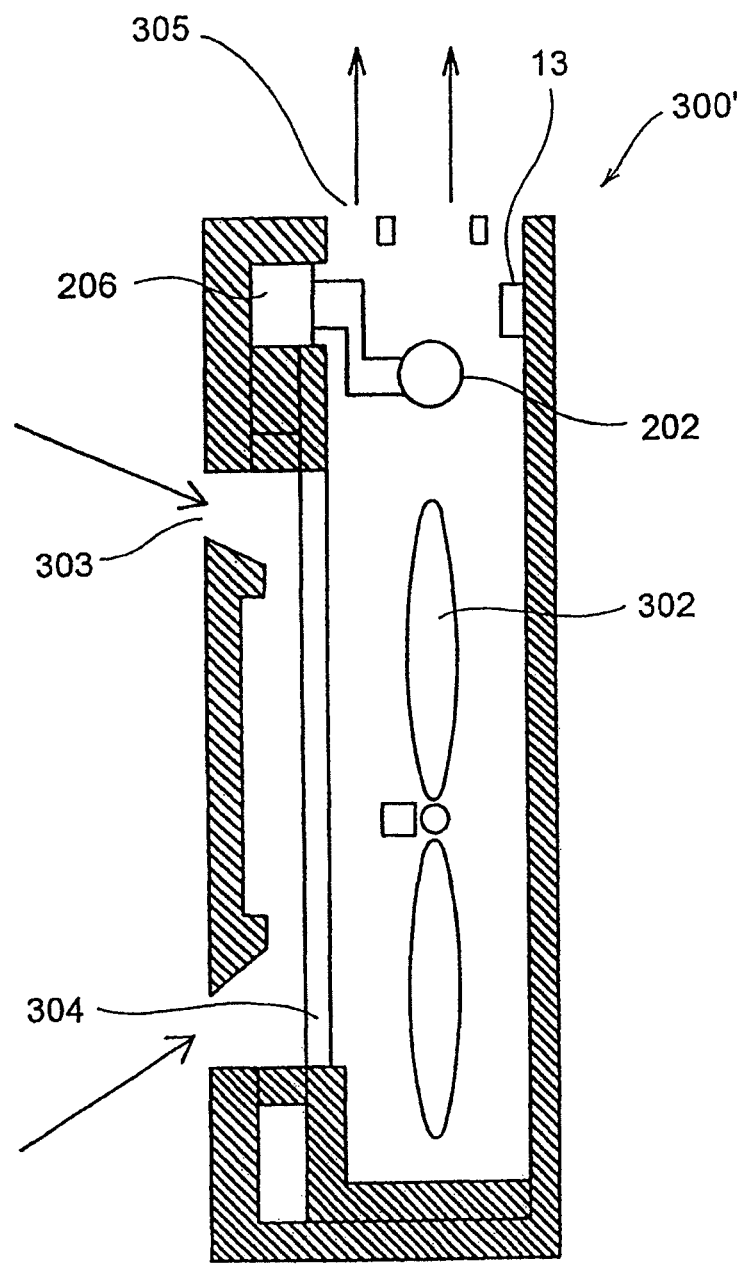
FIG. 76 is a side sectional view showing an outline of the structure of the air purifier of an eighteenth embodiment of the invention.

Now, an eighteenth embodiment of the invention will be described with reference to the drawings. FIG. 76 is a side sectional view showing an outline of the structure of the air purifier 300' of an eighteenth embodiment of the invention. In FIG. 76, such members as are found also in the air purifier 300 shown in FIG. 3 and described earlier in connection with the second embodiment are identified with the same reference numerals, and their explanations will not be repeated.

The main features of this embodiment are that, as shown in FIG. 76, the ion generating electrode member 202 of the ion generating device 201' (see FIG. 74) of the seventeenth embodiment described above is provided in the air flow passage, in the vicinity of the outlet 305, and that an ozone sensor 13 for monitoring the concentration of ozone is provided in the vicinity of the downstream side of the ion generating electrode member 202. As the ozone sensor 13, a sensor of a UV absorption type, or a sensor exploiting a polarography- or semiconductor-based method, is used.

When this air purifier 300', structured as described above, starts operating, the blowing fan 302 starts rotating. As a result, the air sucked through the inlet 303 into the air flow passage is passed through the filters 304, which remove dust and odors from the air, and is then blown out through the outlet 305. Meanwhile, if the ion generating device 201' is kept on, the negative and positive ions generated in the space around the ion generating electrode member 202 are blown out together with the clean air. In addition, the ozone sensor 13 monitors the concentration of the ozone generated around the ion generating electrode member 202 and then blown out.

Next, the sterilization performance of the air purifier 300' of this embodiment against airborne germs will be described in terms of a practical example. It is to be understood, however, that the air purifier 300' of this embodiment is not limited to the example specifically described below, but may be implemented with modifications made in operating conditions and other factors as required.

Example 27

In the air purifier 300', provided with the ion generating device 201' of the Example 26 described earlier, the ozone sensor 13 was placed in a position 5 cm away from the ion generating electrode member 202, the blowing fan 302 was rotated at an air-flow rate of 0.8 m³/min, the ion generating device 201' was activated intermittently at various intervals using the power switch 207, and the concentration of the ozone generated by the ion generating device 201' was measured. The results, i.e. the relationship between the on/off interval of the power switch 207 and the concentration of ozone, are shown in Table 10. The concentration of ozone was measured using a UV absorption type ozone monitor, model EG-2001 manufactured by Ebara Jitsugyo Co., Ltd., Japan.

As Table 10 shows, when the ion generating device 201' was made to operate continuously, the concentration of ozone was as high as 0.05 ppm, i.e. above the admitted safety level of 0.01 ppm. By contrast, when the ion generating device 201' was made to operate intermittently, depending on the intervals at which it was activated, the concentration of ozone was reduced to the admitted safety level or below.

Thus, by activating the ion generating device 201' intermittently at varying intervals while monitoring the concentration of generated ozone using the ozone sensor 13, it is possible to kill airborne germs by the action of the negative and positive ions generated by the ion generating device 201' while minimizing the generation of hazardous ozone.

Figure 77:
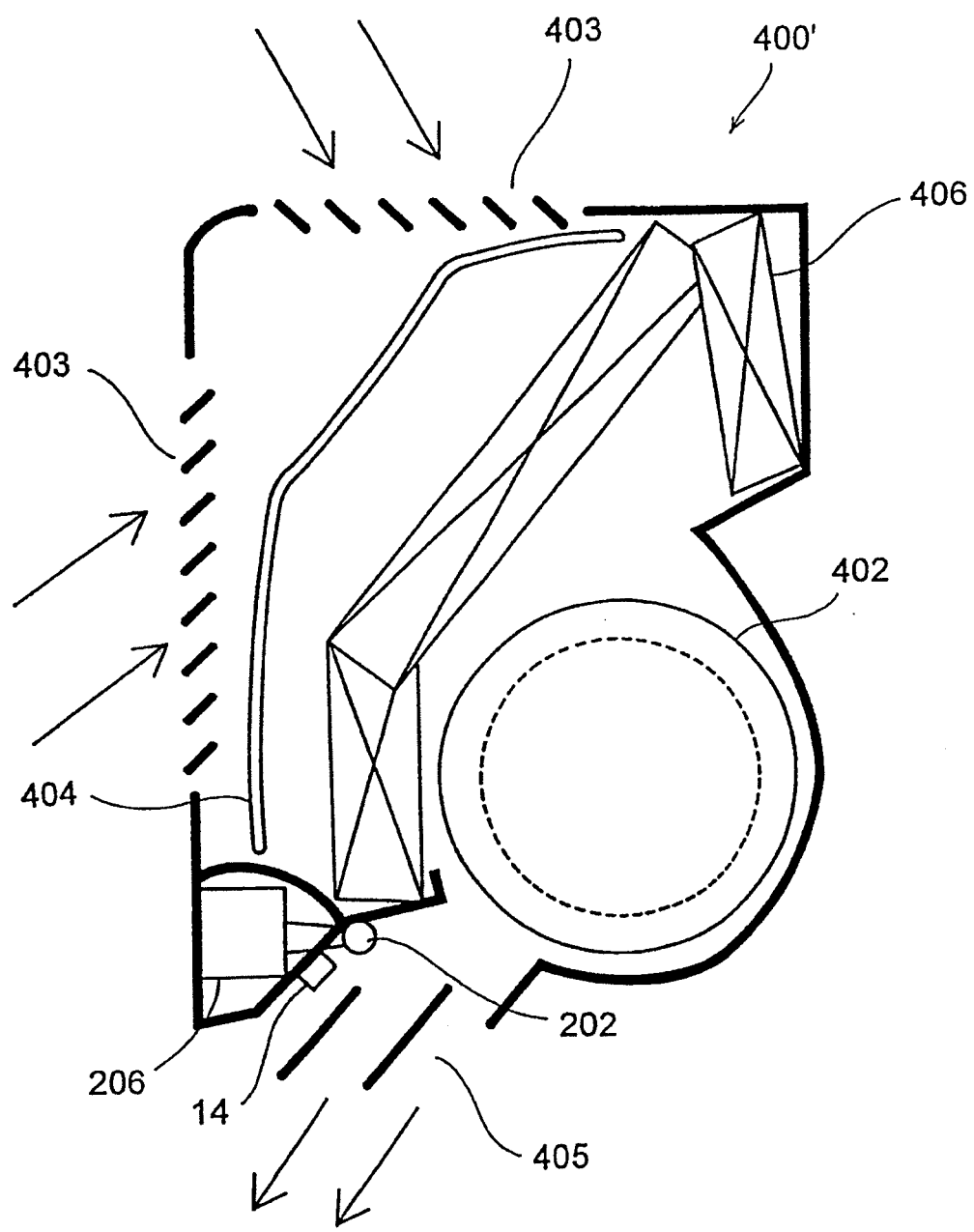
FIG. 77 is a side sectional view showing an outline of the structure of the air conditioner of a nineteenth embodiment of the invention.

Now, a nineteenth embodiment of the invention will be described with reference to the drawings. FIG. 77 is a side sectional view showing an outline of the structure of the air conditioner 400' of a nineteenth embodiment of the invention. In FIG. 77, such members as are found also in the air conditioner 400 shown in FIG. 4 and described earlier in connection with the third embodiment are identified with the same reference numerals, and their explanations will not be repeated.

The main features of this embodiment are that, as shown in FIG. 77, the ion generating electrode member 202 of the ion generating device 201' (see FIG. 74) of the seventeenth embodiment described above is provided in the air flow passage, in the vicinity of the outlet 405, and that an ozone sensor 14 for monitoring the concentration of ozone is provided in the vicinity of the downstream side of the ion generating electrode member 202. As the ozone sensor 14, a sensor of a UV absorption type, or a sensor exploiting a polarography- or semiconductor-based method, is used.

When this air conditioner 400', structured as described above, starts operating, the blowing fan 402 starts rotating. As a result, the air sucked through the inlet 403 into the air flow passage is passed through the filters 404, which remove dust and odors from the air, is then passed through the heat exchanger 406, which exchanges heat between the air and a cooling medium, and is then blown out through the outlet 405. Meanwhile, if the ion generating device 201' is kept on, the negative and positive ions generated in the space around the ion generating electrode member 202 are blown out together with the clean air. In addition, the ozone sensor 14 monitors the concentration of the ozone generated around the ion generating electrode member 202 and then blown out.

Next, the sterilization performance of the air conditioner 400' of this embodiment against airborne germs will be described in terms of a practical example. It is to be understood, however, that the air conditioner 400' of this embodiment is not limited to the example specifically described below, but may be implemented with modifications made in operating conditions and other factors as required.

Example 28

In the air conditioner 400', provided with the ion generating device 201' of the Example 26 described earlier, the ozone sensor 14 was placed in a position 5 cm away from the ion generating electrode member 202, the blowing fan 402 was rotated at an air-flow rate of 0.8 $m^3$/min, the ion generating device 201' was activated intermittently at various intervals using the power switch 207, and the concentration of the ozone generated by the ion generating device 201' was measured. The results, i.e. the relationship between the on/off interval of the power switch 207 and the concentration of ozone, are shown in Table 11. The concentration of ozone was measured using a UV absorption type ozone monitor, model EG-2001 manufactured by Ebara Jitsugyo Co., Ltd., Japan.

As Table 11 shows, when the ion generating device 201' was made to operate continuously, the concentration of ozone was relatively high, i.e. 0.05 ppm. By contrast, when the ion generating device 201' was made to operate intermittently, depending on the intervals at which it was activated, the concentration of ozone was reduced to 0.01 ppm or below.

Thus, by activating the ion generating device 201' intermittently at varying intervals while monitoring the concentration of generated ozone using the ozone sensor 14, it is possible to kill airborne germs by the action of the negative and positive ions generated by the ion generating device 201' while minimizing the generation of hazardous ozone.

Figure 78:
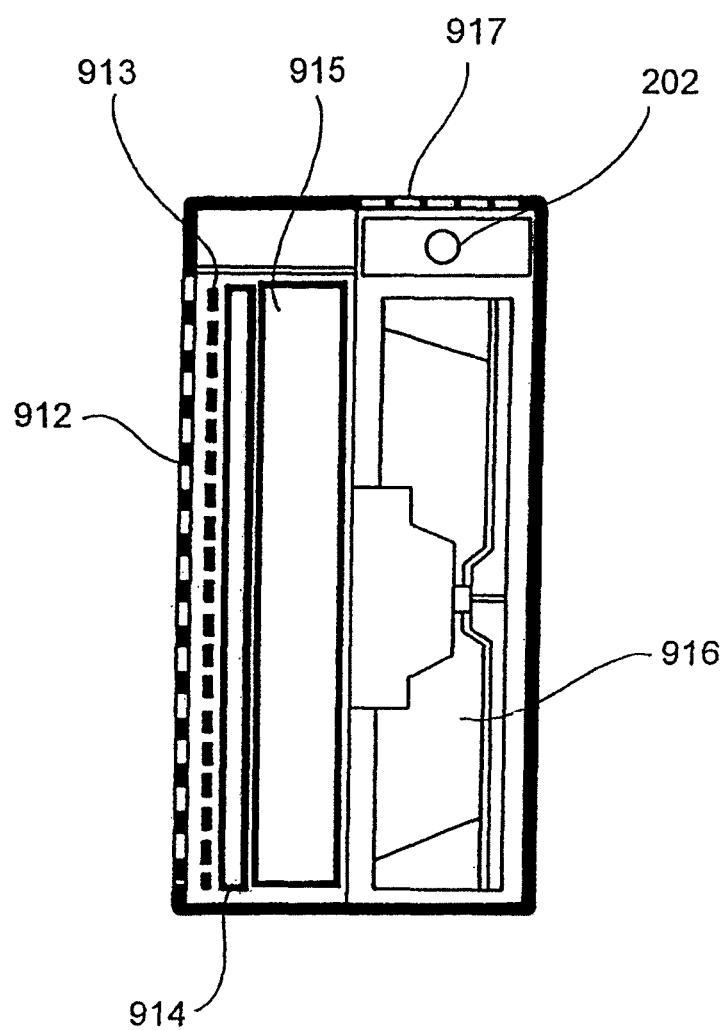
FIG. 78 is a side sectional view showing an outline of the structure of the air purifier of a twentieth embodiment of the invention.

Now, a twentieth embodiment of the invention will be described with reference to the drawings. FIG. 78 is a side sectional view showing an outline of the structure of the air purifier of a twentieth embodiment of the invention. In FIG. 78, reference numeral 202 represents the ion generating electrode member of the ion generating device 201 (see FIG. 8) of the seventh embodiment described earlier, reference numeral 912 represents an air inlet, reference numeral 913 represents a pre-filter arranged on the down-stream side of the air 912, reference numeral 914 represents an activated charcoal filter impregnated with an ozone decomposition catalyst such as manganese dioxide, reference numeral 915 represents a HEPA filter, reference numeral 916 represents a blowing fan, and reference numeral 917 represents an air outlet. In this arrangement, from a high alternating-current voltage source (not shown), an alternating-current voltage is applied to the inner electrode 204 of the ion generating electrode member 202, with the outer electrode 205 thereof at the ground potential.

It was observed that, when the inner and outer electrodes 204 and 205 of the ion generating electrode member 202 were formed as meshes of stainless steel, the concentration (ion/cc) of the negative and positive ions generated when the alternating-current voltage was applied varied according to the meshes/inch numbers of those meshes.

Example 29

As the glass tube 203, a cylindrical tube of Pyrex glass, having an internal diameter of 12 mm, 1.0 mm thick, and 150 mm long, was used. As the inner electrode 204, a wire mesh, 80 mm long, having 48 meshes/inch, and produced by plain-weaving wire of stainless steel 304, 0.23 mm across, was used. As the outer electrode 205, a metal mesh, 80 mm long, having 9 to 100 meshes/inch, and produced by plain-weaving wire of stainless steel 304, 0.15 to 0.22 mm across, was used.

Figure 79:
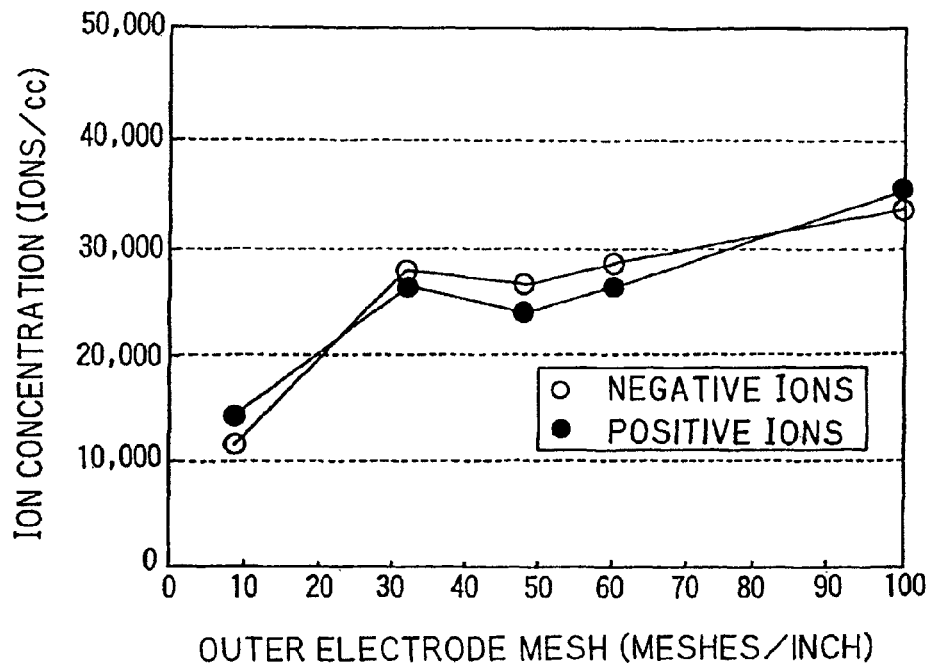
FIG. 79 is a graph showing the concentrations of negative and positive ions, as measured at a measurement point located 20 cm away from the side surface of the glass tube when an alternating-current voltage of 1.1 to 1.4 kV rms having a frequency of 15 kHz was applied to the inner electrode, with the outer electrode at the ground potential, in the ion generating electrode member of the air purifier, in which the glass tube was a cylindrical tube of Pyrex glass, having an internal diameter of 12 mm, 1.0 mm thick, and 150 mm long, the inner electrode was a wire mesh, 80 mm long, having 48 meshes/inch, and produced by plain-weaving wire of stainless steel 304, 0.23 mm across, and the outer electrode was a metal mesh, 80 mm long, having 9 to 100 meshes/inch, and produced by plain-weaving wire of stainless steel 304, 0.15 to 0.22 mm across.

Then, using the high alternating-current voltage source, an alternating-current voltage of 1.1 to 1.4 kV rms having a frequency of 15 kH was applied to the inner electrode 204, with the outer electrode 205 at the ground potential. Then, using an airborne ion counter, model 83-1001B manufactured by Dan Kagaku Co., Ltd., Japan, the concentrations of negative and positive ions with mobility of 1 $cm^2$/V·sec or higher were measured at a measurement point located 20 cm away from the side surface of the glass tube 203. The results in different cases are shown in FIG. 79. The concentrations of ions were measured using an airborne ion counter, model 83-1001B manufactured by Dan Kagaku Co., Ltd., Japan.

As FIG. 79 shows, the greater the meshes/inch number of the outer electrode 205, the higher the concentrations of ions tended to be. However, with a meshes/inch number of 30 or greater, the ion concentrations remained largely constant; specifically, about 200,000 to 400,000 ions/cc of negative and positive ions were detected.

When the alternating-current voltage is applied to the ion generating electrode member 202, a not small amount of ozone is generated together with ions. Ozone not only has an unpleasant odor, but is also hazardous to human health. Therefore, it is desirable to minimize the amount of ozone generated.

Example 30

As the glass tube 203, a cylindrical tube of Pyrex glass, having an internal diameter of 12 mm, 1.0 mm thick, and 150 mm long, was used. As the inner electrode 204, a wire mesh, 80 mm long, having 48 meshes/inch, and produced by plain-weaving wire of stainless steel 304, 0.23 mm across, was used. As the outer electrode 205, a metal mesh, 80 mm long, having 9 to 100 meshes/inch, and produced by plain-weaving wire of stainless steel 304, 0.15 to 0.22 mm across, was used.

Then, using the high alternating-current voltage source, an alternating-current voltage of 1.1 to 1.4 kV rms having a frequency of 15 kH was applied to the inner electrode 204, with the outer electrode 205 at the ground potential. Then, the concentration of ozone was measured at a measurement point located 20 cm away from the side surface of the glass tube 203. The concentration of ozone was measured using a UV absorption type ozone monitor, model EG-2001 manufactured by Ebara Jitsugyo Co., Ltd., Japan. The results in different cases are shown in FIG. 80.

Figure 80:
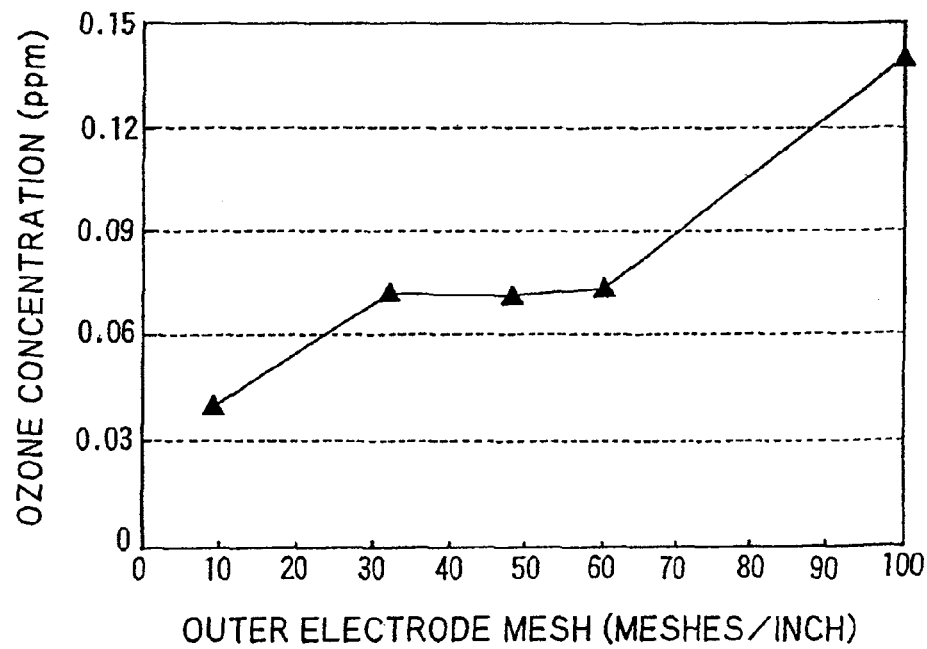
FIG. 80 is a graph showing the concentration of ozone, as measured at a measurement point located 20 cm away from the side surface of the glass tube when an alternating-current voltage was applied to the ion generating electrode member of the air purifier under the same conditions.

As FIG. 80 shows, the greater the meshes/inch number of the outer electrode 205, the higher the concentration of ozone tended to be. However, with a meshes/inch number in the range from 30 to 60, the ozone concentration remained largely constant.

Thus, it was found that, to maximize the generation of ions while minimizing the generating of ozone, in cases where the inner electrode 204 is formed out of a wire mesh having 48 meshes/inch, the preferable meshes/inch number of the outer electrode 205 is in the range from 30 to 60.

Next, the sterilization performance, against airborne germs, of the air purifier incorporating, in the vicinity of the air outlet 917 as shown in FIG. 78, the ion generating electrode member 202 having the characteristics described above was evaluated.

Example 31

The air purifier was installed in a test space 2.0 m long, 2.5 m wide, and 2.7 m high. Then, common bacteria and fungi that had been cultured on a culture medium beforehand were sprayed in the test space. Then, an alternating-current voltage of 1.1 to 1.4 kV rms is applied to the ion generating electrode member 202, and the air purifier was put into operation. Then, at predetermined time intervals, using an air sampler, model RCS manufactured by Biotest AG, Germany, the air inside the test space was extracted at a rate of 40 L/min for four minutes to measure the number of germs. The results are shown in Table 12.

In this example, as the glass tube 203, a cylindrical tube of Pyrex glass, having an internal diameter of 12 mm, 1.0 mm thick, and 150 mm long, was used. As the inner electrode 204, a wire mesh, 80 mm long, having 48 meshes/inch, and produced by plain-weaving wire of stainless steel 304, 0.23 mm across, was used. As the outer electrode 205, a metal mesh, 80 mm long, having 48 meshes/inch, and produced by plain-weaving wire of stainless steel 304, 0.15 to 0.22 mm across, was used. For comparison, the same experiment was conducted using, as the inner and outer electrodes 204 and 205, wire meshes both having 100 meshes/inch.

In three hours after the air purifier 300 started operating, most of the common bacteria and fungi, specifically 92% and 92% respectively, were killed. In the comparative example, in three hours, 82% and 82% of the common bacteria and fungi, respectively, were removed. Thus, more effective sterilization was achieved in Example 31 than in the comparative example. Moreover, most of the ozone generated together with the negative and positive ions was decomposed by the activated charcoal filter 914 impregnated with an ozone decomposition catalyst, and no odor of ozone was perceived.

This proves that the air purifier incorporating the ion generating electrode member 202 of this embodiment is capable of effectively killing airborne germs.

Figure 81:
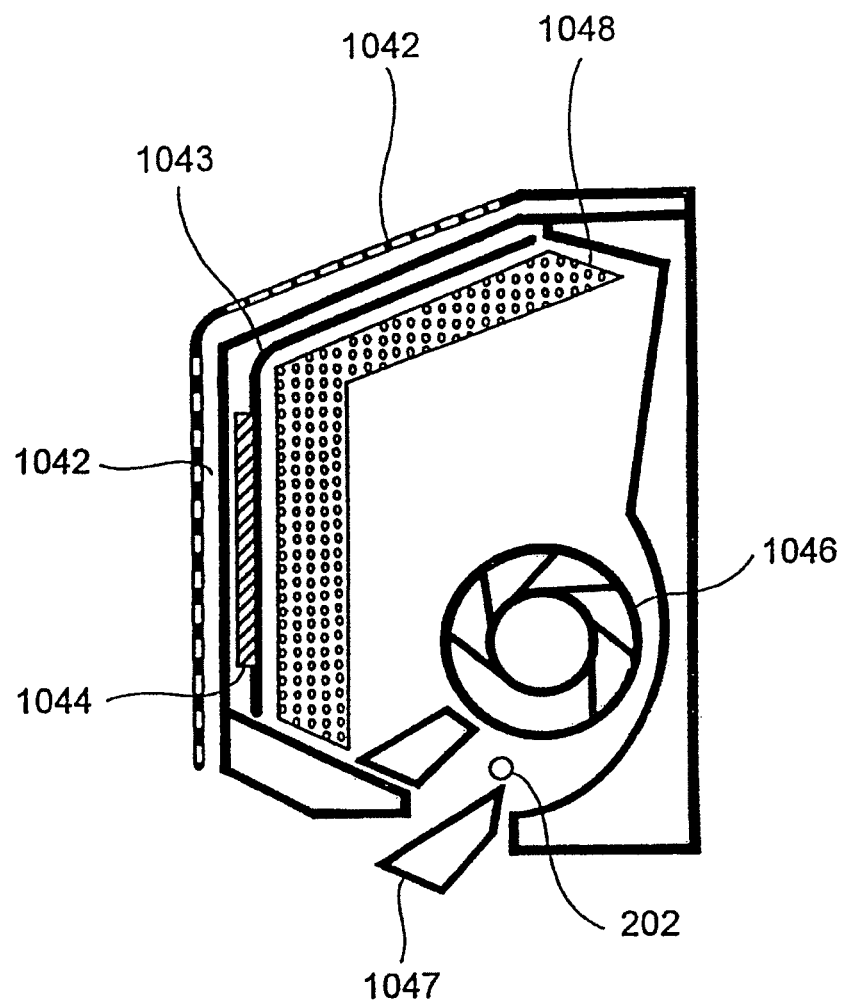
FIG. 81 is a side sectional view showing an outline of the structure of the air conditioner of a twenty-first embodiment of the invention.

Now, a twenty-first embodiment of the invention will be described with reference to the drawings. FIG. 81 is a side sectional view showing an outline of the structure of the air conditioner of a twenty-first embodiment of the invention. In FIG. 81, reference numeral 202 represents the ion generating electrode member of the ion generating device 201 (see FIG. 8) of the seventh embodiment described earlier, reference numeral 1042 represents an air inlet, reference numeral 1043 represents a pre-filter arranged on the down-stream side of the air inlet 42, reference numeral 1044 represents an activated charcoal filter impregnated with an ozone decomposition catalyst such as manganese dioxide, reference numeral 1046 represents a blowing fan, reference numeral 1047 represents an air outlet, and reference numeral 1048 represents a heat exchanger.

Next, the sterilization performance, against airborne germs, of the air conditioner incorporating, in the vicinity of the air outlet 1042 as shown in FIG. 81, the ion generating electrode member 202 having the characteristics described earlier in connection with the twentieth embodiment was evaluated.

Example 32

The air conditioner was installed in a test space 2.0 m long, 2.5 m wide, and 2.7 m high. Then, common bacteria and fungi that had been cultured on a culture medium beforehand were sprayed in the test space. Then, an alternating-current voltage of 1.1 to 1.4 kV rms is applied to the ion generating electrode member 202, and the air conditioner was put into operation. Then, at predetermined time intervals, using an air sampler, model RCS manufactured by Biotest AG, Germany, the air inside the test space was extracted at a rate of 40 L/min for four minutes to measure the number of germs. The results are shown in Table 13.

In this example, as the glass tube 203, a cylindrical tube of Pyrex glass, having an internal diameter of 12 mm, 1.0 mm thick, and 150 mm long, was used. As the inner electrode 204, a wire mesh, 80 mm long, having 48 meshes/inch, and produced by plain-weaving wire of stainless steel 304, 0.23 mm across, was used. As the outer electrode 205, a metal mesh, 80 mm long, having 48 meshes/inch, and produced by plain-weaving wire of stainless steel 304, 0.15 to 0.22 mm across, was used. For comparison, the same experiment was conducted using, as the inner and outer electrodes 204 and 205, wire meshes both having 100 meshes/inch.

In three hours after the air conditioner started operating, most of the common bacteria and fungi, specifically 91% and 92% respectively, were killed. In the comparative example, in three hours, 80% and 87% of the common bacteria and fungi, respectively, were removed. Thus, more effective sterilization was achieved in Example 32 than in the comparative example. Moreover, most of the ozone generated together with the negative and positive ions was decomposed by the activated charcoal filter 1044 impregnated with an ozone decomposition catalyst, and no odor of ozone was perceived.

This proves that the air conditioner incorporating the ion generating electrode member 202 of this embodiment is capable of effectively killing airborne germs.

In the examples specifically described hereinbefore, as the inner and outer electrodes 204 and 205, wire meshes produced by plain-weaving wire of stainless 304, which is an electrically conductive and oxidation-resistant material, were used. However, those electrodes may be made of any other metal as long as it is an oxidation-resistant material, for example, tungsten, platinum, gold, silver, or palladium. In particular when a noble metal such as platinum, gold, silver, or palladium is used, the electrodes may be produced by forming a coat of that metal on the surface of wire meshes of a less expensive metal such as titanium.

Obviously, many modifications and variations of the present invention are possible in light of the above teachings. It is therefore to be understood that within the scope of the appended claims, the invention may be practiced other than as specifically described.

INDUSTRIAL APPLICABILITY

As described hereinbefore, according to the present invention, a sterilization method involves generating, as negative and positive ions, $O_2^-(H_2O)_n$ (where n is a natural number) and $H^+(H_2O)_m$ (where m is a natural number), respectively, and discharging these ions into the air so that airborne germs are killed through an oxidization reaction by hydrogen peroxide $H_2O_2$ or radical hydroxyl OH generated as an active species through a chemical reaction between the negative and positive ions.

Here, if the concentrations of the negative and positive ions are both 10,000 ions/cc or higher at a distance of 10 cm from the point at which those ions are generated, it is possible to achieve satisfactory sterilization.

According to the present invention, an ion generating device is provided with a dielectric, a first electrode, and a second electrode, and the first and second electrodes are arranged so as to face each other with the dielectric disposed in between. The ion generating device generates, as negative and positive ions, $O_2^-(H_2O)_n$ (where n is a natural number)

and H$^+$(H$_2$O)$_m$ (where m is a natural number), respectively, by applying an alternating-current voltage between the first and second electrodes. These ions are discharged into the air so that airborne germs are killed through an oxidization reaction by hydrogen peroxide H$_2$O$_2$ or radical hydroxyl OH generated as an active species through a chemical reaction between the negative and positive ions that takes place after the generation of those ions.

Here, sufficient concentrations of the negative and positive ions to achieve satisfactory sterilization are secured by the application of a comparatively low alternating-current voltage of 2.0 kV rms or lower. The concentrations of the negative and positive ions thus secured are both 10,000 ions/cc or higher at a distance of 10 cm from the point at which the ions are generated.

More specifically, in one arrangement, the ion generating device is provided with a dielectric that is cylindrical in shape, an inner electrode that is formed as a mesh, and an outer electrode that is formed as a mesh, and the inner and outer electrodes are arranged so as to face each other with the dielectric disposed in between. The ion generating device generates negative and positive ions by applying an alternating-current voltage between the inner and outer electrodes.

Here, the inner electrode may be formed into a cylindrical shape by rolling a material thereof in such a way that, when the inner electrode is fitted along the inner surface of the cylindrical dielectric, opposite side edges of the rolled material overlap. This makes it possible to put the inner electrode into contact with the inner surface of the cylindrical dielectric easily and reliably.

Here, if it is assumed that the external diameter of the dielectric is 20 mm or less, that the thickness thereof is 1.6 mm or less, that the inner electrode has 40 meshes/inch, and that the outer electrode has 16 meshes/inch, then sufficient concentrations of the negative and positive ions to achieve satisfactory sterilization with minimum generation of ozone are secured by the application of a comparatively low alternating-current voltage of 2.0 kV rms or lower. The concentrations of the negative and positive ions thus secured are both 10,000 ions/cc or higher at a distance of 10 cm from the point at which the ions are generated.

The dielectric may be stopped at both ends with elastic rubber members so that the inner and outer electrodes do not move relative to each other along the axis of the dielectric. This helps stabilize the performance of the ion generating device so that it generates negative and positive ions with better reproducibility.

In this case, the elastic rubber members are preferably made of ethylene-propylene rubber, which is resistant to ozone.

Moreover, as the leads that are connected to the inner and outer electrodes are preferably used stainless steel wires coated with a polyethylene fluoride resin, which also is resistant to ozone.

In this case, the inner electrode needs to be at least thick enough to permit one of the leads to be bonded thereto.

The inner or outer electrode may be provided with a means for improving the contact thereof with the dielectric. This helps further stabilize the performance of the ion generating device.

The surface of the dielectric may be impregnated with a catalyst for promoting decomposition of ozone. This helps reduce the concentration of ozone generated as a byproduct when the ion generating device generates the ions.

Instead, the inner or outer electrode may be impregnated with a catalyst for promoting decomposition of ozone.

Instead, an ozone decomposition catalyst impregnated member impregnated with a catalyst for promoting decomposition of ozone may be provided at a distance from the dielectric. This makes it possible to use as the alternating-current voltage a voltage of 2.5 kV rms or lower.

In another arrangement, the ion generating device according to the present invention is provided with a dielectric that is cylindrical in shape, an inner electrode that is formed as a sheet, and an outer electrode that is formed as a mesh, and the inner and outer electrodes are arranged so as to face each other with the dielectric disposed in between. The ion generating device generates negative and positive ions by applying an alternating-current voltage between the inner and outer electrodes.

In this arrangement, electric discharge takes place between electrodes of which one acts as an aggregate of point and the other a line. This ensures stable generation of negative and positive ions. Moreover, by modifying this arrangement in similar manners as with the first arrangement described above, it is possible to gain similar advantages.

The outer electrode may be made longer than the inner electrode along their axis, and the inner and outer electrodes may be arranged in such a way that, when the outer electrode is projected onto the inner electrode, the inner electrode lies inside the projected view of the outer electrode. This further enhances the performance of the ion generating device.

In this case, the inner electrode may be formed out of a polygonal sheet having a number of corners so that, when the inner electrode is formed into a cylindrical shape by rolling the polygonal sheet, at least one of the corners protrudes from an end of the cylinder. Such a corner protruding from the inner electrode makes the electric field more likely to concentrate on it, and thereby helps electric discharge occur with more stability than with a cylinder with trimmed ends.

The inner electrode may have a plurality of holes formed therein, with projections formed around the holes so as to protrude toward the dielectric. This makes the electric field more likely to concentrate on the side surface of the cylinder as well, and thus helps electric discharge occur stably and uniformly over the entire side surface of the inner electrode.

According to the present invention, an ion generating apparatus is provided with, in addition to an ion generating device as described above, a high alternating-current voltage source for feeding the ion generating device with the alternating-current voltage with which the ion generating device generates the negative and positive ions, and a blower for producing a forced flow of the negative and positive ions generated by the ion generating device.

With this ion generating apparatus, the negative and positive ions generated by the ion generating device fed with the alternating-current voltage from the high alternating-current voltage source can be discharged into a large expanse of air by the action of the blower so that airborne germs are killed by the action of those ions.

According to the present invention, an air conditioning apparatus is provided with, in addition to an ion generating device as described above, a high alternating-current voltage source for feeding the ion generating device with the alternating-current voltage with which the ion generating device generates the negative and positive ions, a blower for producing a forced flow of the negative and positive ions generated by the ion generating device, an inlet through which air is sucked in, an outlet through which, by the action of the blower, the negative and positive ions generated by the ion generating device is blown out together with the air sucked in through the inlet, and a filter, disposed in the air flow passage leading from the inlet to the outlet, for removing foreign particles from the air.

With this air conditioning apparatus, the negative and positive ions generated by the ion generating device fed with the alternating-current voltage from the high alternating-current voltage source can be discharged into a large expanse of air by the action of the blower so that airborne germs are killed by the action of those ions. Moreover, while the air is circulated, the filter removes dust and other foreign particles as well as odors from the air. This helps realize a comfortable and clean living environment.

Alternatively, according to the present invention, an air conditioning apparatus is provided with, in addition to an ion generating device as described above, a high alternating-current voltage source for feeding the ion generating device with the alternating-current voltage with which the ion generating device generates the negative and positive ions, a blower for producing a forced flow of the negative and positive ions generated by the ion generating device, an inlet through which air is sucked in, an outlet through which, by the action of the blower, the negative and positive ions generated by the ion generating device is blown out together with the air sucked in through the inlet, a filter, disposed in the air flow passage leading from the inlet to the outlet, for removing foreign particles from the air, and a heat exchanger disposed in the air flow passage.

With this air conditioning apparatus, the negative and positive ions generated by the ion generating device fed with the alternating-current voltage from the high alternating-current voltage source can be discharged into a large expanse of air by the action of the blower so that airborne germs are killed by the action of those ions. Moreover, while the air is circulated, the temperature or humidity of the air is adjusted by the heat exchanger, and the filter removes dust and other foreign particles as well as odors from the air. This helps realize a comfortable and clean living environment.

TABLE 1

| | | Air Purifier Operation Time(Hours) | | | |
|---|---|---|---|---|---|
| | | 0 | 1 | 3 | 5 |
| Common Bacteria | Number (m$^{-3}$) | 250 | 110 | 70 | 35 |
| | Reduced (%) | 0 | 56 | 72 | 86 |
| Fungi | Number (m$^{-3}$) | 510 | 215 | 125 | 50 |
| | Reduced (%) | 0 | 58 | 75 | 90 |

TABLE 2

| | | Air Conditioner Operation Time(Hours) | | | |
|---|---|---|---|---|---|
| | | 0 | 1 | 3 | 5 |
| Common Bacteria | Number (m$^{-3}$) | 240 | 100 | 60 | 35 |
| | Reduced (%) | 0 | 58 | 75 | 85 |
| Fungi | Number (m$^{-3}$) | 520 | 210 | 115 | 40 |
| | Reduced (%) | 0 | 60 | 78 | 92 |

TABLE 3

| | | Air Purifier Operation Time(Hours) | | | |
|---|---|---|---|---|---|
| | | 0 | 1 | 3 | 5 |
| Common Bacteria | Number (m$^{-3}$) | 260 | 120 | 75 | 40 |
| | Reduced (%) | 0 | 54 | 71 | 85 |
| Fungi | Number (m$^{-3}$) | 500 | 205 | 120 | 45 |
| | Reduced (%) | 0 | 59 | 76 | 91 |

TABLE 4

| | | Air Conditioner Operation Time(Hours) | | | |
|---|---|---|---|---|---|
| | | 0 | 1 | 3 | 5 |
| Common Bacteria | Number (m$^{-3}$) | 250 | 100 | 65 | 40 |
| | Reduced (%) | 0 | 60 | 74 | 84 |
| Fungi | Number (m$^{-3}$) | 520 | 215 | 115 | 50 |
| | Reduced (%) | 0 | 59 | 78 | 90 |

TABLE 5

| | Capacitance pF | Loss % |
|---|---|---|
| No Displacement | 38.8 | |
| 1 mm Displaced | 38.2 | −1.55 |
| 2 mm Displaced | 37.8 | −2.58 |
| 3 mm Displaced | 37.3 | −3.87 |
| 4 mm Displaced | 36.8 | −5.15 |
| 5 mm Displaced | 36.2 | −6.70 |

TABLE 6

| Frequency [kHz] | Voltage rms [V] | Negative Ion Concentration [ions/cc] | Positive Ion Concentration [ions/cc] | Ozone Concentration [ppm] |
|---|---|---|---|---|
| 25 | 44 | 130 | 79 | 0.001 or lower |
| 25 | 440 | 4,966 | 13,910 | 0.001 or lower |
| 25 | 1,100 | 32,551 | 36,271 | 0.001 or lower |
| 0.06 | 2,000 | 26,794 | 11,443 | 0.005 |
| 17 | 1,700 | 39,067 | 30,204 | 0.005 |
| 17 | 2,000 | 54,867 | 53,843 | 0.015 |
| 26 | 2,000 | 52,551 | 55,681 | 0.010 |
| 30 | 1,800 | 33,163 | 31,655 | 0.005 |

TABLE 7

| Glass Tube | | |
|---|---|---|
| External Diameter (mm) | Thickness (mm) | Capacitance (pF) |
| 17 | 1.2 | 34.0 |
| 20 | 1.2 | 36.0 |
| 20 | 1.6 | 35.0 |
| 24 | 1.2 | 51.0 |

TABLE 8

| | | Air Purifier Operation Time (Hours) | | | | | |
|---|---|---|---|---|---|---|---|
| | | 0 | 1 | 2 | 3 | 4 | 5 |
| Common Bacteria | Number (m$^{-3}$) | 240 | 90 | 55 | 40 | 30 | 25 |
| | Reduced (%) | 0 | 60 | 77 | 83 | 88 | 90 |
| Fungi | Number (m$^{-3}$) | 520 | 165 | 105 | 65 | 45 | 40 |
| | Reduced (%) | 0 | 68 | 80 | 88 | 91 | 92 |

TABLE 9

| | | Air Conditioner Operation Time(Hours) | | | | | |
|---|---|---|---|---|---|---|---|
| | | 0 | 1 | 2 | 3 | 4 | 5 |
| Common Bacteria | Number (m$^{-3}$) | 230 | 85 | 45 | 30 | 20 | 15 |
| | Reduced (%) | 0 | 63 | 80 | 87 | 91 | 93 |
| Fungi | Number (m$^{-3}$) | 500 | 150 | 85 | 50 | 40 | 30 |
| | Reduced (%) | 0 | 70 | 83 | 90 | 92 | 94 |

TABLE 10

| Example | Intermittent Operation | 3 sec ON then 3 sec OFF | 5 sec ON then 5 sec OFF | 10 sec ON then 10 sec OFF |
|---|---|---|---|---|
| | Ozone Concentration | 0.006 ppm | 0.008 ppm | 0.015 ppm |
| Comparative Example | Continuous Operation | Always ON | | |
| | Ozone Concentration | 0.05 ppm | | |

TABLE 11

| Example | Intermittent Operation | 3 sec ON then 3 sec OFF | 5 sec ON then 5 sec OFF | 10 sec ON then 10 sec OFF |
|---|---|---|---|---|
| | Ozone Concentration | 0.006 ppm | 0.008 ppm | 0.015 ppm |
| Comparative Example | Continuous Operation | Always ON | | |
| | Ozone Concentration | 0.05 ppm | | |

TABLE 12

| | | | Air Purifier Operation Time (Hours) | | | | | |
|---|---|---|---|---|---|---|---|---|
| | | | 0 | 1 | 2 | 3 | 4 | 5 |
| Example | Common Bacteria | Number (m$^{-3}$) | 245 | 75 | 35 | 20 | 10 | 5 |
| | | Reduced (%) | 0 | 69 | 86 | 92 | 96 | 98 |
| | Fungi | Number (m$^{-3}$) | 500 | 140 | 85 | 40 | 25 | 15 |
| | | Reduced (%) | 0 | 72 | 83 | 92 | 95 | 97 |
| Comparative Example | Common Bacteria | Number (m$^{-3}$) | 250 | 120 | 60 | 45 | 30 | 15 |
| | | Reduced (%) | 0 | 52 | 76 | 82 | 88 | 94 |
| | Fungi | Number (m$^{-3}$) | 500 | 300 | 140 | 90 | 50 | 30 |
| | | Reduced (%) | 0 | 40 | 72 | 82 | 90 | 94 |

| Example | Inner Electrode (Voltage Application Electrode): 48 meshes/inch |
|---|---|
| | Outer Electrodes (Grounding Electrode): 48 meshes/inch |
| Comparative Example | Inner Electrode (Voltage Application Electrode): 100 meshes/inch |
| | Outer Electrodes (Grounding Electrode): 100 meshes/inch |

TABLE 13

| | | | Air Conditioner Operation Time(Hours) | | | | | |
|---|---|---|---|---|---|---|---|---|
| | | | 0 | 1 | 2 | 3 | 4 | 5 |
| Example | Common Bacteria | Number (m$^{-3}$) | 220 | 80 | 35 | 20 | 15 | 10 |
| | | Reduced (%) | 0 | 64 | 84 | 91 | 93 | 95 |
| | Fungi | Number (m$^{-3}$) | 530 | 140 | 70 | 40 | 30 | 15 |
| | | Reduced (%) | 0 | 74 | 87 | 92 | 94 | 97 |
| Comparative Example | Common Bacteria | Number (m$^{-3}$) | 230 | 150 | 70 | 45 | 25 | 15 |
| | | Reduced (%) | 0 | 35 | 70 | 80 | 89 | 93 |
| | Fungi | Number (m$^{-3}$) | 520 | 250 | 130 | 70 | 45 | 20 |
| | | Reduced (%) | 0 | 52 | 75 | 87 | 91 | 96 |

| Example | Inner Electrode (Voltage Application Electrode): 48 meshes/inch |
|---|---|
| | Outer Electrodes (Grounding Electrode): 48 meshes/inch |
| Comparative Example | Inner Electrode (Voltage Application Electrode): 100 meshes/inch |
| | Outer Electrodes (Grounding Electrode): 100 meshes/inch |

What is claimed is:

1. An ion generating device comprising:
   a cylindrical dielectric;
   a first electrode provided along an inner surface of the dielectric;
   a second electrode provided along an outer surface of the dielectric;
   a stopping member for stopping an opening in the dielectric; and
   an alternating-current voltage application circuit for applying an alternating-current voltage between the first and second electrodes to generate positive and negative ions.

2. The ion generating device according to claim 1, wherein the first electrode is formed of an electrically conductive sheet material, and
   the second electrode is formed of an electrically conductive mesh material.

3. The ion generating device according to claim 2, wherein the first electrode is formed of a polygonal sheet material.

4. The ion generating device according to claim 1, wherein the structure comprises a plug member that stops an opening portion of the dielectric, the plug member keeping an inside of the cylindrical dielectric airtight and preventing the first and second electrodes from being displaced from each other.

5. The ion generating device according to claim 4, wherein the first electrode is formed of an electrically conductive sheet material, and
   the second electrode is formed of an electrically conductive mesh material.

6. The ion generating device according to claim 5, wherein the first electrode is formed of a polygonal sheet material.

7. The ion generating device according to claim 1, wherein the first and second electrodes are both formed of an electrically conductive mesh material.

8. The ion generating device according to claim 7, wherein the first electrode has a finer mesh than the second electrode.

9. The ion generating device according to claim 1, wherein the first electrode is formed of an electrically conductive sheet material and an electrically conductive mesh material, and
   the second electrode is formed of an electrically conductive mesh material.

10. The ion generating device according to claim 9, wherein
the first electrode has a finer mesh than the second electrode.

* * * * *